(12) United States Patent
Davioud-Charvet et al.

(10) Patent No.: US 9,090,549 B2
(45) Date of Patent: Jul. 28, 2015

(54) 1,4-NAPHTHOQUINONES DERIVATIVES AND THERAPEUTIC USE THEREOF

(75) Inventors: Elisabeth Davioud-Charvet, Perenchies (FR); Tobias Muller, Eppelheim (DE); Holger Bauer, Heidelberg (DE); R. Heiner Schirmer, Heidelberg (DE)

(73) Assignees: CENTRE NATIONAL DE LA RECHERCHE SCIENTIFIQUE (C.N.R.S.), Paris (FR); REPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 988 days.

(21) Appl. No.: 12/934,382
(22) PCT Filed: Mar. 25, 2009
(86) PCT No.: PCT/EP2009/053483
§ 371 (c)(1),
(2), (4) Date: Nov. 22, 2010
(87) PCT Pub. No.: WO2009/118327
PCT Pub. Date: Oct. 1, 2009

(65) Prior Publication Data
US 2011/0059972 A1 Mar. 10, 2011

(30) Foreign Application Priority Data
Mar. 26, 2008 (EP) .................... 08290278

(51) Int. Cl.
*A61K 31/535* (2006.01)
*A61K 31/4965* (2006.01)
*A61K 31/47* (2006.01)
*A61K 31/122* (2006.01)
*C07C 49/603* (2006.01)
*C07C 50/14* (2006.01)
*C07C 46/00* (2006.01)
*C07C 46/02* (2006.01)
*C07C 50/10* (2006.01)
*C07C 50/24* (2006.01)
*C07C 50/32* (2006.01)
*C07C 50/38* (2006.01)
*C07C 69/95* (2006.01)
(Continued)

(52) U.S. Cl.
CPC ............... *C07C 50/14* (2013.01); *C07C 46/00* (2013.01); *C07C 46/02* (2013.01); *C07C 50/10* (2013.01); *C07C 50/24* (2013.01); *C07C 50/32* (2013.01); *C07C 50/38* (2013.01); *C07C 69/95* (2013.01); *C07C 205/46* (2013.01); *C07C 225/24* (2013.01); *C07C 255/29* (2013.01); *C07C 255/56* (2013.01); *C07C 271/28* (2013.01); *C07D 295/096* (2013.01); *C07D 295/116* (2013.01); *C07C 2102/10* (2013.01)

(58) Field of Classification Search
CPC . A61K 31/5375; A61K 31/495; A61K 31/47; A61K 31/122; C07D 295/205; C07D 295/116; C07D 215/24; C07C 50/32; C07C 50/12

USPC ........... 514/237.5, 255.04, 255.01, 311, 681; 544/172, 389, 392, 395; 546/178; 568/327

See application file for complete search history.

(56) References Cited

U.S. PATENT DOCUMENTS 5,244,917 A * 9/1993 Petraitis et al. ............... 514/468
2004/0022787 A1* 2/2004 Cohen et al. ............... 424/144.1

FOREIGN PATENT DOCUMENTS

EP 0301861 A1 * 1/1989
JP 2005035988 10/2005

OTHER PUBLICATIONS

Louis F. Fieser, Russel H. Brown, Synthesis of Naphthoquinones for Studies of the Inhibition of Enzyme Systems, Journal of the American Chemical Society (1949), 71, 3609-3614.*

(Continued)

*Primary Examiner* — Kendra D Carter
*Assistant Examiner* — Jason A Deck
(74) *Attorney, Agent, or Firm* — Young & Thompson

(57) ABSTRACT

1,4 naphthoquinones derivatives, of formula (I)

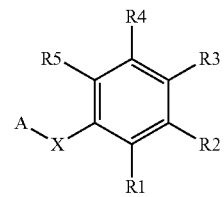

(I)

wherein A is selected from the following rings:

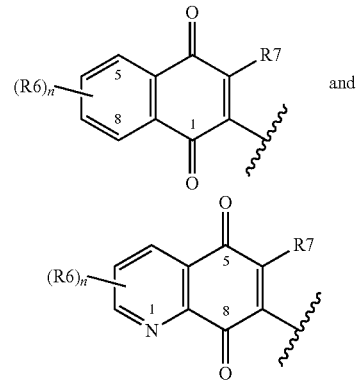

their preparation and their application as antimalarial agents

10 Claims, 13 Drawing Sheets

(51) Int. Cl.

| | |
|---|---|
| *C07C 205/46* | (2006.01) |
| *C07C 225/24* | (2006.01) |
| *C07C 255/29* | (2006.01) |
| *C07C 255/56* | (2006.01) |
| *C07C 271/28* | (2006.01) |
| *C07D 295/096* | (2006.01) |
| *C07D 295/116* | (2006.01) |
| *C07D 265/30* | (2006.01) |
| *C07D 241/04* | (2006.01) |
| *C07D 215/16* | (2006.01) |

(56) References Cited

OTHER PUBLICATIONS

Sudhanshu Saxena, Neerja Pant, D. C. Jain, and R. S. Bhakuni, Antimalarial agents from plant sources, Current Science, vol. 85, No. 9, Nov. 10, 2003.*

Waske Etal: "Photoacylations of 2-substituted 1,4-naphthoquinones: a concise access to biologically active quinonoid compounds", Tetrahedron Letters, Feb. 20, 2006, pp. 1329-1332, vol. 47, No. 8, Elsevier, Amsterdam, XP005254914.

Ogihara Ketal: "Preparation of Naphthoquinone Derivatives From Plumbagin and Their Ichtyotoxicity", Chemical and Pharmaceutical Bulletin, Jan. 1, 1997, pp. 437-445, vol. 45, No. 3, Pharmaceutical Society of Japan, Tokyo, XP000910182.

Howland, John L.: "Inhibition of mitochondrial succinate oxidation by alkyl hydroxy naphthoquinones", Biochimica Et Biophysica Acta, 1965, pp. 205-213, vol. 105, No. 2, XP008093702.

Bauer, Holger et al: "A Fluoro Analogue of the Menadione Derivative 6-[2'-(3' Methyl)-1',4-'naphthoquinolyl] hexanoic Acid Is a Suicide Substrate of Glutathione Reductase. Crystal Structure of the Alkylated Human Enzyme", Journal of the American Chemical Society, 2006, pp. 10784-10794, vol. 128 No. 33, XP002486600.

Friebolin Wolfgang et al: "Antimalarial dual drugs based on potent inhibitors of glutathione reductase from Plasmodium falciparum", Journal of Medicinal Chemistry Mar. 13, 2008, Feb. 9, 2008, pp. 1260-1277, vol. 51, No. 5, XP002486601.

European Search Report, dated Jul. 14, 2008, in European Application No. 08 29 0278.

Anstey et al., "Elevated levels of methaemoglobin in Tanzanian Children with severe and uncomplicated malaria", Transactions of the Royal Society of Tropical Medicine and Hygiene, 1996, vol. 90, pp. 147-151.

Bauer et al., "A Fluoro Analogue of the Menadione Derivative M5 is a Suicide Substrate of Human Glutathione Reductase. Crystal Struture of the Alkylated Enzyme", Supporting Information, Fluorine-Based Suicide Substrate of Glutathione Reductase, pp. S1-S12.

Bernadou et al., "Biomimetic Chemical Catalysts in the Oxidative Activation of Drugs", Adv. Synth. Catal., 2004, vol. 346, pp. 171-184.

Biot et al., "5-Substituted Tetrazoles as Bioisosteres of Carboxylic Acids. Bioisosterism and Mechanistic Studies on Glutathione Reductase Inhibitors as Antimalarials", Journal of Medicinal Chemistry, 2004, vol. 47, No. 24, pp. 5972-5983.

Cohen et al., "Complex Formation between Chloroquine and Ferrihaemic Acid in vitro, and its effect on the Antimalarial Action of Chloroquine", May 23, 1964, vol. 202, pp. 805-806.

Davioud-Charvet et al., "A Prodrug Form of a Plasmodium falciparum Glutathione Reductase Inhibitor Conjugated with a 4-Anilinoquinoline", Journal of Medicine Chemistry, 2001, vol. 44, No. 24, pp. 4268-4276.

Dorn et al., "Malarial haemozoin/β-haematin supports haem polymerization in the absence of protein", Nature, 1995, vol. 374, pp. 269-271.

Egan, Timothy J., "Interactions of quinoline antimalarials with hematin in solution", Journal of Inorganic Biochemistry, 2006, vol. 100, pp. 916-926.

Kanzok et al., "Substitution of the Thioredoxin System for Glutathione Reductase in Drosophila melanogaster", Sciene, 2001, vol. 291, pp. 643-646.

Krauth-Siegel et al., "Dithiol Proteins as Guardians of the Intracellular Redox Milieu in Parasites: Old and New Drug Targets in Trypanosomes and Malaria-Causing Plasmodia", Angew. Chem. Int. Ed., 2005, vol. 44, pp. 690-715.

Meierjohann et al., "Regulation of intracellular glutathione levels in erythrocytes infected with chloroquine-sensitive and chloroquine-resistant Plasmodium falciparum", Biochem. J., 2002, vol. 368, pp. 761-768.

Monti et al., "A Novel Endogenous Antimalarial: Fe(II)-Protoporphyrin IXα (Heme) Inhibits Hematin Polymerization to β-Hematin (Malaria Pigment) and Kills Malaria Parasites", Biochemistry, 1999, vol. 38, pp. 8858-8863.

Sarma et al., "Glutathione Reductase of the Malarial Parasite Plasmodium falciparum: Crystal Structure and Inhibitor Development", J. Mol. Biol., 2003, vol. 328, pp. 893-907.

Schirmer et al., "Disulfide-Reductase Inhibitors as Chemotherapeutic Agents: The Design of Drugs for Trypanosomiasis and Malaria", Angew. Chem. Int. Ed. Engl., 1995, vol. 34, pp. 141-154.

Vippagunta et al., "Characterization of chloroquine-hematin μ-oxo dimer binding by isothermal titration calorimetry", Biochimica et Biophysica Acta, 2000, vol. 1475, pp. 133-140.

Zarchin et al., "Digestion of the Host Erythrocyte by Malaria Parasites is the Primary Target for Quinoline-Containing Antimalarials", Biochemical Pharmacologym, 1986, vol. 35, No. 14, pp. 2435-2442.

* cited by examiner

Structures of the benzyl series (1)

P_TM21

P_TM24 = HB67

P_TM26

P_TM29

P_TM30

P_TM31

P_TM32

P_TM36

P_TM37

P_TM41

P_TM43

P_TM45

P_TM50

P_TM54

P_TM56

P_TM57

P_TM58

P_TM59

Structures of the benzyl-series (2)

P_TM60

P_TM61

P_TM62

P_TM42

P_TM81

P_TM63

P_TM66

P_TM67

P_TM69

P_TM53

P_TM91

P_TM96

P_TM97

P_TM98

P_TM99

P_TM100

P_TM101

P_TM102

Structures of the benzyl-series (3)

P_TM87          P_TM103

Structures of the Benzoyl series

P_TM25　　　　　　P_TM27　　　　　　P_TM33

P_TM38　　　　　　P_TM34　　　　　　P_TM35

P_TM39　　　　　　P_TM40　　　　　　P_TM46

P_TM48　　　　　　P_TM28　　　　　　P_TM47

P_TM22　　　　　　P_TM51

Structures of precursors and biometabolites

IC$_{50}$ Values of Benzyl- and Benzoyl-Substituted Derivatives of Menadione as Inhibitors of *P. falciparum* and Human Glutathione Reductases.

| | | IC$_{50}$ (µM) | |
|---|---|---|---|
| | Compound | in *P. falciparum* GR assay[a] | in human GR assay[a] |
| Benzyl-series | P_TM24 = HB67 | > 10[c,d] (nd)[e] | 1.0[c] (2.3)[e] |
| | P_TM26 | 7.8 | 3.3 |
| | P_TM30 | 25 | 1.5 |
| | P_TM31 | 17 | 4.5 |
| | P_TM29 | > 50 | 1.6 |
| | P_TM63 | 9 | 12 |
| | P_TM36 | 8.2 | 8.6 |
| Benzoyl-series | P_TM22 | 1.1 | 0.7 |
| | P_TM27 | 1.5 | 1.2 |
| | P_TM25 | 1.2 | 0.3 |
| | P_TM34 | 1.9 | 1.5 |
| | P_TM33 | 6.3 | 0.7 |
| | P_TM28 | n.d. | 2.0 |
| | P_TM40 | 0.8 | 0.4 |
| | P_TM47 | 2.5 | 0.75 |
| Other cpnds | menadione[b] | 42.0 | 27.5 |
| | P_TM23 | 4.5 | 1.3 |

FIGURE 3

Glutathione Reductase-Catalyzed Naphthoquinone Reductase Activity

|  | Compound | Naphthoquinone Reductase Activity of PfGR | | |
|---|---|---|---|---|
|  |  | $K_M$ (µM) | $k_{cat}$ (min$^{-1}$) | $k_{cat} / K_M$ (mM$^{-1}$ s$^{-1}$) |
| Benzyl-series | P_TM26 | 26 | 2.53 | 1.62 |
| | P_TM36 | 87 | 4.09 | 0.78 |
| | P_TM63 | 96.5 | 198 | 34.2 |
| | P_TM24 = HB67 | n.a.* | n.a.* | n.a.* |
| Benzoyl-series | P_TM27 | 56.1 | 16.7 | 4.96 |
| | P_TM25 | 6.1 | 2.31 | 6.31 |
| | P_TM39 | 84.2 | 26.6 | 5.26 |
| | P_TM40 | 18 | 8.38 | 7.76 |
| | P_TM47 | 3.07 | 2.3 | 12.5 |
| | P_TM34 | 38.4 | 6.6 | 2.86 |
| | P_TM33 | 42.4 | 3.36 | 1.32 |
| Other cpnds | Menadione | 82.2 | 9.6 | 1.99 |
| | P_TM23 | 8.5 | 2.17 | 4.25 |

Methemoglobin Redox-cycling activity in the presence of the benzoyl derivative P_TM25

Figure 5

IC$_{50}$ Values of Menadione Derivatives as Cytotoxic Agents Against Malarial Parasites (Dd2, 3D7, K1, Pf-GHA) and Human Cells (KB, MRC-5) *in vitro*.

| Compound | Dd2 IC$_{50}$ (nM) | IC$_{50}$ (nM) | 3D7 IC$_{50}$ (μM) | K1 IC$_{50}$ (μM) | Tox IC$_{50}$ (μM) | Pf-GHA IC$_{50}$ (μM) | Tox MRC-5 (μM) |
|---|---|---|---|---|---|---|---|
| P_TM21 | 791 | | 0.27$^g$ | 0.10$^g$ | 45.5$^g$ | 3.00 | > 32.00 |
| P_TM22 | >1μM | | > 30$^g$ | 13.28$^g$ | 183.41$^g$ | 7.00 | > 32.00 |
| P_TM23 | 634 | | | | | | |
| P_TM24 = HB67 | 54 | 54 | n.d. 0.026$^h$ | 0.04$^a$ 0.029$^h$ | 189.5$^a$ 156.65$^h$ | 4.00 | > 32.00 |
| P_TM25 | >1μM | | 1.02$^g$ | 2.96$^g$ | 206.49$^g$ | > 32.00 | > 32.00 |
| P_TM26 | 65 | 66 | 0.2$^g$ | 0.1$^g$ | 62$^g$ | 3.00 | 12.00 |
| P_TM27 | >1μM | | 2.49$^a$ | 8.45$^a$ | 255.21$^a$ | > 32.00 | > 32.00 |
| P_TM28 | >1μM | | 0.44$^a$ | 10.97$^a$ | 211.51$^a$ | > 32.00 | > 32.00 |
| P_TM29 | 30 | 28 | 0.002$^a$ | 0.16$^a$ | 80.26$^a$ | 1.00 | > 32.00 |
| P_TM30 | 65 | 34 | 0.003$^a$ | 0.11$^a$ | 8.68$^a$ | 1.00 | > 32.00 |
| P_TM31 | 95 | 85 | 0.041$^a$ | 0.46$^a$ | 113.66$^a$ | 16.00 | > 32.00 |
| P_TM32 | 88 | 110 | 0.35$^a$ | 1.12$^a$ | 186.48$^a$ | 11.00 | > 32.00 |
| P_TM33 | >1μM | | 1.90$^a$ | 1.70$^a$ | 123.81$^a$ | 3.00 | > 32.00 |
| P_TM34 | >1μM | | 1.67$^a$ | 3.86$^a$ | 32.42$^a$ | > 32.00 | > 32.00 |
| P_TM35 | >1μM | | 2.78$^c$ | 5.50$^a$ | 58.69$^a$ | > 32.00 | > 32.00 |
| P_TM36 | 58 | 64 | 0.36$^a$ | 0.40$^a$ | 224.9$^a$ | 4.00 | > 32.00 |
| P_TM37 | 46 | 54 | 0.12$^a$ | 0.19$^a$ | 58.6$^a$ | > 37.00 | > 32.00 |
| P_TM38 | >1μM | | 1.14$^a$ | 3.17$^a$ | 138.07$^a$ | 4.00 | > 32.00 |
| P_TM39 | >1μM | | > 30$^c$ | | | 5.00 | > 32.00 |
| P_TM40 | 103 | | 1.03$^c$ | | | 15.00 | > 32.00 |
| P_TM41 | 48 | 46 | n.d. | 7.79 | 222.74 | 0.87 | > 32.00 |
| P_TM42 | 190 | | 0.006$^a$ | 0.35$^a$ | 7.92$^a$ | 0.89 | > 32.00 |
| P_TM43 | 80 | 74 | 0.0005$^a$ | 0.005$^a$ | 45.71$^a$ | 11.00 | 10.00 |
| P_TM45 | 42 | 43 | | | | 12.00 | > 32.00 |
| P_TM46 | >1μM | | | | | 4.00 | > 32.00 |
| P_TM47 | >1μM | | | | | > 32.00 | > 32.00 |
| P_TM48 | >1μM | | | | | 12.00 | > 32.00 |
| P_TM50 | >1μM | | 2.3$^f$ | 5.9$^f$ | 254.8$^f$ | > 32.00 | > 32.00 |
| P_TM51 | >1μM | | | | | > 32.00 | > 32.00 |
| P_TM53 | 552 | | | | | > 32.00 | > 32.00 |
| P_TM54 | 274 | | | | | 8.00 | > 64.00 |
| P_TM56 | 111 | | | | | 9.00 | > 64.00 |
| P_TM57 | 55 | 42 | | | | < 0.25 | > 64.00 |
| P_TM58 | 21 | 51 | | | | 2.00 | > 64.00 |
| P_TM59 | 49 | 168 | | | | 2.00 | > 64.00 |
| P_TM60 | 29 | 58 | | | | > 64.00 | > 64.00 |
| P_TM61 | 70 | 230 | | | | > 64.00 | > 64.00 |
| P_TM62 | >1μM | | | | | 9.00 | > 64.00 |
| P_TM63 | >1μM | | | | | 8.00 | > 64.00 |

| Compound | Dd2 IC$_{50}$ (nM) | Dd2 IC$_{50}$ (nM) | 3D7 IC$_{50}$ (µM) | K1 IC$_{50}$ (µM) | Tox IC$_{50}$ (µM) | Pf-GHA IC$_{50}$ (µM) | Tox MRC-5 (µM) |
|---|---|---|---|---|---|---|---|
| P_TM64 | 262 | | | | | 6.35 | 33.01 |
| P_TM65 | 417 | | | | | 7.81 | >64.00 |

Figure 5, continued

| Compound | Dd2 IC$_{50}$ (nM) | Dd2 IC$_{50}$ (nM) | 3D7 IC$_{50}$ (µM) | K1 IC$_{50}$ (µM) | Tox IC$_{50}$ (µM) | Pf-GHA IC$_{50}$ (µM) | Tox MRC-5 (µM) |
|---|---|---|---|---|---|---|---|
| P_TM66 | 485 | | | | | 1.49 | >64.00 |
| P_TM67 | 474 | | | | | 1.85 | >64.00 |
| P_TM69 | 223 | | | | | 2.31 | >64.00 |
| P_TM72 | 218 | | | | | 1.95 | 57.20 |
| P_TM76 | >1µM | | | | | 53.98 | 43.85 |
| P_TM77 | >1µM | | | | | >64.00 | >64.00 |
| P_TM78 | >1µM | | | | | >64.00 | >64.00 |
| P_TM79 | >1µM | | | | | 2.31 | >64.00 |
| P_TM80 | >1µM | | | | | - | - |
| P_TM81 | >1µM | | | | | <0.25 | 17.80 |
| P_TM82 | >1µM | | | | | - | - |
| P_TM87 | 369 | | | | | <0.25 | 38.05 |
| Atovaquone | <0.1 | | | | | 0.31 | >64.00 |
| Chloroquine | 291 | | | | | <0.25 | 51.54 |

Figure 6 : IC$_{50}$ and IC$_{90}$ values against various *P. falciparum* strains

Figure 7: Reduction of Parasitemia in *Plasmodium berghei* ANKA-Infected CD1 Mice.

| Compound | Dose | % reduction i.p. | % reduction p.o. |
|---|---|---|---|
| Untreated control | - | 0 | 0 |
| Chloroquine | 10 mg/kg. x4 | 94.9 | 98.8 |
| P_TM24(HB67) | 30 mg/kg x4 | n.d. | 0 |
| P_TM24(HB67) | 50 mg/kg x4 | 35.6* | 0.8 |
| P_TM37(BJ323) | 30 mg/kg x4 | 42.4 | 10.4 |
| P_TM43 (BJ321) | 30 mg/kg x4 | 43.4 | 34.9 |
| P_TM31 | 30 mg/kg x4 | 24.4 | n.d. |
| P_TM36 (BJ319) | 30 mg/kg x4 | 28.4 | n.d. |
| P_TM29 | 30 mg/kg x4 | 20.7 | n.d. |

Figure 8: *In vivo* Antimalarial Activity in *P. berghei*-Infected Mice

| Compound | Treatment | Animals | % Parasitaemia (dpi) | | | | % Suppression (dpi) | | | | Health status |
|---|---|---|---|---|---|---|---|---|---|---|---|
| | | | 4 | 7 | 11 | 14 | 4 | 7 | 11 | 14 | |
| Untreated control | - | 5 | 38.28 | 42.2 | 67.7 | 61.9 | 0 | 0 | 0 | 0 | From d4 p.i. onwards: poor appearance, tremor, body weight loss, rough hair, 4 animals died before d7 p.i. |
| CQ | 10 mg/kg | 5 | 5.24 | 9.8 | 32.1 | 56.2 | 86.30 | 76.84 | 52.66 | 9.23 | From d9 p.i. onwards: poor appearance, tremor, body weight loss, rough hair. One animal dies before d14 p.i. |
| P_TM41 | 50 mg/kg | 4 | nd | nd | nd | nd | nd | nd | nd | nd | From d7 p.i. onwards: poor appearance, all animals died before d11 p.i. |
| P_TM45 | 50 mg/kg | 4 | 9.37 | 7.7 | 41.9 | 69.3 | 75.52 | 81.79 | 38.12 | -11.97 | From d7 p.i. onwards: poor appearance (intermittent), one animal died before d14 p.i. |
| P_TM57 | 50 mg/kg | 4 | 9.19 | 17.3 | 38.8 | 63.1 | 75.99 | 58.90 | 42.69 | -1.87 | From d8 p.i. onwards: poor appearance (intermittent), 3 animals died before d14 p.i. | ns
1,4-NAPHTHOQUINONES DERIVATIVES AND THERAPEUTIC USE THEREOF

FIELD OF THE INVENTION

The present invention relates to derivatives of 1,4-naphthoquinones, their preparation and their application in therapeutics.

BACKGROUND OF THE INVENTION

Due to spreading resistances, new drugs against malaria are continuously needed in poor countries where severe malaria kills millions of children every year. Ethical drugs must be cheap and therefore they should be easy to synthesize if they are not readily available as chemicals on the market.

*Plasmodium* parasites are exposed to elevated fluxes of reactive oxygen species during the life cycle in the human host and therefore high activities of intracellular antioxidant systems are needed. The most important antioxidative system consists of thiols which are regenerated by disulfide reductases; these include three validated drug targets, the glutathione reductases (GR) of the malarial parasite *Plasmodium falciparum* and of human erythrocytes as well as the thioredoxin reductase of *P. falciparum* (Schirmer et al, *Angew. Chem. Int. Ed. Engl.* 1995, 34, 141-54; Krauth-Siegel et al, Angewandte Chemie International Edition (2005), 44 (5), 690-715). One validated target against the malarial parasite *Plasmodium falciparum* is the enzyme glutathione reductase which reduces glutathione disulfide to its thiol form glutathione on the expense of NADPH. Glutathione is implicated in the development of chloroquine resistance: an elevation of the glutathione content in *P. falciparum* leads to increased resistance to chloroquine, while glutathione depletion in resistant strains restores sensitivity to chloroquine (Meierjohan et al, *Biochem. J.* 2002, 368, 761-768). High intracellular glutathione levels depend inter alia on the efficient reduction of glutathione disulfide by GR and by reduced thioredoxin (Kanzok et al, *Science* 2001, 291, 643-646). The contribution to the reversal of drug resistance by GR inhibitors is currently investigated for the commonly used antimalarial drug chloroquine in clinical trials (Sarma et al., *J. Mol. Biol.* 2003, 328, 893-907). Derivatives of menadione were shown to be potent inhibitors both of human and *Plasmodium falciparum* glutathione reductases acting in the low micromolar range (Davioud-Charvet et al, *J. Med. Chem.* 2001, 44, 4268-4276; Biot et al, *J. Med. Chem.* 47, 5972-5983; Bauer et al, *J. Am. Chem. Soc.* 2006, 128, 10784-10794).

The malarial parasite *Plasmodium falciparum* digests a large amount of its host cell hemoglobin during its erythrocytic cycle as source of essential nutrients (Zarchin et al, *Biochem. Pharmacol.* 1986, 35, 2435-2442). The digestion is a complex process that involves several proteases and takes place in the food vacuole of the parasite leading to the formation of iron III ferroprotoporphyrin (FPIX) (Goldberg et al, Parasitol. Today, 1992, 8, 280-283) as toxic byproduct for the parasite. Due to the toxicity of FPIX the parasites have developed a detoxification process in which FPIX (Fe3+) (hematin) is polymerized forming inert crystals of hemozoin or malaria pigment (Dorn et al, Nature 1995, 374, 269-271). FPIX (Fe2+) is an inhibitor of hematin polymerization (Monti et al, *Biochemistry* 1999, 38, 8858-8863). Early observations indicated that free FPIX (Fe3+) is able to form complexes with aromatic compounds bearing nitrogen, e.g. pyridines, 4-aminoquinolines (Cohen et al, *Nature* 1964, 202, 805-806; Egan et al, *J. Inorg. Biochem.* 2006, 100, 916-926) and it is now well established that 4-aminoquinolines can form µ-oxodimers with FPIX thus preventing the formation of hemozoin. Consequently an accumulation of free heme in the food vacuole is responsible for killing the parasite (Vippagunta et al, *Biomed. Biochim. Acta* 2000, 1475, 133-140). In the presence of reactive oxygen species iron-porphyrin complexes (e.g. free heme) are catalysts for oxidation reactions. Released in large quantities in the food vacuole of the parasite they are thought to strongly influence the activity of a drug under the specific acidic conditions of the malarial food vacuole. Drug metabolites can be more active than its precursor (pro-drug effect) or toxic (Bernadou et al, *Adv. Synth. Catal.* 2004, 346, 171-184).

The reduction of methemoglobin($Fe^{3+}$) into hemoglobin ($Fe^{2+}$) is of great importance in the treatment of malaria. Since the malarial parasite is much more capable of using methemoglobin as nutrient and digests methemoblobin faster than hemoglobin, the reduction of methemoglobin can be used to slow down the parasite's methemoglobin digestion by reducing its concentration. A second reason to target the reduction of methemoglobin is that methemoglobin, the ferric form of hemoglobin, is not capable of oxygen transport. High levels of methemoglobin are found during *Plasmodium vivax* infections (Anstey et al, *Trans. R. Soc. Trop. Med. Hyg.* 1996, 90, 147-151). A reduced oxygen carrying capacity of blood due to anaemia is even worsened by reduction in oxygen carrying capacity from even a modest concentration of methemoglobin leading to an impaired supply of oxygen for the tissue; a specific situation observed in cerebral malaria.

Since the malarial parasite *Plasmodium falciparum* multiplies in human erythrocytes, most drugs are directed against this stage of the life cycle of the parasite. Due to increasing resistance of the parasite against standard drugs such as chloroquine, newly drugs are urgently required.

There is therefore still a need for compounds having efficiency against malaria, without their usual drawbacks. Furthermore, there is a need for anti-malarial drugs which are easy to formulate in pharmaceutical compositions.

SUMMARY OF THE INVENTION

Accordingly, this invention provides novel potent anti-malarial agents and methodology of treating malaria using novel potent anti-malarial agents. The invention also provides potent anti-malarial agents that are inhibitors of *P. falciparum* glutathione reductase and active against chloroquine-sensitive and resistant malarial strains.

The present invention relates to compounds of formula (I)

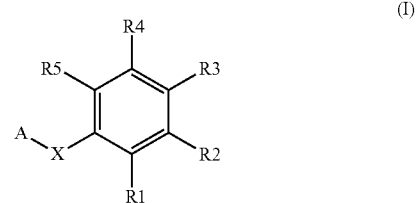

wherein
A is selected from the following rings:

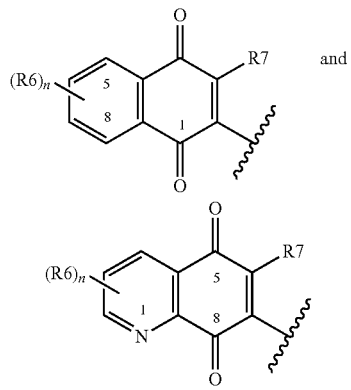

with each of R6, which may be in position 5, 6, 7, or 8 of the phenyl ring of the naphthoquinone or in position 2, 3, or 4 of the quinoline-5,8-dione, representing independently a hydrogen atom, a halogen atom, a hydroxy group, a linear or branched ($C_1$-$C_4$)alkyl group, a di- or tri-fluoromethyl group, a trifluoromethoxy group, a pentafluorosulfanyl group, n being an integer comprised between 0 and 4 and R7 representing a methyl group, X represents —C(O)— or —CHY— with Y selected from the group comprising hydrogen atom, hydroxy group, a linear or branched ($C_1$-$C_4$)alkyl group and ($C_3$-$C_6$)cycloalkyl group, R1, R2, R3, R4 and R5 represent each independently of the others:
a hydrogen atom,
a halogen atom,
a hydroxy group,
a linear or branched ($C_1$-$C_4$)alkyl group,
a trifluoromethyl group,
a difluoromethyl group,
a linear or branched ($C_1$-$C_4$)alkoxy group,
a trifluoromethoxy group,
a difluoromethoxy group,
a pentafluorosulfanyl group
—COOH,
—COO($C_1$-$C_4$)alkyl group,
—CONR8($CH_2$)$_m$CN, with R8 being a hydrogen atom or a linear or branched ($C_1$-$C_4$)alkyl group and m=1, 2 or 3,
—CSNR8($CH_2$)$_m$CN, with R8 being a hydrogen atom or a linear or branched ($C_1$-$C_4$)alkyl group m=1, 2 or 3,
—CONR8Het with R8 being a hydrogen atom or a linear or branched ($C_1$-$C_4$)alkyl group, Het representing a pyridine-2-yl group optionally substituted by an amino group in -6 or by a —$CONH_2$ group in -5,
—$NO_2$,
—CN,
—NR9R10 with R9 and R10 representing each independently a hydrogen atom, an amino protecting group selected from the group comprising Boc group and ($C_1$-$C_4$)alkyl group, or R9 and R10 forming with the nitrogen atom which bears them a cyclic group selected from the group comprising morpholine and piperazine groups said cyclic groups being optionally substituted, an aryl group optionally substituted by a ($C_1$-$C_4$)alkyl group, a —$NO_2$ group, a —COOR11 with R11 selected from a hydrogen atom and a linear or branched ($C_1$-$C_4$)alkyl group, a —NR12R13 with R12 and R13 independently selected from the group comprising a hydrogen atom and a linear or branched ($C_1$-$C_4$)alkyl group, a heterocyclic group selected from the group comprising morpholinyl group or piperazinyl group, each of said group being optionally substituted by one or several substituents selected from the group comprising a linear or branched ($C_1$-$C_4$)alkyl group, —$COOCH_2CH_3$, or a group

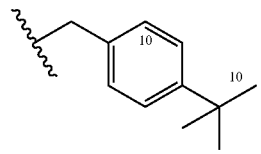 [SMILES: *Cc1ccc(C(C)(C)C)cc1]

and the pharmaceutically acceptable derivatives thereof,
with the proviso that the compounds of formula (I) are not selected from the group comprising

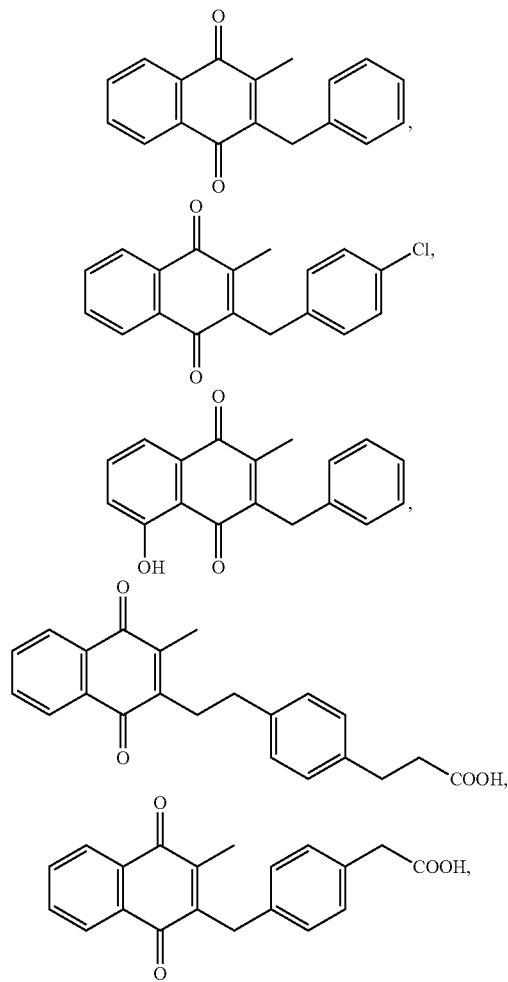

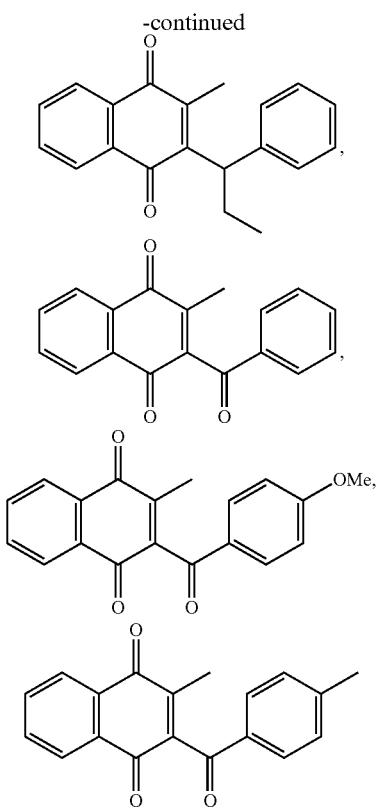

which are disclosed in U.S. Pat. No. 2,417,919, in *Tetrahedron Lett.* 2006, 47, 1329-1332 by P. Waske et al, in *Chem. Pharm. Bull.*, 1997, 45, 437-445 by Ogihara et al, in *Biochim. Biophys. Acta,* 1965, 105, 205-213 by Howland et al, in *J. Am. Chem. Soc.,* 2006, 128, 10784-10794 by Bauer et al, in *J. Med. Chem.,* 2008, 128, 10784-10794 by Friebolin et al and in *Tetrahedron* 1971, 27 (12), 2529-39 by K. Chandrasenan et al, respectively.

The term "alkyl" refers to a straight or branched chain, saturated hydrocarbon having the indicated number of carbon atoms. A ($C_1$-$C_4$) alkyl is meant to include but is not limited to methyl, ethyl, propyl, isopropyl, butyl, sec-butyl, tert-butyl. An alkyl group can be unsubstituted or optionally substituted with one or more substituents.

The term "alkoxy" refers to an —O-alkyl group having the indicated number of carbon atoms. A ($C_1$-$C_4$)alkoxy group includes —O-methyl, —O-ethyl, —O-propyl, —O-isopropyl, —O-butyl, —O-sec-butyl, —O-tert-butyl.

The term "aryl" refers to a 6- to 18-membered monocyclic, bicyclic, tricyclic, or polycyclic aromatic hydrocarbon ring system. Examples of an aryl group include phenyl, naphthyl, pyrenyl, anthracyl, quinolyl, and isoquinolyl. An aryl group can be unsubstituted or optionally substituted with one or more substituents as described herein below.

According to the present invention, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, hydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

In one embodiment, the compounds of formula (I) are those wherein

R1, R2, R4 and R5 represent each independently of the others a hydrogen atom, a halogen atom, a di- or trifluoromethyl group or a ($C_1$-$C_4$)alkoxy group, R3 represents
  a hydrogen atom,
  a halogen atom,
  a hydroxy group,
  a linear or branched ($C_1$-$C_4$)alkyl group,
  a trifluoromethyl group,
  a difluoromethyl group,
  a linear or branched ($C_1$-$C_4$)alkoxy group,
  a trifluoromethoxy group,
  a difluoromethoxy group,
  a pentafluorosulfanyl group
  —COOH,
  —COO($C_1$-$C_4$)alkyl group,
    —CONR8($CH_2$)$_m$CN, with R8 being a hydrogen atom or a linear or branched ($C_1$-$C_4$)alkyl group and m=1, 2 or 3,
    —CSNR8($CH_2$)$_m$CN, with R8 being a hydrogen atom or a linear or branched ($C_1$-$C_4$)alkyl group m=1, 2 or 3,
    —CONR8Het with R8 being a hydrogen atom or a linear or branched ($C_1$-$C_4$)alkyl group, Het representing a pyridine-2-yl group optionally substituted by an amino group in -6 or a —$CONH_2$ group in -5,
  —$NO_2$,
  —CN,
  —NR9R10 with R9 representing a hydrogen atom, or a ($C_1$-$C_4$)alkyl group and R10 representing a ($C_1$-$C_4$)alkyl group, or R9 and R10 forming with the nitrogen atom which bears them a

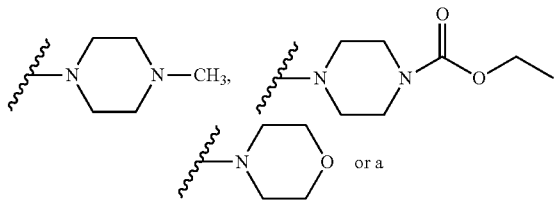

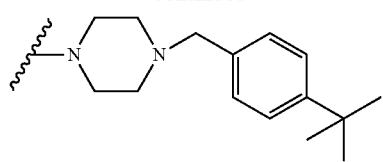

a phenyl group optionally substituted in para by a (C$_1$-C$_4$)alkyl group, a —NO$_2$ group, a —COOR11 with R11 selected from a hydrogen atom and a linear or branched (C$_1$-C$_4$)alkyl group, a —NR12R13 with R12 and R13 selected from the group comprising a hydrogen atom and a linear or branched (C$_1$-C$_4$)alkyl group.

a heterocyclic group selected from the group comprising morpholinyl group or piperazinyl group, each of said group being optionally substituted by one or several substituents selected from the group comprising a linear or branched (C$_1$-C$_4$)alkyl group, —COOCH$_2$CH$_3$, or a

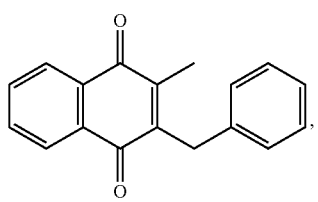

group and the pharmaceutically acceptable derivatives thereof, with the proviso that the compounds of formula (I) are not selected from the group comprising

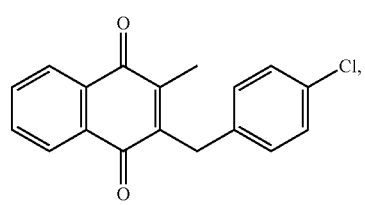

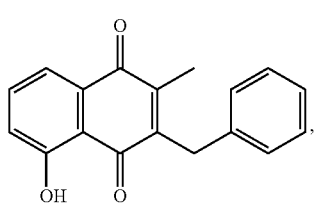

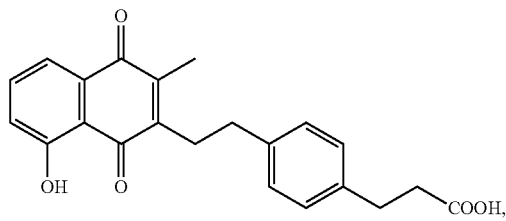

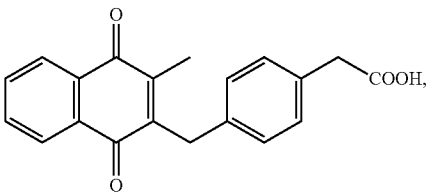

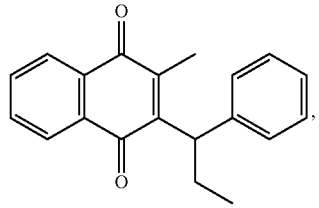

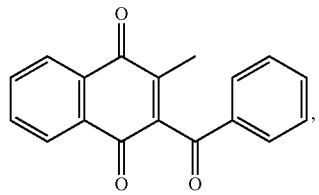

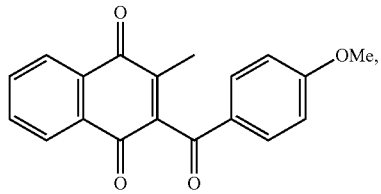

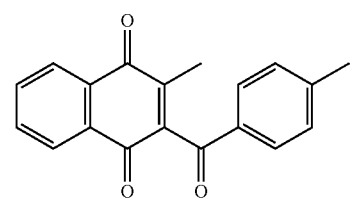 [SMILES: CC1=C(C(=O)c2ccc(C)cc2)C(=O)c2ccccc2C1=O]

In another embodiment, A is selected from the following rings:

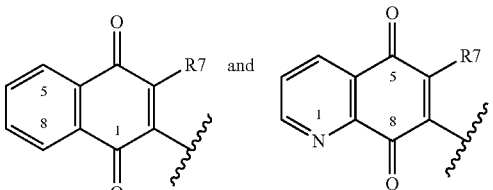

wherein R7 represents a methyl group.

In yet another embodiment X represents —C(O)— or —CH$_2$—.

In still another embodiment:

R1, R2, R3, R4, R5 represent each:
- a hydrogen atom,
- a halogen atom selected from the group comprising Br, Cl and F,
- a hydroxy group,
- a linear or branched $(C_1-C_4)$alkyl group selected from the group comprising methyl and t-butyl,
- a di- or trifluoromethyl group,
- a methoxy group,
- a trifluoromethoxy group,
- a pentafluorosulfanyl group
- —$NO_2$,
- —CN,
- —COOR14 with R14 representing hydrogen atom or methyl group,
- —CONH$(CH_2)_2$CN
- —NHBoc,
- a group selected from the group comprising

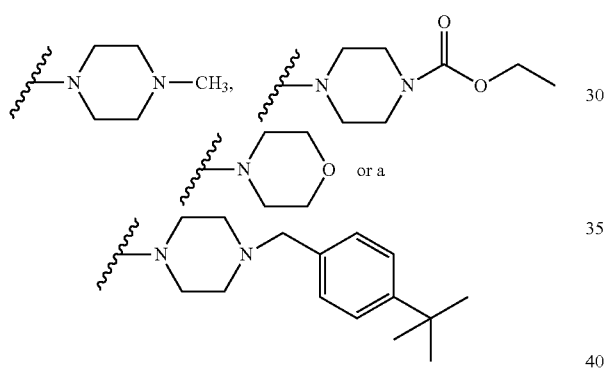

- a phenyl group substituted in para by a t-butyl group, —$NO_2$, —$N(CH_3)_2$, or —$NHC(CH_3)_3$.

In still another embodiment:

R1, R2, R3, R4 and R5 are each independently selected from the group comprising a hydrogen atom, a hydroxy group, a methoxy group, a di- or tri-fluoromethyl group and a trifluoromethoxy group, a pentafluorosulfanyl group, or an amino group and.

In yet another embodiment R1, R2, R3, R4 and R5 represent a fluorine atom, a di- or tri-fluoromethyl group, or a trifluoromethoxy group, a pentafluorosulfanyl group.

In another embodiment, the invention provides a process for preparing compounds of formula (I) wherein A represents:

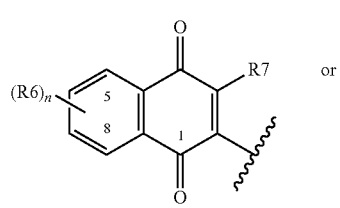

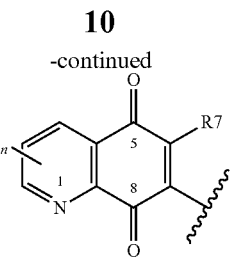

comprising the reaction of a compound of formula (IIa) or (IIb)

(IIa)

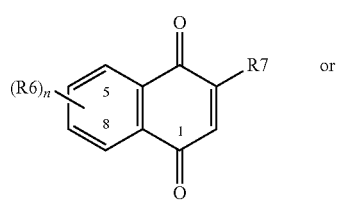

(IIb)

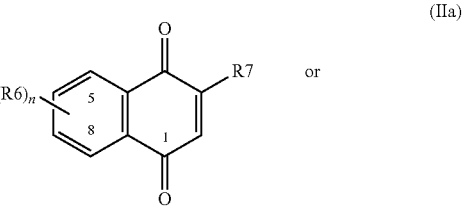

wherein each of R6, which may be in position 5, 6, 7, or 8 of the phenyl ring of the 1,4-naphthoquinone or in position 2, 3, or 4 of the quinoline-5,8-dione, represents independently a hydrogen atom, a halogen atom, an hydroxy group, a linear or branched $(C_1-C_4)$alkyl group, a di- or trifluoromethyl group, a trifluoromethoxy group, pentafluorosulfanyl group, n being an integer comprised between 0 and 4, and R7 represents a methyl group, with a phenyl acetic acid derivative of formula (III)

(III)

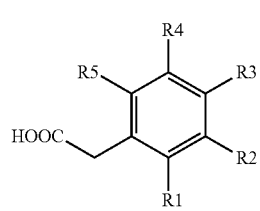

wherein
R1, R2, R3, R4 and R5 are as defined in claim 1,
to obtain respectively a compound of formula (Ia)

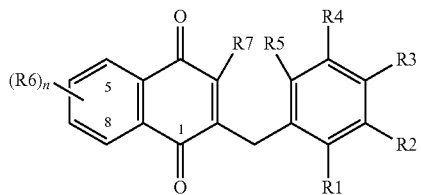

or of formula (Ib)

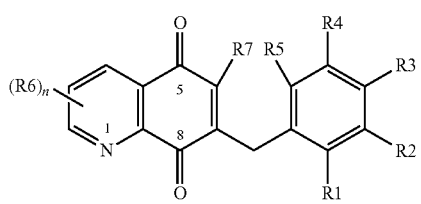

which may be treated in oxidative conditions to give respectively a compound of formula (Ic)

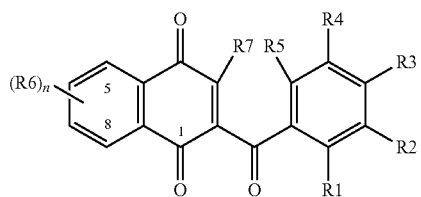

or a compound of formula (Id)

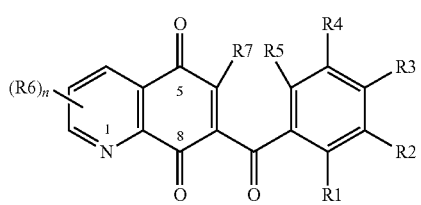

wherein R1, R2, R3, R4, R5, R6 and n are as defined above.

The invention also provides a process for preparing compounds of formula (Ia1, Ib1, Ic1, Id1, Ie and If) corresponding to compounds of formula (I) wherein A represents

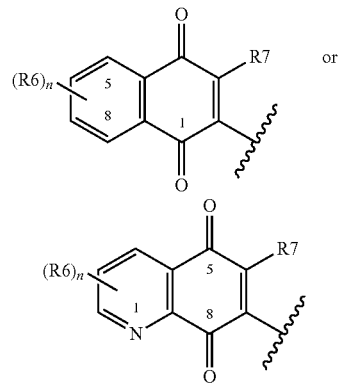

and X represents —CH$_2$—, or —C(O)—
comprising
a) the preparation of a compound of formula (IIc)

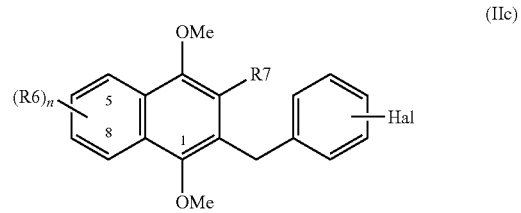

or of formula (IId)

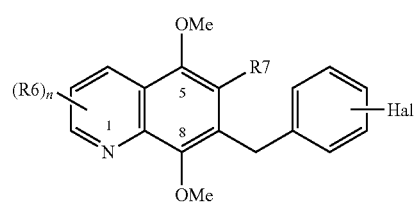

wherein
R6 which may be in position 5, 6, 7, or 8 of the phenyl ring of the 1,4-dimethoxynaphthalene or in position 2, 3, or 4 of the 5,8-dimethoxyquinoline, represents a hydrogen atom, a halogen atom, a hydroxy group, a linear or branched (C$_1$-C$_4$)alkyl group, a di- or tri-fluoromethyl group, a trifluoromethoxy group, a pentafluorosulfanyl group, and n being an integer comprised between 0 and 4,
R7 represents a methyl group and
Hal represents a chloro, a bromo or a iodo atom,
by reduction of the corresponding quinones followed by methylation of the dihydronaphthoquinones intermediates into the corresponding dimethoxynaphthalene of formula (IIc) or dimethoxyquinoline of formula (IId),
b) reaction of respectively one compound of formula (IIc) or (IId) with an amino compound of formula HNR9R10 with R9 and R10 representing each independently a hydrogen atom or a (C$_1$-C$_4$)alkyl group, with the proviso that R9 and R10 are not both a hydrogen atom, or R9 and R10 forming with the nitrogen atom which bears them a cyclic group selected from the group comprising morpholine and piperazine groups said cyclic groups being optionally substituted, in the presence of a palladium catalyst and of an appropriate palladium ligand, to obtain a compound of formula (Ie)

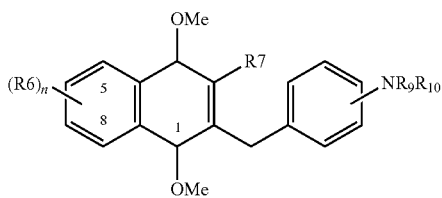
(Ie)

or of formula (If)

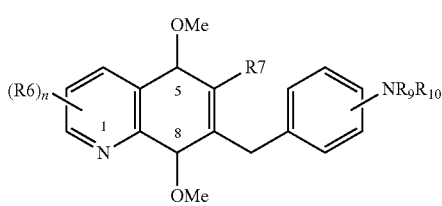
(If)

wherein R6, R7, R9 and R10 are as defined above, c) re-oxidation of the compound of formula (Ie) or (If) to give the final compounds of formula (Ia1) or (Ic1)

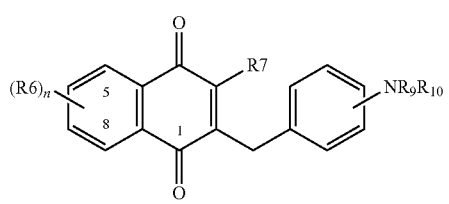
(Ia1)

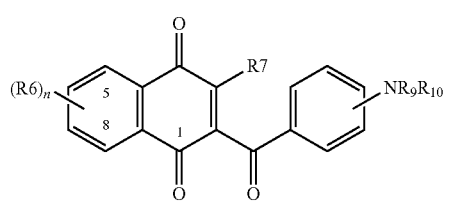
(Ic1)

or a compound of formula (Ib1) or (Id1)

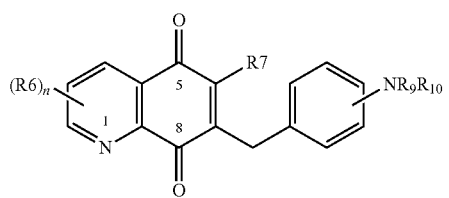
(Ib1)

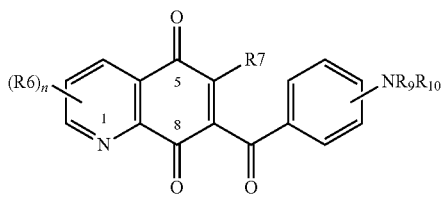
(Ib1)

The present invention also provides a process for preparing compounds of formula (I)

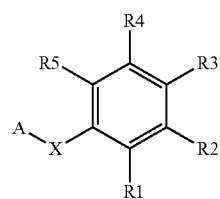
(I)

wherein

A is selected from the following rings:

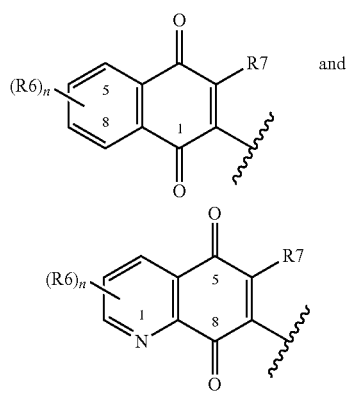

with each of R6, which may be in position 5, 6, 7, or 8 of the phenyl ring of the naphthoquinone or in position 2, 3, or 4 of the quinoline-5,8-dione, representing independently a hydrogen atom, a halogen atom, a hydroxy group, a linear or branched $(C_1-C_4)$alkyl group, a di- or tri-fluoromethyl group, a trifluoromethoxy group, a pentafluorosulfanyl group, n being an integer comprised between 0 and 4 and R7 representing a methyl group, one of R1, R2, R3, R4, R5 represents a phenyl-ring bearing in para position a tertbutyl group, —NO₂, —COOR11 with R11 being hydrogen atom or a linear or branched $(C_1-C_4)$alkyl group, or NMe₂ group, starting from the corresponding compound of formula (Ia) or (Ib) or (Ic) or (Id) wherein one of R1, R2, R3, R4 and R5 represents a halogen atom, the others being a hydrogen atom, X represents —C(O)— or —CHY— with Y selected from the group comprising hydrogen atom, hydroxy group, a linear or branched $(C_1-C_4)$alkyl group and $(C_3-C_6)$cycloalkyl group and with a boronic acid derivative of formula (IV)

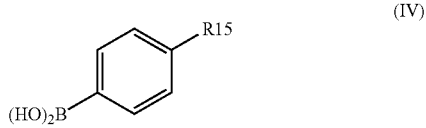

wherein R15 represents a tertbutyl group, —NO$_2$, —COOR11 with R11 being hydrogen atom or a linear or branched (C$_1$-C$_4$)alkyl group, or NMe$_2$ group in the presence of a palladium catalyst and of a base.

The present invention still provides compounds of formula (I) as a drug, especially as antimalarial agents.

In another embodiment the invention provides for the use of compounds of formula (I) in therapy or prophylaxis, with the proviso that the compounds of formula (I) are not

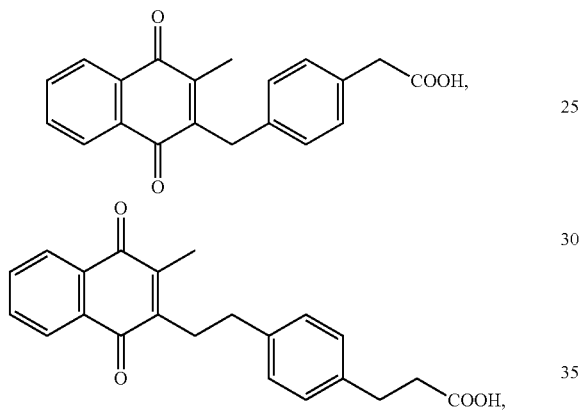

In accordance with this invention, the compounds of formula (I) or their pharmaceutically acceptable salts are useful in pharmaceutically acceptable compositions. The pharmaceutical compositions according to the invention comprise as active ingredient one or more of the compounds of formula (I) or its pharmaceutically acceptable salts, in combination with excipients and/or pharmaceutically acceptable diluents or carriers. Any conventional carrier material can be utilized. The carrier material can be an organic or inorganic inert carrier material, for example one that is suitable for oral administration. Suitable carriers include water, gelatin, gum arabic, lactose, starch, magnesium stearate, talc, vegetable oils, polyalkylene-glycols, glycerine and petroleum jelly. Furthermore, the pharmaceutical preparations may also contain other pharmaceutically active agents. Additional additives such as flavoring agents, preservatives, stabilizers, emulsifying agents, buffers and the like may be added in accordance with accepted practices of pharmaceutical compounding. The pharmaceutical preparations can be made up in any conventional form including a solid form for oral administration such as tablets, capsules, pills, powders, granules, and rectal suppositories. The pharmaceutical preparations may be sterilized and/or may contain adjuvants such as preservatives, stabilizers, wetting agents, emulsifiers, salts for varying the osmotic pressure and/or buffers.

The compounds of the invention can also be administered to a patient in accordance with the invention by topical (including transdermal, buccal or sublingual), or parenteral (including intraperitoneal, subcutaneous, intravenous, intradermal or intramuscular injection) routes.

The other active agents useful according to the invention may be one to three other antimalarial agents selected from the group comprising atovaquone, chloroquine, amodiaquine, mefloquine, artemisinin and the related peroxans from the pharmaceutical market like artesunate, arteether and artemether, menadione, methylene blue, proguanil, cycloguanil, chlorproguanil, pyrimethamine, primaquine, piperaquine, fosmidomycin, halofantrine, dapsone, trimethoprim, sulfamethoxazole, sulfadoxine, for a simultaneous, separated or sequential, or administration.

The invention also provides compounds of formula (I) including the compounds of formula (I) selected from the group comprising

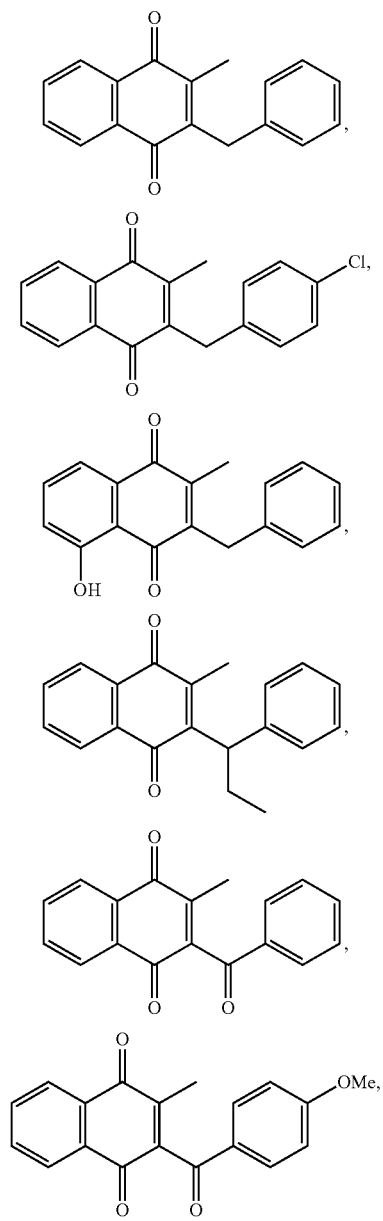

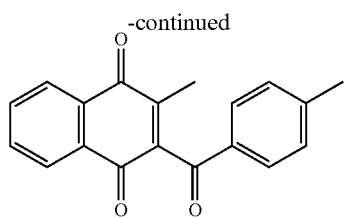

for the prevention and the treatment of malaria.

In one embodiment, the invention provides methods of inhibiting glutathione reductase in a parasite, comprising contacting said parasite with a pharmaceutical composition comprising a compound of the invention. In one embodiment, the parasite is a member of the *Plasmodium* genus. In another embodiment, the parasite is *Plasmodium falciparum*, or *Plasmodium vivax*.

In another embodiment, the invention provides methods of treating or preventing malaria, inhibiting glutathione reductase in a parasite, such as *Plasmodium falciparum* or *Plasmodium vivax*, in vitro or in vivo, or killing a *Plasmodium falciparum* or *Plasmodium vivax* parasite, wherein the pharmaceutical composition comprises a compound of formula (I).

Compounds of formula (II) corresponding to compounds of formula (I)

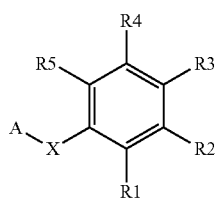

are new and are also part of the invention.
wherein
(A) represents

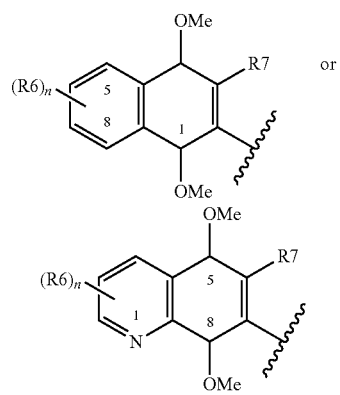

with R6 which may be in position 5, 6, 7, or 8 of the phenyl ring of the 1,4-dimethoxynaphthalene or in position 2, 3, or 4 of the 5,8-dimethoxyquinoline, represents a hydrogen atom, a halogen atom, a hydroxy group, a linear or branched ($C_1$-$C_4$) alkyl group, a di- or tri-fluoromethyl group, a trifluoromethoxy group and, a pentafluorosulfanyl group, n being an integer comprised between 0 and 4 and R7 representing a methyl group and X=$CH_2$, C(O) or —CHY— with Y selected from the group comprising hydrogen atom, hydroxy group, a linear or branched ($C_1$-$C_4$)alkyl group and ($C_3$-$C_6$)cycloalkyl group, R1, R2, R3, R4 and R5 represent each independently of the others:

a hydrogen atom, a halogen atom, a hydroxy group, a linear or branched ($C_1$-$C_4$)alkyl group, a trifluoromethyl group, a difluoromethyl group, a linear or branched ($C_1$-$C_4$)alkoxy group, a trifluoromethoxy group, a difluoromethoxy group, a pentafluorosulfanyl group

—COOH,

—COO($C_1$-$C_4$)alkyl group,

—CONR8($CH_2$)$_m$CN, with R8 being a hydrogen atom or a linear or branched ($C_1$-$C_4$)alkyl group and m=1, 2 or 3, —CSNR8($CH_2$)$_m$CN, with R8 being a hydrogen atom or a linear or branched ($C_1$-$C_4$)alkyl group m=1, 2 or 3, —CONR8Het with R8 being a hydrogen atom or a linear or branched ($C_1$-$C_4$)alkyl group, Het representing a pyridine-2-yl group optionally substituted by an amino group in -6 or by a —$CONH_2$ group in -5,

—$NO_2$,

—CN,

—NR9R10 with R9 and R10 representing each independently a hydrogen atom, an amino protecting group selected from the group comprising Boc group and ($C_1$-$C_4$)alkyl group, or R9 and R10 forming with the nitrogen atom which bears them a cyclic group selected from the group comprising morpholine and piperazine groups said cyclic groups being optionally substituted, an aryl group optionally substituted by a ($C_1$-$C_4$)alkyl group, a —$NO_2$ group, a —COOR11 with R11 selected from a hydrogen atom and a linear or branched ($C_1$-$C_4$)alkyl group, a —NR12R13 with R12 and R13 independently selected from the group comprising a hydrogen atom and a linear or branched ($C_1$-$C_4$)alkyl group, a heterocyclic group selected from the group comprising morpholinyl group or piperazinyl group, each of said group being optionally substituted by one or several substituents selected from the group comprising a linear or branched ($C_1$-$C_4$)alkyl group, —$COOCH_2CH_3$, or a group

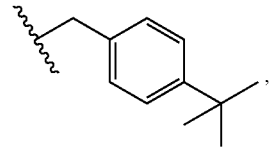 [SMILES: *Cc1ccc(C(C)(C)C)cc1]

with the proviso that the compounds of formula (II) are not selected from the group comprising

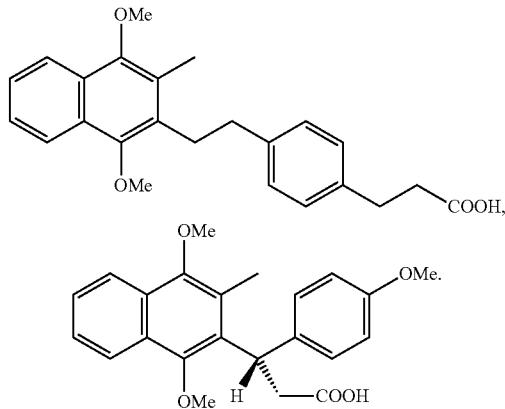

They may be used as intermediates for the synthesis of compounds of formula (I).

The following examples 1 to 16 are intended as illustrations of a few embodiments of the synthesis of compounds according to the invention. In these examples, melting points were determined on a Büchi melting point apparatus and were not corrected. $^1$H (300 MHz) and $^{13}$C (75 MHz) NMR spectra were recorded on a Bruker DRX-300 spectrometer; chemical shifts were expressed in ppm relative to TMS; multiplicity is indicated as s (singlet), d (doublet), t (triplet), q (quartet), sep (septet), m (multiplet), dd (doublet of a doublet), dt (doublet of a triplet) and td (triplet of a doublet). Intensities in the IR spectra are indicated as vs (very strong), s (strong), m (medium), w (weak), b (broad). Elemental analyses were carried out at the Mikroanalytisches Laboratorium der Chemischen Fakultät der Universität Heidelberg. EI-MS and CI-MS were recorded at facilities of the Institut für Organische Chemie der Universitat Heidelberg. Analytical TLC was carried out on pre-coated Sil G-25 UV$_{254}$ plates from Macherey&Nagel. Flash chromatography was performed using silica gel G60 (230-400 mesh) from Macherey&Nagel.

The following examples 17 to 22 are intended as illustrations of the pharmacological activity of the compounds according to the invention.

BRIEF DESCRIPTION OF THE DRAWINGS

FIG. 1a to 8 also illustrate the invention.

FIG. 1a to 1e illustrate the structure of some compounds synthesized according to the examples 1 to 16.

FIG. 2 illustrates the IC$_{50}$ values of benzyl-and benzoyl substituted derivatives of menadione according to the invention as inhibitors of P. falciparum and human glutathione reductase. [a] The values were determined at pH 6.9 and 25° C. in the presence of 1 mM GSSG according to example 17.[b] Data from Ref. (Bauer et al, J. Am. Chem. Soc. 2006, 128, 10784-10794).[c] in the presence of 5% DMSO.[d] Reprecipitation of the compound in the cuvette prevented IC$_{50}$ determination. [e] In the presence of 1% DMSO. nd: not yet determined.

FIG. 3 illustrates the glutathione reductase-catalyzed naphthoquinone reductase activity as measured as disclosed in example 18. * Precipitation of the compound was observed above 10 PM; at 10 μM there is no inhibition FIG. 4 illustrates the effect of P_TM25 on redox-cycling activity of methemoglobin(Fe$^{3+}$) into oxyhemoglobin(Fe$^{2+}$) in the presence of the NADPH/GR system measured at after 5 min (blue), 10 min (black), 20 min (green) and 30 min (red). MethHb =methemoglobin, OxyHb =Oxyhemoglobin. MB = Methylene Blue. The second plot (right) is a zoom of the spectra in the 350-450 nm area from the first plot (left).

FIG. 5 illustrates IC$_{50}$ values of menadione derivatives as cytotoxic agents against malarial parasites (Dd2, 3D7, K1, Pf-GHA) and human cells (KB, MRC-5) in vitro. a: CQ, Pf 3D7IC$_{50}$ 0.005 μM, K1 IC$_{50}$ 0.55 μM; b: CQ, Pf K1 IC$_{50}$ 0.01μM; c: CQ, Pf 3D7 IC$_{50}$ 0.0147 μM; d: CQ, Pf H IC$_{50}$ 0.217 μM; e: CQ, Pf K1 IC$_{50}$ 50.7-750.1 nM, Pf 3D7 IC$_{50}$ 3.8 nM; f: CQ, Pf K1 IC$_{50}$ 571.2 nM, Pf 3D7 IC50 11.5-15.3 nM; g: CQ, Pf 3D7 IC$_{50}$ 0.02-0.85 μM, Pf K1 IC$_{50}$ 0.01-0.02 μM; h: CQ, Pf 3D7 IC$_{50}$ 1.9-5.8 nM, Pf K1 IC$_{50}$ 57.7-750.1 nM; CQ =chloroquine.

FIG. 6 illustrates IC$_{50}$ and IC$_{90}$ values against various P. falciparum strains as measured according to example 21. CQ =chloroquine; DHA =dihydroartemisinin; FQ =ferroquine; LMF lumefantrine; MQ =mefloquine; MDAQ monodesethylamodiaquine; QN, =quinine.

FIG. 7 the reduction of parasitemia in Plasmodium Berghei ANKA-infected CD1 mice as measured according to example 22. * at 1.0 mg/kg, 3.0 mg/kg and 10.0 mg/kg chloroquine displayed a reduction of the parasitemia of 2.5%, 16.6% and 94.9%, respectively.

FIG. 8 illustrates the in vivo antimalarial activity in P. berghei-infected mice measured according to example 22.

EXAMPLE 1

Figure 1A:
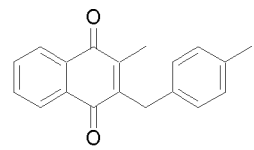
Figure 1A:
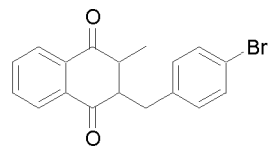
Figure 1A:
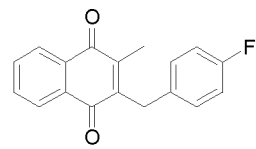
Figure 1A:
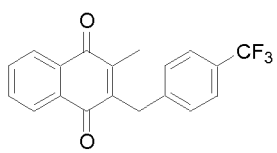
Figure 1A:
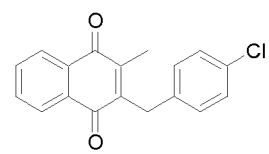
Figure 1A:
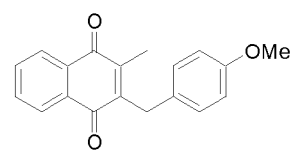
Figure 1A:
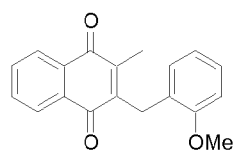
Figure 1A:
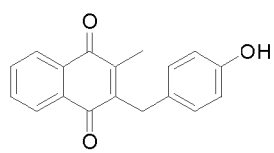
Figure 1A:
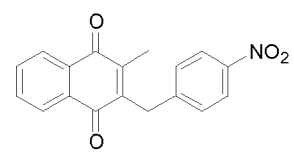
Figure 1A:
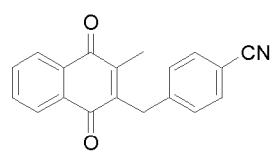
Figure 1A:
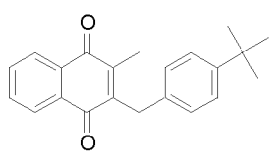
Figure 1A:
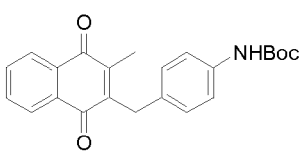
Figure 1A:
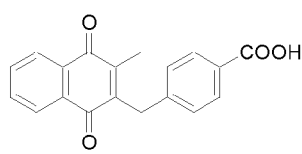
Figure 1A:
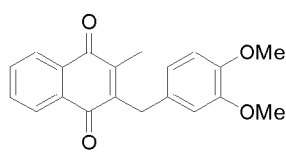
Figure 1A:
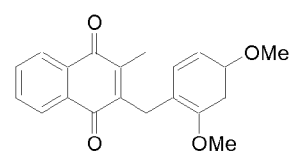
Figure 1A:
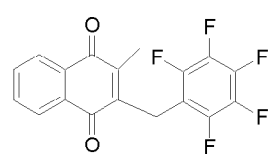
Figure 1A:
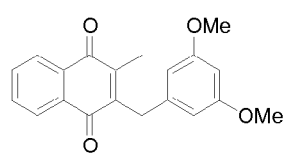
Figure 1A:
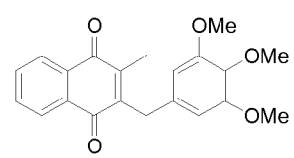
Figure 1B:
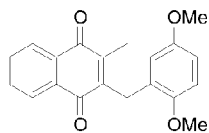
Figure 1B:
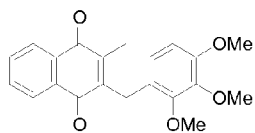
Figure 1B:
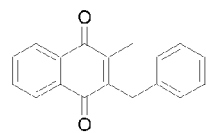
Figure 1B:
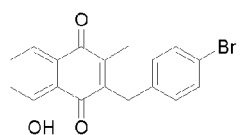
Figure 1B:
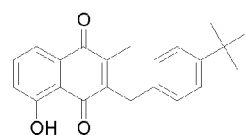
Figure 1B:
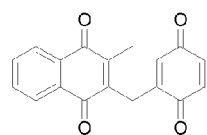
Figure 1B:
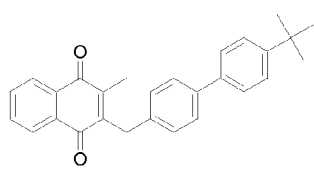
Figure 1B:
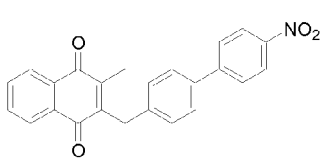
Figure 1B:
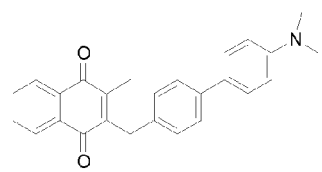
Figure 1B:
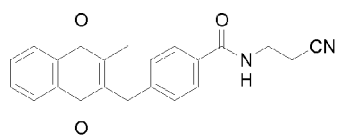
Figure 1B:
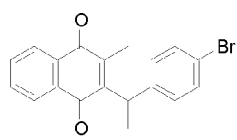
Figure 1B:
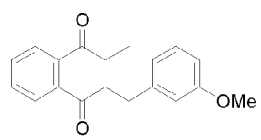
Figure 1B:
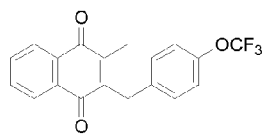
Figure 1B:
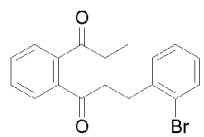
Figure 1B:
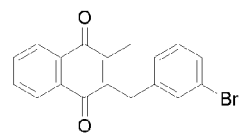
Figure 1B:
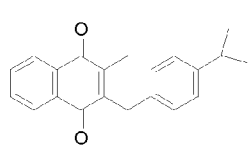
Figure 1B:
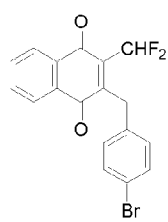
Figure 1B:
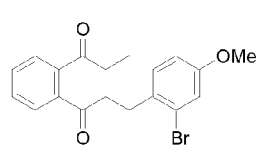
Figure 1C:
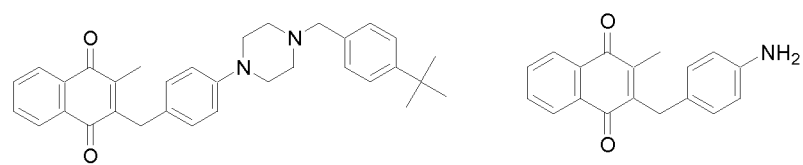
Figure 1D:
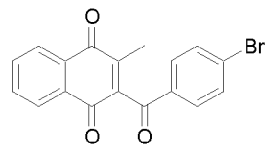
Figure 1D:
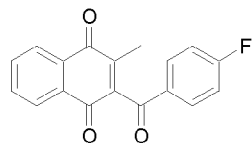
Figure 1D:
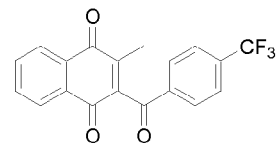
Figure 1D:
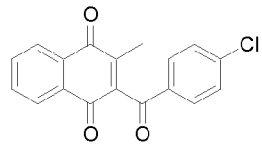
Figure 1D:
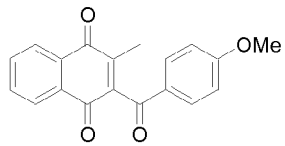
Figure 1D:
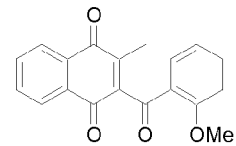
Figure 1D:
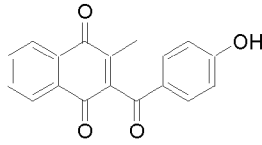
Figure 1D:
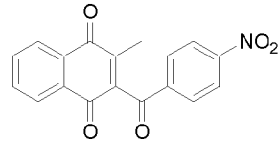
Figure 1D:
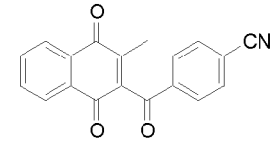
Figure 1D:
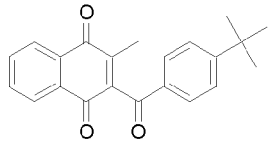
Figure 1D:
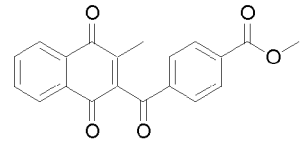
Figure 1D:
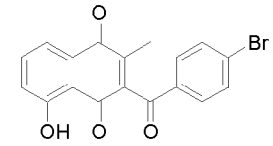
Figure 1D:
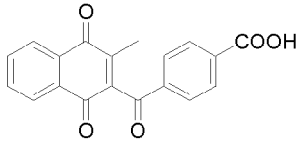
Figure 1D:
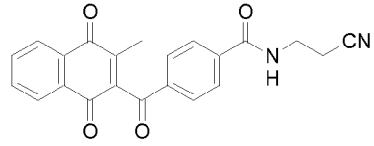
Figure 1E:
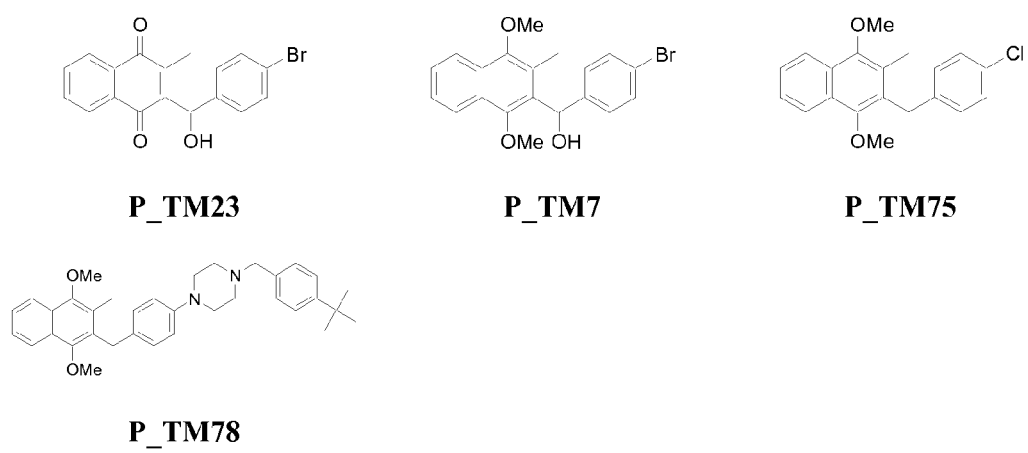

General Procedure for the Silver-Catalyzed Coupling Reactions of 1,4-Naphthoquinones with Carboxylic Acids A solution of menadione or plumbagin (5.81 mmol) and a phenylacetic acid derivative (11.58 mmol) in 52.5 mL acetonitrile and 17.5 mL water was heated to 85° C. AgNO$_3$ (90 mg, 0.58 mmol) was added. (NH$_4$)$_2$S$_2$O$_8$ (1.72 g, 7.54 mmol) in 15 mL acetonitrile and 5 mL water was added dropwise over a period of 45 minutes and then heated at reflux for two hours. The acetonitrile was removed in vacuo. The aqueous phase was extracted with dichloromethane (4×10 mL), dried over MgSO$_4$ and purified by flash-chromatography.

EXAMPLE 1.1

2-Methyl-3-(4-methyl-benzyl)-4a,8a-dihydro-[1,4] naphthoquinone (P_TM21)

As starting materials for the coupling reaction menadione and p-tolylacetic acid were used. Synthesis is realized according to the general procedure described in general procedure of example 1. After chromatography on silica gel (petroleum ether:ethylacetate=1:1, UV), 2.82 g (10.21 mmol, 77% yield) of P_TM21 were isolated as yellow solid.

Melting point: 225° C. decomposition. —$^1$H-NMR (300 MHz, CDCl$_3$): δ=8.04-8.05 (m, 2H), 7.64-7.70 (m, 2H), 7.08 (m, 4H), 3.98 (s, 2H), 2.27 (s, 3H), 2.23 (s, 3H). —$^{13}$C-NMR (75 MHz, CDCl$_3$): δ=185.42 (C$_q$), 184.66 (C$_q$), 145.53 (C$_q$), 144.20 (C$_q$), 135.97 (C$_q$), 134.94 (C$_q$), 133.42 (CH), 133.39 (CH), 132.12 (C$_q$), 132.06 (C$_q$), 129.31 (CH), 128.46 (CH), 126.44 (CH), 126.21 (CH), 31.99 (CH$_2$), 20.96 (CH$_3$), 13.23 (CH$_3$). —FAB MS (NBA, m/z (%)): 277.2 ([M+H]$^+$, 73), 261.1 (26), 212.1 (24). —IR (KBr): 3437 cm$^{-1}$ (b, m), 2923 (w), 1660 (vs), 1616 (w), 1595 (m), 1512 (m), 1377 (w), 1332

(w), 1295 (vs), 809 (w), 754 (m), 705 (m). —EA: obs. C, 82.44%; H, 5.84%, calcd. C, 82.58%; H, 5.84% for $C_{19}H_{16}O_2$.

EXAMPLE 1.2

2-Methyl-3-(4-bromo-benzyl)-4a,8a-dihydro-[1,4] naphthoquinone (P_TM24)

As starting materials for the coupling reaction menadione and 4-bromophenylacetic acid were used. Synthesis is realized according to the general procedure described in general procedure of example 1. After chromatography on silica gel (petroleum ether:$CH_2Cl_2$=1:1, UV), 3.10 g (9.12 mmol, 78% yield) of P_TM24 were isolated as yellow solid.

Melting point: 121-122° C. —$^1$H-NMR (300 MHz, $CDCl_3$): δ=8.03-8.10 (m, 2H), 7.66-7.71 (m, 2H), 7.36 (dt, $^3J$=8.46 Hz, $^4J$=1.95 Hz, 2H), 7.09 (d, $^3J$=8.53 Hz, 2H), 3.96 (s, 2H), 2.22 (s, 3H). —$^{13}$C-NMR (75 MHz, $CDCl_3$): δ=185.20 ($C_q$), 184.54 ($C_q$), 144.75 ($C_q$), 144.57 ($C_q$), 137.06 ($C_q$), 133.58 (CH), 132.08 ($C_q$), 131.94 ($C_q$), 131.71 (CH), 130.32 (CH), 126.50 (CH), 126.35 (CH), 120.31 ($C_q$), 31.93 ($CH_2$), 13.31 ($CH_3$). —EI MS (70 eV, m/z (%)): 340.1 ([M]$^+$, 13), 325.0 (100), 246.1 (63), 215.1 (41), 202.1 (49), 128.1 (72), 76.0 (74). —IR (KBr): 3449 cm$^{-1}$ (b, w), 3068 (w), 2962 (w), 1661 (vs), 1624 (m), 1618 (m), 1594 (s), 1486 (s), 1376 (m), 1332 (s), 1315 (s), 1294 (vs), 1071 (m), 1010 (s), 971 (w), 815 (m), 787 (s), 730 (m), 702 (m), 629 (w), 426 (w). —EA: obs. C, 63.02%; H, 3.84%, calcd. C, 63.36%; H, 3.84% for $C_{18}H_{13}BrO_2$.

EXAMPLE 1.3

2-Methyl-3-(4-fluoro-benzyl)-4a,8a-dihydro-[1,4] naphthoquinone (P_TM26)

As starting materials for the coupling reaction menadione and 4-fluorophenylacetic acid were used. Synthesis is realized according to the general procedure described in general procedure of example 1. After chromatography on silica gel (cyclohexane:ethyl acetate=3:1, UV), 5.34 g (19.1 mmol, 66% yield) of P_TM26 were isolated as yellow solid.

Melting point: 118-119° C. —$^1$H-NMR (300 MHz, $CDCl_3$): δ=8.05-8.08 (m, 2H), 7.65-7.71 (m, 2H), 7.15-7.20 (m, 2H), 6.93 (t, $^3J$=8.68 Hz, 2H), 3.97 (s, 2H), 2.22 (s, 3H). —$^{13}$C-NMR (75 MHz, $CDCl_3$): δ=185.31 ($C_q$), 184.63 ($C_q$), 161.52 ($^1J_{CF}$=244.8 Hz, CF), 145.15 ($C_q$), 144.40 ($C_q$), 133.72 ($C_q$), 133.67 ($C_q$), 133.57 ($C_q$), 131.02 (CH), 130.05 ($^3J_{CF}$=8.0 Hz, CH), 128.95 ($^4J_{CF}$=3.4 Hz, $C_q$), 126.50 (CH), 126.34 (CH), 115.45 ($^2J_{CF}$=21.4 Hz, CH), 31.69 ($CH_2$), 13.28 ($CH_3$). —EI MS (70 eV, m/z (%)): 280.1 ([M]$^+$, 21), 265.1 (100), 109.0 (53), 76.0 (24). —IR (KBr): 3428 cm$^{-1}$ (b, m), 1708 (w), 1684 (w), 1661 (vs), 1619 (w), 1597 (m), 1509 (vs), 1377 (w), 1295 (s), 1222 (m), 1158 (m), 824 (w), 705 (m). —EA: obs. C, 77.19%; H, 4.71%, calcd. C, 77.13%; H, 4.67% for $C_{18}H_{13}FO_2$.

EXAMPLE 1.4

2-Methyl-3-(4-trifluoro-benzyl)-4a,8a-dihydro-[1,4] naphthoquinone (P_TM29)

As starting materials for the coupling reaction menadione and 4-(Trifluoromethyl)phenylacetic acid were used. Synthesis is realized according to the general procedure described in general procedure of example 1. After chromatography on silica gel (petroleum ether:$CH_2Cl_2$=1:1, UV), 3.09 g (9.36 mmol, 76% yield) of P_TM29 were isolated as yellow solid.

Melting point: 68-69° C. —$^1$H-NMR (300 MHz, $CDCl_3$): δ=8.04-8.09 (m, 2H), 7.66-7.72 (m, 2H), 7.50 (d, $^3J$=8.21 Hz, 2H), 7.33 (d, $^3J$=8.03 Hz, 2H), 4.07 (s, 2H), 2.23 (s, 3H). —$^{13}$C-NMR (75 MHz, $CDCl_3$): δ=185.12 ($C_q$), 184.50 ($C_q$), 144.88 ($C_q$), 144.41 ($C_q$), 142.22 ($C_q$), 133.67 (CH), 133.66 (CH), 132.09 ($C_q$), 131.91 ($C_q$), 128.88 (CH), 128.85 ($^2J_{CF}$=32.4 Hz, $\underline{C}$—$CF_3$), 126.53 (CH), 126.41 (CH), 125.59 ($^3J_{CF}$=3.8 Hz, CH), 124.19 ($^1J_{CF}$=278.6 Hz, $CF_3$), 32.37 ($CH_2$), 13.38 ($CH_3$). —EI MS (70 eV, m/z (%)): 330.0 ([M]$^+$, 30), 315.0 (100). —IR (KBr): 3400 cm$^{-1}$ (b, m), 3047 (w), 2930 (m), 1662 (vs), 1617 (vs), 1593 (vs), 1418 (m), 1377 (s), 1329 (vs), 1295 (vs), 1259 (m), 1184 (m), 1161 (vs), 1112 (vs), 1069 (vs), 1019 (s), 977 (m), 950 (m), 823 (m), 789 (m), 758 (m), 715 (m), 691 (m). —EA: obs. C, 68.87%; H, 3.98%, calcd. C, 69.09%; H, 3.97% for $C_{19}H_{13}F_3O_2$.

EXAMPLE 1.5

2-Methyl-3-(4-chloro-benzyl)-4a,8a-dihydro-[1,4] naphthoquinone (P_TM30)

As starting materials for the coupling reaction menadione and 4-chlorophenylacetic acid were used. Synthesis is realized according to the general procedure described in general procedure of example 1. After chromatography on silica gel (cyclohexane:ethyl acetate=3:1, UV), 6.46 g (21.8 mmol, 75% yield) of P_TM30 were isolated as yellow solid.

Melting point: 134-135° C. —$^1$H-NMR (300 MHz, $CDCl_3$): δ=8.04-8.10 (m, 2H), 7.66-7.72 (m, 2H), 7.22 (d, $^3J$=8.37 Hz, 2H), 7.14 (d, $^3J$=8.42 Hz, 2H), 3.98 (s, 2H), 2.22 (s, 3H). —$^{13}$C-NMR (75 MHz, $CDCl_3$): δ=185.23 ($C_q$), 184.56 ($C_q$), 144.85 ($C_q$), 144.55 ($C_q$), 136.53 ($C_q$), 133.58 (CH), 132.29 ($C_q$), 132.10 ($C_q$), 131.97 ($C_q$), 129.93 (CH), 128.76 (CH), 126.50 (CH), 126.35 (CH), 31.87 ($CH_2$), 13.31 ($CH_3$). —EI MS (70 eV, m/z (%)): 296.1 ([M]$^+$, 25), 281.0 (100). —IR (KBr): 3439 cm$^{-1}$ (b, m), 3076 (w), 2962 (w), 1687 (s), 1668 (vs), 1656 (vs), 1627 (m), 1595 (m), 1413 (m), 1379 (w), 1326 (vs), 1291 (vs), 1273 (m), 1235 (m), 1172 (s), 1130 (vs), 1110 (m), 1065 (s), 979 (m), 871 (m), 762 (m), 715 (w). —EA: obs. C, 72.89%; H, 4.38%; Cl, 11.83%, calcd. C, 72.85%; H, 4.42%; Cl, 11.95% for $C_{18}H_{13}ClO_2$.

EXAMPLE 1.6

2-Methyl-3-(4-methoxy-benzyl)-4a,8a-dihydro-[1,4] naphthoquinone (P_TM31)

As starting materials for the coupling reaction menadione and 4-methoxyphenylacetic acid were used. After chromatography on silica gel (petroleum ether:$CH_2Cl_2$=1:1, UV), 1.97 g (6.74 mmol, 45% yield) of P_TM31 were isolated as yellow solid.

Melting point: 112-113° C. —$^1$H-NMR (300 MHz, $CDCl_3$): δ=8.03-8.09 (m, 2H), 7.64-7.69 (m, 2H), 7.14 (d, $^3J$=8.77 Hz, 2H), 6.78 (d, $^3J$=8.74 Hz, 2H), 3.97 (s, 2H), 3.73 (s, 3H), 2.23 (s, 3H). —$^{13}$C-NMR (75 MHz, $CDCl_3$): δ=185.45 ($C_q$), 184.71 ($C_q$), 158.14 ($C_q$), 145.59 ($C_q$), 144.02 ($C_q$), 133.43 (CH), 133.40 (CH), 132.10 ($C_q$), 132.04 ($C_q$), 130.02 ($C_q$), 129.60 (CH), 126.42 (CH), 126.21 (CH), 114.04 (CH), 55.21 ($CH_3$), 31.53 ($CH_2$), 13.19 ($CH_3$). —EI MS (70 eV, m/z (%)): 292.1 ([M]$^+$, 24), 277.0 (100), 250.1 (14), 219.1 (19). —IR (KBr): 3441 cm$^{-1}$ (b, m), 2933 (w), 2841 (w), 1662 (vs), 1618 (m), 1595 (s), 1511 (vs), 1458 (w), 1375 (w), 1332 (m), 1297 (vs), 1247 (s), 1178 (m), 1035 (m), 823 (m), 793

EXAMPLE 1.7

2-Methyl-3-(2-methoxy-benzyl)-4a,8a-dihydro-[1,4] naphthoquinone (P_TM32)

As starting materials for the coupling reaction menadione and 2-methoxyphenylacetic acid were used. Synthesis is realized according to the general procedure described in general procedure of example 1. After chromatography on silica gel (petroleum ether:$CH_2Cl_2$=1:1, UV), 3.59 g (12.28 mmol, 82% yield) of P_TM32 were isolated as yellow solid.

Melting point: 117-118° C. —$^1$H-NMR (CDCl$_3$, 300 MHz): δ=8.04-8.10 (m, 2H), 7.64-7.70 (m, 2H), 7.13-7.19 (m, 1H), 7.03 (d, $^3$J=6.53 Hz, 1H), 6.79 (m, 2H), 3.99 (s, 2H), 3.81 (s, 3H), 2.15 (s, 3H). —$^{13}$C-NMR (75 MHz, CDCl$_3$): δ=185.45 ($C_q$), 184.65 ($C_q$), 157.17 ($C_q$), 145.64 ($C_q$), 144.88 ($C_q$), 133.39 (CH), 133.30 (CH), 132.27 ($C_q$), 132.22 ($C_q$), 129.32 (CH), 127.54 (CH), 126.45 (CH), 126.26 ($C_q$), 126.22 (CH), 120.56 (CH), 110.30 (CH), 55.34 (CH$_3$), 26.81 (CH$_2$), 13.05 (CH$_3$). —EI MS (70 eV, m/z (%)): 292.1 ([M]$^+$, 39), 277.1 (100), 250.1 (42). —IR (KBr): 3432 cm$^{-1}$ (b, m), 2960 (w), 2836 (w), 1695 (w), 1661 (s), 1617 (w), 1596 (m), 1493 (m), 1459 (w), 1334 (w), 1295 (s), 1259 (w), 1245 (m), 1110 (w), 1029 (m), 754 (w), 711 (w). —EA: obs. C, 77.77%; H, 5.43%, calcd. C, 78.06%; H, 5.52% for C$_{19}$H$_{16}$O$_3$.

EXAMPLE 1.8

2-Methyl-3-(4-hydroxy-benzyl)-4a,8a-dihydro-[1,4] naphthoquinone (P_TM36)

As starting materials for the coupling reaction menadione and 4-hydroxyphenylacetic acid were used. Synthesis is realized according to the general procedure described in general procedure of example 1. After chromatography on silica gel (cyclohexane:ethyl acetate=3:1, UV), 596 mg (2.1 mmol, 7% yield) of P_TM36 were isolated as yellow solid.

Melting point: 165-166° C. —$^1$H-NMR (300 MHz, CDCl$_3$): δ=8.04-8.09 (m, 2H), 7.65-7.71 (m, 2H), 7.06-7.10 (m, 2H), 6.69-6.73 (m, 2H), 4.70 (bs, 1H), 3.93 (s, 2H), 2.23 (s, 3H). —$^{13}$C-NMR (75 MHz, CDCl$_3$): δ=185.52 ($C_q$), 184.80 ($C_q$), 154.09 ($C_q$), 145.60 ($C_q$), 144.13 ($C_q$), 133.50 (CH), 133.47 ($C_q$), 130.12 ($C_q$), 129.78 (CH), 129.01 (CH), 126.45 (CH), 126.26 (CH), 115.58 (CH), 115.48 (CH), 31.56 (CH$_2$), 13.23 (CH$_3$). —FAB MS (NBA): 277.9 ([M]$^+$, 49). —IR (KBr): 3480 cm$^{-1}$ (b, s), 1659 (vs), 1616 (m), 1595 (s), 1513 (vs), 1336 (m), 1295 (vs), 1260 (m), 1217 (m), 1203 (w), 1176 (w), 708 (s). —EA: obs. C, 77.47%; H, 5.07%, calcd. C, 77.68%; H, 5.07% for C$_{18}$H$_{14}$O$_3$.

EXAMPLE 1.9

2-Methyl-3-(4-nitro-benzyl)-4a,8a-dihydro-[1,4] naphthoquinone (P_TM37)

As starting materials for the coupling reaction menadione and 4-Nitrophenylacetic acid were used. Synthesis is realized according to the general procedure described in general procedure of example 1. After chromatography on silica gel (cyclohexane:ethyl acetate=3:1, UV), 7.97 g (25.9 mmol, 89% yield) of P_TM37 were isolated as yellow solid.

Melting point: 156-157° C. —$^1$H-NMR (300 MHz, CDCl$_3$): δ=8.03-8.13 (m, 4H), 7.68-7.74 (m, 2H), 7.38 (d, $^3$J=8.71 Hz, 2H), 4.11 (s, 2H), 2.24 (s, 3H). —$^{13}$C-NMR (75 MHz, CDCl$_3$): δ=184.94 ($C_q$), 184.39 ($C_q$), 146.69 ($C_q$), 145.83 ($C_q$), 145.17 ($C_q$), 143.82 ($C_q$), 133.81 (CH), 133.76 (CH), 132.05 ($C_q$), 131.81 ($C_q$), 129.39 (CH), 126.57 (CH), 126.49 (CH), 123.91 (CH), 32.51 (CH$_2$), 13.45 (CH$_3$). —EI MS (70 eV, m/z (%)): 307.0 ([M]$^+$, 37), 292.0 (100). —IR (KBr): 3441 cm$^{-1}$ (b, m), 3106 (w), 3076 (w), 1662 (vs), 1625 (s), 1604 (s), 1595 (vs), 1510 (vs), 1494 (m), 1381 (m), 1348 (vs), 1324 (vs), 1297 (vs), 1260 (m), 1184 (m), 982 (m), 951 (s), 847 (s), 786 (s), 742 (s), 724 (vs), 694 (s). —EA: obs. C, 70.24%; H, 4.11%; N, 4.65%, calcd. C, 70.35%; H, 4.26%; N, 4.56% for C$_{18}$H$_{13}$NO$_4$.

EXAMPLE 1.10

2-Methyl-3-(4-cyano-benzyl)-4a,8a-dihydro-[1,4] naphthoquinone (P_TM41)

As starting materials for the coupling reaction menadione and 4-Cyanophenylacetic acid were used. Synthesis is realized according to the general procedure described in general procedure of example 1. After chromatography on silica gel (cyclohexane:ethyl acetate=3:1, UV), 565 g (1.9 mmol, 63% yield) of P_TM41 were isolated as yellow solid.

Melting point: 159-160° C. —$^1$H-NMR (300 MHz, CDCl$_3$): δ=8.03-8.11 (m, 2H), 7.67-7.73 (m, 2H), 7.55 (d, $^3$J=8.32 Hz, 2H), 7.32 (d, $^3$J=8.28 Hz, 2H), 4.06 (s, 2H), 2.22 (s, 3H). —$^{13}$C-NMR (75 MHz, CDCl$_3$): δ=184.98 ($C_q$), 184.42 ($C_q$), 145.09 ($C_q$), 143.91 ($C_q$), 143.71 ($C_q$), 133.78 (CH), 133.73 (CH), 132.47 (CH), 132.06 ($C_q$), 131.82 ($C_q$), 129.35 (CH), 126.56 (CH), 126.47 (CH), 118.75 ($C_q$), 110.49 ($C_q$), 32.69 (CH$_2$), 13.42 (CH$_3$). —EI MS (70 eV, m/z (%)): 287 ([M]$^+$, 8), 286.1 (33), 271.0 (100). —IR (KBr): 3430 cm$^{-1}$ (b, m), 3087 (w), 3069 (w), 3054 (w), 2941 (w), 2227 (vs, CN), 1664 (vs), 1622 (s), 1604 (s), 1594 (s), 1505 (m), 1336 (s), 1328 (s), 1296 (vs), 1264 (w), 1178 (m), 976 (m), 952 (m), 822 (m), 749 (s), 710 (s), 691 (m), 631 (m), 567 (w). —EA: obs. C, 79.16%; H, 4.52%; N, 4.89%, calcd. C, 79.43%; H, 4.56%; N, 4.88% for C$_{19}$H$_{13}$NO$_2$.

EXAMPLE 1.11

2-Methyl-3-(4-tert-butyl-benzyl)-4a,8a-dihydro-[1,4] naphthoquinone (P_TM43)

As starting materials for the coupling reaction menadione and 4-tertbutylphenylacetic acid were used. Synthesis is realized according to the general procedure described in general procedure of example 1. After chromatography on silica gel (cyclohexane:ethyl acetate=3:1, UV), 995 g (3.1 mmol, 67% yield) of P_TM43 were isolated as yellow solid.

Melting point: 60-61° C. —$^1$H-NMR (300 MHz, CDCl$_3$): δ=8.04-8.09 (m, 2H), 7.64-7.70 (m, 2H), 7.27 (d, $^3$J=8.35 Hz, 2H), 7.15 (d, $^3$J=8.33 Hz, 2H), 3.98 (s, 2H), 2.25 (s, 3H), 1.26 (s, 9H). —$^{13}$C-NMR (75 MHz, CDCl$_3$): δ=185.47 ($C_q$), 184.70 ($C_q$), 149.28 ($C_q$), 145.52 ($C_q$), 144.21 ($C_q$), 134.90 ($C_q$), 133.45 (CH), 133.41 (CH), 132.15 ($C_q$), 132.10 ($C_q$), 128.28 (CH), 126.46 (CH), 126.24 (CH), 125.56 (CH), 34.36 ($C_q$), 31.93 (CH$_2$), 31.08 (CH$_3$), 13.30 (CH$_3$). —EI MS (70 eV, m/z (%)): 318.0 ([M]$^+$, 23), 303 (100), 261.0 (31), 247.0 (12). —IR (KBr): 3400 cm$^{-1}$ (b, m), 2961 (m), 2905 (w), 2868 (w), 1659 (vs), 1619 (m), 1594 (m), 1512 (w), 1462 (w), 1369 (m), 1333 (m), 1314 (m), 1294 (vs), 1270 (w), 976 (w), 81818 (w), 717 (m), 692 (w), 571 (w), 541 (w). —EA: obs. C, 82.35%; H, 6.80%, calcd. C, 82.22%; H, 7.01% for C$_{22}$H$_{22}$O$_2$ 0.1 EtOAc.

EXAMPLE 1.12

[4-(3-Methyl-1,4-dioxo-1,4,4a,8a-tetrahydro-naphthalen-2-ylmethyl)-phenyl]-carbamic acid tert-butyl ester (P_TM45)

As starting materials for the coupling reaction menadione and (4-tert-Butoxycarbonylamino-phenyl)-acetic acid were used. Synthesis is realized according to the general procedure described in general procedure of example 1. After chromatography on silica gel (cyclohexane:ethyl acetate=3:1, UV), 527 mg (1.4 mmol, 12% yield) of P_TM45 were isolated as yellow solid.

Melting point: 148-149° C. —$^1$H-NMR (300 MHz, CDCl$_3$): δ=8.05-8.08 (m, 2H), 7.66-7.71 (m, 2H), 7.23 (d, $^3$J=8.26 Hz, 2H), 7.12 (d, $^3$J=8.57 Hz, 2H), 6.36 (s, 1H), 3.95 (s, 2H), 2.21 (s, 3H), 1.47 (s, 9H). —$^{13}$C-NMR (75 MHz, CDCl$_3$): δ=185.42 (C$_q$), 184.68 (C$_q$), 152.73 (C$_q$), 145.38 (C$_q$), 144.21 (C$_q$), 136.70 (C$_q$), 133.47 (CH), 133.44 (CH), 132.61 (C$_q$), 132.10 (C$_q$), 132.03 (C$_q$), 129.14 (CH), 126.45 (CH), 126.25 (CH), 118.88 (CH), 80.49 (C$_q$), 31.74 (CH$_2$), 28.30 (CH$_3$), 13.22 (CH$_3$). —EI MS (70 eV, m/z (%)): 377.2 ([M]$^+$, 18), 321.1 (66), 305.9 (100), 261.1 (59), 201.3 (14), 160.1 (18), 121.1 (21). —IR (KBr): 3439 (b, vs), 1704 (w), 1685 (w), 1660 (s), 1618 (m), 1596 (m), 1521 (m), 1370 (w), 1315 (m), 1296 (m), 1236 (w), 1162 (s), 709 (w). —EA: obs. C, 72.94%; H, 6.16%; N, 3.74%, calcd. C, 73.19%; H, 6.14%, N, 3.71% for C$_{23}$H$_{23}$NO$_4$.

EXAMPLE 1.13

4-(3-Methyl-1,4-dioxo-1,4,4a,8a-tetrahydro-naphthalen-2-ylmethyl)-benzoic acid (P_TM50)

As starting materials for the coupling reaction menadione and 4-carboxyphenylacetic acid were used. Synthesis is realized according to the general procedure described in general procedure of example 1. After chromatography on silica gel (petroleum ether:CH$_2$Cl$_2$=1:3, UV), 102 mg (0.33 mmol, 12% yield) of P_TM50 were isolated as yellow solid.

Melting point: 206-208° C. —$^1$H-NMR (300 MHz, DMSO): δ=7.99-8.04 (m, 2H), 7.79-7.89 (m, 4H), 7.35 (d, $^3$J=8.15 Hz, 2H), 4.06 (s, 2H), 2.15 (s, 3H). —$^{13}$C-NMR (75 MHz, DMSO): δ=184.57 (C$_q$), 184.03 (C$_q$), 167.26 (C$_q$), 144.76 (C$_q$), 143.79 (C$_q$), 143.33 (C$_q$), 133.95 (CH), 133.90 (CH), 131.71 (C$_q$), 131.43 (C$_q$), 129.51 (CH), 128.40 (CH), 125.98 (CH), 125.88 (CH), 31.78 (CH$_2$), 13.05 (CH$_3$). —EI MS (70 eV, m/z (%)): 305.9 ([M]$^+$, 22), 290.9 (100), 260.9 (21). —IR (KBr): 3455 cm$^{-1}$ (b, vs), 3071 (m), 2932 (m), 1701 (vs), 1659 (vs), 1610 (s), 1594 (s), 1423 (m), 1376 (m), 1319 (m), 1295 (vs), 1234 (m), 1181 (m), 1114 (w), 949 (w), 778 (m), 757 (m), 719 (m), 695 (m), 631 (w). —EA: obs. C, 73.28%; H, 4.84%, calcd. C, 73.42%; H, 4.70% for C$_{19}$H$_{14}$O$_4$ 0.25H$_2$O.

EXAMPLE 1.14

2-(3,4-Dimethoxy-benzyl)-3-methyl-4a,8a-dihydro-[1,4]naphthoquinone (P_TM54)

As starting materials for the coupling reaction menadione and 3,4-dimethoxyphenylacetic acid were used. Synthesis is realized according to the general procedure described in general procedure of example 1. After chromatography on silica gel (petroleum ether:CH$_2$Cl$_2$=1:1, UV), 4.25 g (13.2 mmol, 65% yield) of P_TM54 were isolated as orange solid.

Melting point: 102-103° C. —$^1$H-NMR (300 MHz, CDCl$_3$): δ=8.06-8.08 (m, 2H), 7.67-7.69 (m, 2H), 6.79 (s, 1H), 6.71-6.74 (m, 2H), 3.95 (s, 2H), 3.83 (s, 3H), 3.80 (s, 3H), 2.25 (s, 3H). —$^{13}$C-NMR (75 MHz, CDCl$_3$): δ=185.43 (C$_q$), 184.78 (C$_q$), 149.01 (C$_q$), 147.67 (C$_q$), 145.41 (C$_q$), 144.13 (C$_q$), 133.48 (CH), 133.46 (CH), 132.11 (C$_q$), 132.04 (C$_q$), 130.47 (C$_q$), 126.45 (CH), 126.26 (CH), 120.46 (CH), 112.19 (CH), 111.27 (CH), 55.88 (CH$_3$), 31.99 (CH$_2$), 13.26 (CH$_3$). —EI MS (70 eV, m/z (%)): 322.2 ([M]$^+$, 28), 307.1 (100). —IR (KBr): 3400 cm$^{-1}$ (b, s), 3002 (w), 2954 (w), 2935 (w), 2834 (w), 1660 (vs), 1618 (m), 1594 (m), 1514 (vs), 1461 (m), 1444 (m), 1419 (w), 1376 (w), 1334 (m), 1295 (vs), 1262 (vs), 1238 (s), 1184 (w), 1143 (s), 1027 (m), 976 (w), 748 (m), 701 (m). —EA: obs. C, 74.28%; H, 5.64, calcd. C, 74.52%; H, 5.63% for C$_{20}$H$_{18}$O$_4$.

EXAMPLE 1.15

2-(2,4-Dimethoxy-benzyl)-3-methyl-4a,8a-dihydro-[1,4]naphthoquinone (P_TM56)

As starting materials for the coupling reaction menadione and 2,4-dimethoxyphenylacetic acid were used. Synthesis is realized according to the general procedure described in general procedure of example 1. After chromatography on silica gel (petroleum ether:CH$_2$Cl$_2$=1:1, UV), 922 mg (2.86 mmol, 37% yield) of P_TM56 were isolated as orange solid.

Melting point: 103-105° C. —$^1$H-NMR (300 MHz, CDCl$_3$,): δ=8.03-8.09 (m, 2H), 7.64-7.70 (m, 2H), 6.95 (d, $^3$J=8.33 Hz, 1H), 6.41 (d, $^4$J=2.40 Hz, 1H), 6.35 (dd, $^3$J=8.34 Hz, $^4$J=2.44 Hz, 1H), 3.91 (s, 2H), 3.78 (s, 3H), 3.74 (s, 3H), 2.16 (s, 3H). —$^{13}$C-NMR (75 MHz, CDCl$_3$): δ=185.95 (C$_q$), 185.18 (C$_q$), 159.87 (C$_q$), 158.47 (C$_q$), 146.21 (C$_q$), 145.03 (C$_q$), 133.76 (CH), 133.67 (CH), 132.69 (C$_q$), 132.62 (C$_q$), 130.21 (CH), 126.82 (CH), 126.59 (CH), 118.98 (C$_q$), 104.46 (CH), 98.90 (CH), 55.74 (CH$_3$), 26.67 (CH$_2$), 13.39 (CH$_3$). —EI MS (70 eV, m/z (%)): 322.2 ([M]$^+$, 23), 307.2 (89), 138.1 (25). —IR (KBr): 3445 cm$^{-1}$ (b, m), 2994 (w), 2937 (w), 2836 (w), 1660 (vs), 1614 (s), 1591 (s), 1506 (s), 1462 (m), 1421 (w), 1376 (w), 1331 (m), 1295 (vs), 1262 (s), 1209 (m), 1183 (m), 1157 (m), 1119 (m), 1037 (m), 828 (w), 707 (m). —EA: obs. C, 74.33%, H, 5.75%, calcd. C, 74.52%; H, 5.63% for C$_{20}$H$_{18}$O$_4$.

EXAMPLE 1.16

2-Methyl-3-pentafluorophenylmethyl-4a,8a-dihydro [1,4]naphtha-quinone (P_TM57)

As starting materials for the coupling reaction menadione and 2,3,4,5,6-pentafluorophenylacetic acid were used. Synthesis is realized according to the general procedure described in general procedure of example 1. After chromatography on silica gel (petroleum ether:CH$_2$Cl$_2$=1:1, UV), 306 mg (0.87 mmol, 44% yield) of P_TM57 were isolated as yellow solid.

Melting point: 103-104° C. —$^1$H-NMR (300 MHz, CDCl$_3$): δ=8.00-8.07 (m, 2H), 7.67-7.70 (m, 2H), 4.02 (s, 2H), 2.24 (s, 3H). —$^{13}$C-NMR (75 MHz, CDCl$_3$): δ=184.70 (C$_q$), 183.67 (C$_q$), 146.93 (CF), 145.43 (C$_q$), 143.66 (CF), 141.85 (C$_q$), 139.15 (CF), 138.36 (CF), 135.77 (CF), 133.73 (CH), 133.71 (CH), 131.97 (C$_q$), 131.73 (C$_q$), 126.48 (CH), 126.47 (CH), 111.95 (C$_q$), 20.90 (CH$_2$), 12.98 (CH$_3$). —EI MS (70 eV, m/z (%)): 352.1 ([M]$^+$, 100), 332.1 (9), 303.1 (25). —IR (KBr): 3438 cm$^{-1}$ (b, m), 1667 (vs), 1621 (m), 1594 (s), 1523 (vs), 1501 (vs), 1459 (w), 1375 (s), 1331 (vs), 1294 (vs), 1258 (m), 1119 (s), 1066 (m), 1027 (w), 1002 (s), 972 (s), 952 (vs), 729 (m), 713 (m). —EA: obs. C, 61.18%; H, 2.68%, calcd. C, 61.37%; H, 2.58% for $C_{18}H_9F_5O_2$.

EXAMPLE 1.17

2-(3,5-Dimethoxy-benzyl)-3-methyl-4a,8a-dihydro-[1,4]naphthoquinone (P_TM58)

As starting materials for the coupling reaction menadione and 3,5-dimethoxyphenylacetic acid were used. Synthesis is realized according to the general procedure described in general procedure of example 1. After chromatography on silica gel (petroleum ether:$CH_2Cl_2$=1:1, UV), 555 mg (1.72 mmol, 75% yield) of P_TM58 were isolated as yellow solid.

Melting point: 127-128° C. —$^1$H-NMR (300 MHz, $CDCl_3$): δ=8.02-8.06 (m, 2H), 7.63-7.69 (m, 2H), 6.35 (d, $^4J$=2.17 Hz, 2H), 6.26 (t, $^4J$=2.20 Hz, 1H), 3.94 (s, 2H), 3.72 (s, 6H), 2.21 (s, 3H). —$^{13}$C-NMR (75 MHz, $CDCl_3$,): δ=185.21 ($C_q$), 184.49 ($C_q$), 160.84 ($C_q$), 144.87 ($C_q$), 144.55 ($C_q$), 140.22 ($C_q$), 133.39 (CH), 133.37 (CH), 132.05 ($C_q$), 131.95 ($C_q$), 126.40 (CH), 126.18 (CH), 106.78 (CH), 97.94 (CH), 55.18 ($CH_3$), 32.43 ($CH_2$), 13.20 ($CH_3$). —EI MS (70 eV, m/z (%)): 322.1 ([M]$^+$, 20), 307.1 (30), 292.1 (10). —IR (KBr): 3438 cm$^{-1}$ (b, m), 2958 (w), 2941 (w), 2837 (w), 1661 (vs), 1600 (vs), 1471 (s), 1426 (m), 1376 (m), 1332 (s), 1292 (vs), 1262 (w), 1208 (s), 1157 (vs), 1071 (m), 1055 (m), 975 (w), 822 (m), 737 (vs), 691 (m). —EA: obs. C, 74.24%; H, 5.61%, calcd. C, 74.52%; H, 5.63% for $C_{20}H_{18}O_4$.

EXAMPLE 1.18

2-Methyl-3-(3,4,5-trimethoxy-benzyl)-4a,8a-dihydro-[1,4]naphtha-quinone (P_TM59)

As starting materials for the coupling reaction menadione and 3,4,5-trimethoxy-phenylacetic acid were used. After chromatography on silica gel (petroleum ether:$CH_2Cl_2$=1:3, UV), 1.98 g (5.62 mmol, 85% yield) of P_TM59 were isolated as yellow solid.

Melting point: 147-149° C. —$^1$H-NMR (300 MHz, $CDCl_3$): δ=8.01-8.07 (m, 2H), 7.63-7.69 (m, 2H), 6.42 (s, 2H), 3.92 (s, 2H), 3.77 (s, 6H), 3.75 (s, 3H), 2.24 (s, 3H). —$^{13}$C-NMR (75 MHz, $CDCl_3$): δ=185.23 ($C_q$), 184.63 ($C_q$), 153.18 ($C_q$), 144.97 ($C_q$), 144.23 ($C_q$), 136.59 ($C_q$), 133.54 ($C_q$), 133.44 (CH), 131.98 ($C_q$), 131.89 ($C_q$), 126.37 (CH), 126.20 (CH), 106.61 (CH), 105.75 (CH), 60.73 ($CH_3$), 56.06 ($CH_3$), 32.57 ($CH_2$), 13.28 ($CH_3$). —EI MS (70 eV, m/z (%)): 352.1 ([M]$^+$, 54), 337.1 (100). —IR (KBr): 3481 cm$^{-1}$ (b, s), 2942 (w), 2836 (w), 1658 (vs), 1592 (s), 1507 (m), 1458 (m), 1330 (m), 1296 (s), 1127 (vs), 731 (m). —EA: obs. C, 71.25%; H, 5.75%, calcd. C, 71.58%, H, 5.72% for $C_{21}H_{20}O_5$.

EXAMPLE 1.19

2-(2,5-Dimethoxy-benzyl)-3-methyl-4a,8a-dihydro-[1,4]naphthoquinone (P_TM60)

As starting materials for the coupling reaction menadione and 2,5-dimethoxyphenylacetic acid were used. Synthesis is realized according to the general procedure described in general procedure of example 1. After chromatography on silica gel (petroleum ether:$CH_2Cl_2$=1:3, UV), 1.96 g (6.08 mmol, 80% yield) of P_TM60 were isolated as yellow solid.

Melting point: 140-142° C. —$^1$H-NMR (300 MHz, $CDCl_3$): δ=8.05-8.08 (m, 2H), 7.64-7.69 (m, 2H), 6.76 (d, $^3J$=8.80 Hz, 1H), 6.66 (dd, $^3J$=8.81 Hz, $^4J$=2.96 Hz, 1H), 6.59 (d, $^4J$=2.92 Hz, 1H), 3.98 (s, 2H), 3.78 (s, 3H), 3.67 (s, 3H), 2.15 (s, 3H). —$^{13}$C-NMR (75 MHz, $CDCl_3$): δ=185.35 ($C_q$), 184.55 ($C_q$), 153.52 ($C_q$), 151.50 ($C_q$), 145.40 ($C_q$), 144.94 ($C_q$), 133.36 (CH), 133.28 (CH), 132.22 ($C_q$), 132.21 ($C_q$), 127.62 ($C_q$), 126.43 (CH), 126.20 (CH), 116.20 (CH), 111.14 (CH), 110.91 (CH), 55.93 ($CH_3$), 55.61 ($CH_3$), 26.68 ($CH_2$), 12.99 ($CH_3$). —EI MS (70 eV, m/z (%)): 322.1 ([M]$^+$, 100), 307.1 (67), 291.1 (38), 277.0 (20). —IR (KBr): 3450 cm$^{-1}$ (b, m), 3006 (w), 2955 (w), 2833 (w), 1660 (vs), 1612 (s), 1590 (s), 1499 (vs), 1465 (m), 1372 (m), 1325 (m), 1295 (vs), 1280 (s), 1261 (s), 1235 (vs), 1163 (m), 1051 (s), 1022 (m), 793 (m), 708 (s). —EA: obs. C, 73.16%; H, 5.51%, calcd. C, 72.97%; H, 5.54% for $C_{20}H_{18}O_4$ 0.1 $CH_2Cl_2$.

EXAMPLE 1.20

2-Methyl-3-(2,3,4-trimethoxy-benzyl)-4a,8a-dihydro-[1,4]naphtha-quinone (P_TM61)

As starting materials for the coupling reaction menadione and 2,3,4-trimethoxyphenylacetic acid were used. Synthesis is realized according to the general procedure described in general procedure of example 1. After chromatography on silica gel (petroleum ether:$CH_2Cl_2$=1:9, UV), 544 mg (1.540 mmol, 76% yield) of P_TM61 were isolated as yellow solid.

Melting point: 102-103° C. —$^1$H-NMR (300 MHz, $CDCl_3$): δ=8.04-8.08 (m, 2H), 7.64-7.69 (m, 2H), 6.70 (d, $^3J$=8.69 Hz, 1H), 6.52 (d, $^3J$=8.60 Hz, 1H), 3.94 (s, 2H), 3.87 (s, 3H), 3.83 (s, 3H), 3.78 (s, 3H), 2.15 (s, 3H). —$^{13}$C-NMR (75 MHz, $CDCl_3$): δ=185.40 ($C_q$), 184.59 ($C_q$), 152.40 ($C_q$), 151.68 ($C_q$), 145.70 ($C_q$), 144.53 ($C_q$), 142.28 ($C_q$), 133.38 (CH), 133.31 (CH), 132.18 ($C_q$), 132.16 ($C_q$), 126.40 (CH), 126.21 (CH), 123.98 ($C_q$), 123.36 (CH), 107.18 (CH), 60.75 ($CH_3$), 60.69 ($CH_3$), 55.94 ($CH_3$), 26.52 ($CH_2$), 12.99 ($CH_3$). —EI MS (70 eV, m/z (%)): m/z=352.2 ([M]$^+$, 61), 337.2 (100), 191.1 (28). —IR (KBr): 3440 cm$^{-1}$ (b, m), 2974 (w), 2941 (w), 2927 (w), 1663 (vs), 1616 (m), 1594 (s), 1493 (s), 1465 (s), 1416 (m), 1332 (m), 1296 (vs), 1260 (m), 1202 (w), 1101 (vs), 1044 (s), 973 (w), 786 (w), 713 (w), 696 (w). —EA: obs. C, 71.49%, H, 5.76%, calcd. C, 71.58%; H, 5.72% for $C_{21}H_{20}O_5$.

EXAMPLE 1.21

2-Methyl-3-benzyl-4a,8a-dihydro-[1,4]naphtho-quinone (P_TM62)

As starting materials for the coupling reaction menadione and phenylacetic acid were used. Synthesis is realized according to the general procedure described in general procedure of example 1. After chromatography on silica gel (petroleum ether:$CH_2Cl_2$=1:3, UV), 2.50 g (9.53 mmol, 86% yield) of P_TM62 were isolated as yellow hygroscopic solid.

Melting point: 103-104° C. —$^1$H-NMR (300 MHz, $CDCl_3$): δ=8.03-8.09 (m, 2H), 7.63-7.68 (m, 2H), 7.16-7.33 (m, 5H), 4.02 (s, 2H), 2.24 (s, 3H). —$^{13}$C-NMR (75 MHz, $CDCl_3$): δ=185.16 ($C_q$), 184.45 ($C_q$), 145.17 ($C_q$), 144.26 ($C_q$), 137.95 ($C_q$), 133.33 (CH), 133.30 (CH), 131.97 ($C_q$), 131.89 ($C_q$), 128.53 (CH), 128.50 (CH), 126.31 (CH), 126.11 (CH), 32.29 ($CH_2$), 13.14 ($CH_3$). —EI MS (70 eV, m/z (%)): 262.2 ([M]$^+$, 30), 247.1 (100). —IR (KBr): 3454 cm$^{-1}$ (b, m), 3061 (w), 3028 (w), 2937 (w), 1662 (vs), 1654 (vs), 1620 (m), 1593 (m), 1333 (m), 1293 (vs), 718 (s), 698 (m). —EA: obs. C, 82.39%; H, 5.47%, calcd. C, 82.42%; H, 5.38% for $C_{18}H_{14}O_2$.

EXAMPLE 1.22

3-(4-Bromo-benzyl)-5-hydroxy-2-methyl-4a,8a-dihydro-[1,4]naphthoquinone (P_TM42)

As starting materials for the coupling reaction plumbagin and 4-bromophenylacetic acid were used. Synthesis is realized according to the general procedure described in general procedure of example 1. After chromatography on silica gel (cyclohexane:ethyl acetate=3:1, UV), 1.35 g (3.8 mmol, 71% yield) of P_TM42 were isolated as red solid.

Melting point: 163-164° C. —$^1$H-NMR (300 MHz, CDCl$_3$): δ=12.07 (s, 1H), 7.54-7.63 (m, 2H), 7.38 (d, $^3$J=8.38 Hz, 2H), 7.22 (dd, $^3$J=7.94 Hz, $^4$J=1.53 Hz, 1H), 7.09 (d, $^3$J=8.33 Hz, 2H), 3.94 (s, 2H), 2.22 (s, 3H). —$^{13}$C-NMR (75 MHz, CDCl$_3$): δ=189.68 ($C_q$), 184.42 ($C_q$), 161.33 ($C_q$), 146.01 ($C_q$), 144.54 ($C_q$), 136.72 ($C_q$), 136.17 (CH), 132.07 ($C_q$), 131.81 (CH), 130.21 (CH), 124.07 (CH), 120.47 ($C_q$), 119.09 (CH), 114.86 ($C_q$), 31.32 (CH$_2$), 13.44 (CH$_3$). —EI MS (70 eV, m/z (%)): 356.0 ([M]$^+$, 26), 341 (100), 261.1 (25), 107 (40), 77.0 (80). —IR (KBr): 3440 cm$^{-1}$ (b, m), 3047 (w), 1658 (s), 1635 (vs), 1610 (s), 1486 (s), 1456 (s), 1376 (w), 1359 (w), 1315 (w), 1294 (vs), 1266 (vs), 1198 (m), 1163 (w), 1070 (w), 1011 (m), 831 (w), 752 (m), 742 (w). —EA: obs. C, 60.54%; H, 3.75%; Br, 22.52%, calcd. C, 60.52%; H, 3.67%; Br, 22.37% for C$_{18}$H$_{13}$BrO$_3$.

EXAMPLE 1.23

3-(4-tert-Butyl-benzyl)-5-hydroxy-2-methyl-[1,4]naphthoquinone (P_TM81)

As starting materials for the coupling reaction plumbagin and 4-tertbutylphenylacetic acid were used. Synthesis is realized according to the general procedure described in general procedure of example 1. After chromatography on silica gel (petroleum ether:CH$_2$Cl$_2$=1:3, UV), 1.25 g (3.73 mmol, 70% yield) of P_TM81 were isolated as red solid.

Melting point: 112-113° C. —$^1$H-NMR (300 MHz, CDCl$_3$): δ=12.15 (s, 1H), 7.51-7.61 (m, 2H), 7.29 (d, $^3$J=8.34 Hz, 2H), 7.14-7.21 (m, 3H), 3.97 (s, 2H), 2.25 (s, 3H), 1.28 (s, 9H). —$^{13}$C-NMR (75 MHz, CDCl$_3$): δ=189.82 ($C_q$), 184.55 ($C_q$), 161.16 ($C_q$), 149.39 ($C_q$), 145.57 ($C_q$), 145.18 ($C_q$), 135.91 (CH), 134.48 ($C_q$), 132.05 ($C_q$), 128.11 (CH), 125.57 (CH), 123.83 (CH), 118.84 (CH), 114.88 ($C_q$), 34.32 ($C_q$), 31.27 (CH$_2$), 31.26 (CH$_3$), 13.36 (CH$_3$). —EI MS (70 eV, m/z (%)): 334.14 ([M]$^+$, 31), 319.11 (100), 277.07 (38), 263.06 (5), 173.05 (8), 152.03 (9). —IR (KBr): 3443 cm$^{-1}$ (b, w), 2964 (m), 1660 (s), 1634 (vs), 1612 (vs), 1514 (m), 1456 (vs), 1384 (w), 1360 (s), 1323 (m), 1305 (vs), 1294 (vs), 1270 (vs), 1199 (m), 1163 (m), 1058 (w), 831 (m), 761 (s), 748 (s), 710 (m). —EA: obs. C, 78.61%; H, 6.60%; calcd. C, 79.02%; H, 6.63% for C$_{22}$H$_{22}$O$_3$.

EXAMPLE 1.24

2-(3-Methoxy-benzyl)-3-methyl-[1,4]naphthoquinone (P_TM96)

As starting materials for the coupling reaction menadione and 3-methoxyphenylacetic acid were used. Synthesis is realized according to the general procedure described in general procedure of example 1. After chromatography on silica gel (petroleum ether:CH$_2$Cl$_2$=1:1, UV), 1.64 g (5.61 mmol, 75% yield) of P_TM96 were isolated as yellow solid.

Melting point: 87-88° C. —$^1$H-NMR (300 MHz, CDCl$_3$): δ=8.05-8.08 (m, 2H), 7.66-7.69 (m, 2H), 7.16 (t, $^3$J=7.87 Hz, 1H), 6.69-6.81 (m, 3H), 3.99 (s, 2H), 3.74 (s, 3H), 2.23 (s, 3H). —$^{13}$C-NMR (75 MHz, CDCl$_3$): δ=185.36 ($C_q$), 184.62 ($C_q$), 159.78 ($C_q$), 145.14 ($C_q$), 144.53 ($C_q$), 139.58 ($C_q$), 133.49 (CH), 133.46 (CH), 132.13 ($C_q$), 132.04 ($C_q$), 129.59 (CH), 126.49 (CH), 126.27 (CH), 120.97 (CH), 114.68 (CH), 111.42 (CH), 55.16 (CH$_3$), 32.37 (CH$_2$), 13.29 (CH$_3$). —EI MS (70 eV, m/z (%)): 292.19 ([M]$^+$, 39), 277.16 (100), 172.10 (12). —IR (KBr): 3066 cm$^{-1}$ (w), 2978 (w), 2945 (w), 2838 (w), 1659 (vs), 1617 (s), 1599 (vs), 1490 (vs), 1470 (s), 1434 (m), 1383 (s), 1327 (vs), 1294 (vs), 1264 (vs), 1256 (vs), 1163 (s), 1040 (vs), 976 (m), 849 (m), 799 (s), 788 (m), 745 (vs), 710 (m), 697 (s). —EA: obs. C, 78.31%; H, 5.53%, calcd. C, 78.06%; H, 5.52% for C$_{19}$H$_{16}$O$_3$.

EXAMPLE 1.25

2-Methyl-3-(4-trifluoromethoxy-benzyl)-[1,4]naphthoquinone (P_TM97)

As starting materials for the coupling reaction menadione and 4-(trifluoromethoxy)phenylacetic acid were used. Synthesis is realized according to the general procedure described in general procedure of example 1. After chromatography on silica gel (petroleum ether:CH$_2$Cl$_2$=1:1, UV), 494 mg (1.43 mmol, 78% yield) of P_TM97 were isolated as yellow solid. Melting point: 64-65° C. —$^1$H-NMR (300 MHz, CDCl$_3$): δ=8.03-8.10 (m, 2H), 7.65-7.71 (m, 2H), 7.34 (d, $^3$J=8.74 Hz, 2H), 7.09 (d, $^3$J=8.08 Hz, 2H), 4.01 (s, 2H), 2.23 (s, 3H). —$^{13}$C-NMR (75 MHz, CDCl$_3$): δ=185.17 ($C_q$), 184.52 ($C_q$), 147.42 ($C_q$), 144.72 ($C_q$), 144.57 ($C_q$), 136.76 ($C_q$), 133.57 (CH), 132.07 ($C_q$), 131.92 ($C_q$), 129.87 (CH), 126.47 (CH), 126.33 (CH), 121.15 (CH), 120.44 (q, $^1J_{CF}$=256.91 Hz), 31.78 (CH$_2$), 13.27 (CH$_3$). —EI MS (70 eV, m/z (%)): 346.0 ([M]$^+$, 32), 331.1 (100), 261.1 (8), 175.1 (71), 76.0 (10), 28.0 (49). —IR (KBr): 3077 cm$^{-1}$ (w), 3047 (w), 3021 (w), 3003 (w), 2963 (w), 2948 (w), 2853 (w), 2143 (w), 2004 (w), 1975 (w), 1901 (w), 1876 (w), 1664 (vs), 1620 (m), 1596 (s), 1508 (s), 1446 (w), 1435 (w), 1378 (m), 1333 (s), 1297 (vs), 1271 (vs), 1217 (vs), 1188 (vs), 1166 (vs), 1111 (m), 1019 (w), 976 (m), 793 (w), 770 (w), 708 (s), 692 (w). —EA: obs. C, 65.78%; H, 3.98%, calcd. C, 65.90%; H, 3.78% for C$_{19}$H$_{13}$F$_3$O$_3$.

EXAMPLE 1.26

2-Methyl-3-(2-bromo-benzyl)-4a,8a-dihydro-[1,4]naphthoquinone (P_TM98)

As starting materials for the coupling reaction menadione and 2-bromophenylacetic acid were used. Synthesis is realized according to the general procedure described in general procedure of example 1. After chromatography on silica gel (petroleum ether:CH$_2$Cl$_2$=1:1, UV), 1.75 g (5.14 mmol, 88% yield) of P_TM98 were isolated as yellow solid.

Melting point: 94-95° C. —$^1$H-NMR (300 MHz, CDCl$_3$): δ=8.06-8.11 (m, 2H), 7.66-7.72 (m, 2H), 7.56 (dd, $^3$J=7.87 Hz, $^4$J=1.32 Hz, 1H), 7.13 (dt, $^3$J=7.47 Hz, $^4$J=1.35 Hz, 1H), 7.04 (dt, $^3$J=7.69 Hz, $^4$J=1.75 Hz, 1H), 6.89 (dd, $^3$J=7.61 Hz, $^4$J=1.56 Hz, 1H), 4.11 (s, 2H), 2.10 (s, 3H). —$^{13}$C-NMR (75 MHz, CDCl$_3$): δ=184.98 ($C_q$), 184.30 ($C_q$), 145.85 ($C_q$), 144.53 ($C_q$), 137.31 ($C_q$), 133.55 (CH), 133.53 (CH), 132.87 (CH), 132.13 ($C_q$), 131.96 ($C_q$), 128.59 (CH), 127.93 (CH), 127.55 (CH), 126.53 (CH), 126.33 (CH), 124.67 ($C_q$), 32.65 (CH$_2$), 13.26 (CH$_3$). —EI MS (70 eV, m/z (%)): 261.1 ([M-Br]$^+$, 100), 231.1 (11), 202.1 (11), 130.1 (8), 76.0 (10). —IR (KBr): 3441 cm$^{-1}$ (b, s), 3068 (w), 3017 (w), 2923 (w), 1660 (vs), 1621 (s), 1594 (s), 1467 (m), 1439 (m), 1376 (w), 1318

(m), 1296 (vs), 1263 (m), 1223 (w), 1184 (w), 1025 (m), 976 (m), 787 (w), 749 (s), 729 (m), 695 (w), 663 (w). —EA: obs. C, 63.12%; H, 3.91%; Br, 23.31%, calcd. C, 63.36%; H, 3.84%; Br, 23.42% for $C_{18}H_{13}BrO_2$.

EXAMPLE 1.27

2-Methyl-3-(3-bromo-benzyl)-4a,8a-dihydro-[1,4]naphthoquinone (P_TM99)

As starting materials for the coupling reaction menadione and 3-bromophenylacetic acid were used. Synthesis is realized according to the general procedure described in general procedure of example 1. After chromatography on silica gel (petroleum ether:$CH_2Cl_2$=1:1, UV), 328 mg (0.96 mmol, 52% yield) of P_TM99 were isolated as yellow solid.

Melting point: 108-109° C. —$^1$H-NMR (300 MHz, $CDCl_3$): δ=7.98-8.02 (m, 2H), 7.59-7.65 (m, 2H), 7.28 (s, 1H), 7.24 (td, $^3$J=6.78 Hz, $^4$J=1.97 Hz, 1H), 7.02-7.09 (m, 2H), 3.92 (s, 2H), 2.16 (s, 3H). —$^{13}$C-NMR (75 MHz, $CDCl_3$): δ=185.16 ($C_q$), 184.45 ($C_q$), 144.78 ($C_q$), 144.50 ($C_q$), 140.35 ($C_q$), 133.59 (CH), 132.10 ($C_q$), 131.94 ($C_q$), 131.52 (CH), 130.16 (CH), 129.65 (CH), 127.26 (CH), 126.54 (CH), 126.36 (CH), 122.72 ($C_q$), 32.09 ($CH_2$), 13.35 ($CH_3$). —EI MS (70 eV, m/z (%)): 340.0 ([M]$^+$, 28), 325.06 (100), 246.13 (18), 215.14 (7), 202.12 (8), 184.99 (12), 76.0 (10). —IR (KBr): 3430 cm$^{-1}$ (b, w), 1658 (vs), 1620 (vs), 1595 (vs), 1568 (s), 1474 (s), 1431 (m), 1381 (s), 1334 (vs), 1290 (s), 1261 (s), 1180 (s), 1074 (m), 974 (s), 955 (s), 793 (s), 780 (vs), 728 (vs), 692 (s), 687 (s), 422 (m). —EA: obs. C, 63.55%; H, 3.94%; Br, 23.69%, calcd. C, 63.36%; H, 3.84%; Br, 23.42% for $C_{18}H_{13}BrO_2$.

EXAMPLE 1.28

2-Methyl-3-(4-isopropyl-benzyl)-4a,8a-dihydro-[1,4]naphthoquinone (P_TM100)

As starting materials for the coupling reaction menadione and 4-isopropylphenylacetic acid were used. Synthesis is realized according to the general procedure described in general procedure of example 1. After chromatography on silica gel (petroleum ether:$CH_2Cl_2$=1:1, UV), 395 mg (1.30 mmol, 58% yield) of P_TM100 were isolated as yellow solid.

Melting point: 64-65° C. —$^1$H-NMR (300 MHz, $CDCl_3$): δ=8.05-8.09 (m, 2H), 7.65-7.69 (m, 2H), 7.14 (d, $^3$J=8.24 Hz, 2H), 7.11 (d, $^3$J=8.24 Hz, 2H), 3.99 (s, 2H), 2.83 (sep, $^3$J=6.90 Hz, 1H), 2.25 (s, 3H), 1.19 (d, $^3$J=6.94 Hz, 6H). —$^{13}$C-NMR (75 MHz, $CDCl_3$): δ=185.45 ($C_q$), 184.68 ($C_q$), 146.99 ($C_q$), 145.52 ($C_q$), 144.20 ($C_q$), 135.26 ($C_q$), 133.44 (CH), 133.40 (CH), 132.13 ($C_q$), 132.07 ($C_q$), 128.53 (CH), 126.68 (CH), 126.45 (CH), 126.23 (CH), 33.66 (CH), 32.02 ($CH_2$), 23.97 ($CH_3$), 13.29 ($CH_3$). —EI MS (70 eV, m/z (%)): 304.1 ([M]$^+$, 31), 289.2 (100), 261.2 (31). —IR (KBr): 3447 cm$^{-1}$ (b, m), 2960 (m), 2928 (w), 2870 (w), 1660 (vs), 1618 (vs), 1594 (s), 1511 (m), 1460 (w), 1419 (w), 1377 (w), 1333 (m), 1294 (vs), 1259 (w), 1181 (w), 975 (w), 818 (w), 788 (w), 718 (m), 694 (m). —EA: obs. C, 82.94%; H, 6.54%, calcd. C, 82.86%; H, 6.62% for $C_{21}H_{20}O_2$.

EXAMPLE 1.29

2-(4-Bromo-benzyl)-3-difluoromethyl-[1,4]naphthoquinone (P_TM101)

As starting materials for the coupling reaction difluoromenadione and 4-bromophenylacetic acid were used. Synthesis is realized according to the general procedure described in general procedure of example 1. After chromatography on silica gel (petroleum ether:$CH_2Cl_2$=1:1, UV), 132 mg (0.35 mmol, 73% yield) of P_TM101 were isolated as yellow solid.

Melting point: 103-104° C. —$^1$H-NMR (300 MHz, $CDCl_3$): δ=8.07-8.13 (m, 1H), 7.99-8.05 (m, 1H), 7.70-7.79 (m, 2H), 7.36 (d, $^3$J=8.46 Hz, 2H), 7.24 (t, $^1$J=53.87 Hz, 1H, $CHF_2$), 7.18 (d, $^3$J=8.42 Hz, 2H), 4.19 (s, 2H). —$^{13}$C-NMR (75 MHz, $CDCl_3$): δ=184.38 ($C_q$), 182.79 ($C_q$), 149.21 ($C_q$), 136.03 ($C_q$), 134.41 (CH), 131.76 ($C_q$), 131.63 (CH), 130.89 (CH), 126.87 (CH), 126.54 (CH), 120.67 ($C_q$), 110.45 ($CHF_2$, $^1$J=239.85 Hz), 31.66 ($CH_2$). —EI MS (70 eV, m/z (%)): 377.1 ([M]$^+$, 21), 325.1 (11), 257.1 (10), 169.0 (100), 90.1 (18). —IR (KBr): 3436 cm$^{-1}$ (b, w), 3100 (w), 3076 (w), 3049 (w), 3018 (w), 2936 (w), 1672 (vs), 1657 (vs), 1625 (s), 1594 (s), 1487 (vs), 1406 (m), 1329 (s), 1297 (vs), 1181 (m), 1123 (s), 1082 (s), 1071 (m), 1035 (vs), 1013 (s), 876 (m), 831 (s), 788 (s), 733 (s), 713 (m), 535 (m). —EA: obs. C, 57.01%; H, 3.12%, calcd. C, 57.32%; H, 2.94% for $C_{18}H_{11}BrF_2O_2$.

EXAMPLE 1.30

2-(2-Bromo-4-methoxy-benzyl)-3-methyl-[1,4]naphthoquinone (P_TM102)

As starting materials for the coupling reaction menadione and 2-Bromo-4-methoxyphenylacetic acid were used. Synthesis is realized according to the general procedure described in general procedure of example 1. After chromatography on silica gel (petroleum ether:$CH_2Cl_2$=1:1, UV), 857 mg (2.31 mmol, 57% yield) of P_TM102 were isolated as yellow oil.

$^1$H-NMR (300 MHz, $CDCl_3$): δ=7.99-8.08 (m, 2H), 7.63-7.69 (m, 2H), 7.09 (d, $^4$J=2.63 Hz, 1H), 6.79 (d, $^3$J=8.57 Hz, 1H), 6.66 (dd, $^3$J=8.61 Hz, $^4$J=2.63 Hz, 1H), 3.99 (s, 2H), 3.70 (s, 3H), 2.08 (s, 3H). —$^{13}$C-NMR (75 MHz, $CDCl_3$): δ=185.06 ($C_q$), 184.40 ($C_q$), 158.55 ($C_q$), 145.64 ($C_q$), 144.90 ($C_q$), 133.54 (CH), 133.51 (CH), 132.14 ($C_q$), 132.01 ($C_q$), 129.22 ($C_q$), 129.08 (CH), 126.52 (CH), 126.31 (CH), 124.71 ($C_q$), 118.13 (CH), 113.67 (CH), 55.48 ($CH_3$), 31.76 ($CH_2$), 13.27 ($CH_3$). —EI MS (70 eV, m/z (%)): 370.11 ([M]$^+$, 2), 355.08 (8), 291.17 (100), 276.14 (8), 248.14 (5), 202.12 (3). —IR (film): 3295 cm$^{-1}$ (w), 3069 (w), 3004 (w), 2940 (w), 2987 (w), 1685 (m), 1660 (vs), 1596 (vs), 1566 (m), 1491 (vs), 1439 (m), 1331 (m), 1295 (vs), 1239 (vs), 1186 (m), 1029 (s), 861 (m), 712 (s), 696 (s). —EA: obs. C, 61.64%; H, 4.35%, calcd. C, 61.47%; H, 4.07% for $C_{19}H_{15}BrO_3$.

EXAMPLE 2

2-(3,6-Dioxo-cyclohexa-1,4-dienylmethyl)-3-methyl-4a,8a-dihydro-[1,4]naphthoquinone (P_TM63)

P_TM60 (200 mg, 0.62 mmol) obtained according to example 1.19 was dissolved in a mixture of 40 mL $CH_3CN$ and 10 mL $H_2O$ by gently warming to give a yellow solution. Cerium(IV) ammonium nitrate (CAN) (918 mg, 1.67 mmol) in 10 mL $CH_3CN/H_2O$ (v/v=1:1) was added to the previous mixture at room temperature to give an orange-red solution which was stirred for 1.5 hours. $CH_3CN$ was removed in vacuo, the product was extracted with $CH_2Cl_2$ (5×20 mL), dried over $MgSO_4$ and purified by flash-chromatography. After chromatography on silica gel (petroleum ether:$CH_2Cl_2$=1:3, UV), 74 mg (0.25 mmol, 41% yield) of P_TM63 were isolated as yellow solid. Melting point: 142-144° C. —$^1$H-NMR (300 MHz, $CDCl_3$): δ=8.10 (dd, $^3$J=6.62 Hz, $^4$J=2.27 Hz, 1H), 8.05 (dd, $^3$J=6.86 Hz, $^4$J=1.99 Hz, 1H), 7.69-7.74 (m, 2H), 6.81 (d, $^3J$=10.10 Hz, 1H), 6.71 (dd, $^3J$=10.10 Hz, $^4J$=2.49 Hz, 1H), 6.35 (d, $^4J$=1.85 Hz, 1H), 3.79 (s, 2H), 2.17 (s, 3H). —$^{13}$C-NMR (75 MHz, CDCl$_3$): δ=187.14 ($C_q$), 186.48 ($C_q$), 184.49 ($C_q$), 183.90 ($C_q$), 146.28 (s, $C_q$), 145.70 ($C_q$), 142.11 ($C_q$), 136.69 (CH), 136.43 (CH), 133.85 (CH), 133.76 (CH), 132.61 (CH), 132.06 ($C_q$), 131.79 ($C_q$), 126.56 (CH), 126.54 (CH), 26.32 (CH$_2$), 13.32 (CH$_3$). —EI MS (70 eV, m/z (%)): 292.1 (M$^+$, 100), 264.1 (15), 235.1 (19), 221.1 (13). —IR (KBr): 3423 cm$^{-1}$ (b, m), 3027 (w), 2937 (w), 1659 (vs), 1624 (m), 1596 (m), 1379 (w), 1334 (m), 1295 (vs), 731 (m), 694 (m). —EA: obs. C, 72.83%, H, 4.26%, calcd. C, 73.07%; H, 4.22% for $C_{12}H_{14}O_4 \cdot 0.2 H_2O$.

EXAMPLE 3

2-Methyl-3-(4-amino-benzyl)-4a,8a-dihydro-[1,4]naphthoquinone (P_TM103)

To a solution of P_TM45 (100 mg, 0.265 mmol) obtained according to example 1.12 in 7 mL dry CH$_2$Cl$_2$, trifluoroacetic acid (157 μL, 2.04 mmol) was added at 0° C. The solution was stirred for 16 h at room temperature. The mixture was quenched by addition of 20 mL sat. Na$_2$CO$_3$-solution, the product was extracted with CH$_2$Cl$_2$ (4×10 mL), dried over MgSO$_4$ and purified by flash-chromatography on silica gel (CH$_2$Cl$_2$:MeOH=9:1, UV) to give 62 mg (0.22 mmol) of analytically pure P_TM103 as red solid in yield of 84%.

Melting point: 152-153° C. —$^1$H-NMR (300 MHz, CDCl$_3$): δ=8.04-8.06 (m, 2H), 7.65-7.68 (m, 2H), 7.00 (d, $^3J$=8.32 Hz, 2H), 6.57 (d, $^3J$=8.36 Hz, 2H), 3.89 (s, 2H), 2.23 (s, 3H). —$^{13}$C-NMR (75 MHz, CDCl$_3$): δ=185.54 ($C_q$), 184.78 ($C_q$), 145.83 ($C_q$), 144.77 ($C_q$), 144.71 ($C_q$), 143.83 ($C_q$), 133.38 (CH), 133.34 (CH), 132.11 ($C_q$), 129.51 (CH), 126.39 (CH), 126.17 (CH), 115.39 ($C_q$), 115.36 (CH), 31.53 (CH$_2$), 13.17 (CH$_3$). —EI MS (70 eV, m/z (%)): 277.1 ([M]$^+$, 52), 262.2 (100), 106.1 (12). —IR (KBr): 3439 cm$^{-1}$ (b, s), 3380 (m), 1659 (vs), 1619 (s), 1594 (m), 1515 (s), 1334 (w), 1295 (vs), 1261 (w), 819 (w), 786 (w), 771 (w), 708 (m), 693 (w), 630 (w), 605 (w), 572 (w), 512 (w), 458 (w), 423 (w). —EA: obs. C, 76.46%; H, 5.41%; N, 4.85%, calcd. C, 76.46%; H, 5.69%; N, 4.88% for $C_{18}H_{15}NO_2 \cdot 0.3 CH_3OH$.

EXAMPLE 4

General Procedure for the Oxidation of Benzyl Derivatives to the Corresponding Benzoyl-Derivatives H$_5$IO$_6$ (1.40 g, 6.16 mmol) was dissolved in 25 mL acetonitrile by vigorous stirring and then CrO$_3$ (17.6 mg, 0.18 mmol) was dissolved into the mixture to give an orange solution. The benzyl-derivative (0.88 mmol) was added to the above solution with stirring. The solution turned to an orange suspension within a few seconds that turned yellow after a few minutes. The solution was stirred at room temperature until all starting material was consumed (TLC control). The solvent was removed in vacuo and the residue was purified by flash-chromatography to give the corresponding benzoyl-derivative.

EXAMPLE 4.1

4-(3-Methyl-1,4-dioxo-1,4,4a,8a-tetrahydro-naphthalene-2-carbonyl)-benzoic acid (P_TM22)

As starting material P_TM21 synthesized according to example 1.1 was used. Synthesis is realized according to the general procedure described in general procedure of example 4. After chromatography on silica gel (CH$_2$Cl$_2$:MeOH:CH$_3$COOH=19:1:0.1, UV), 389 mg (1.22 mmol, 67% yield) of P_TM22 were isolated as yellow solid.

Melting point: 201° C. decomposition. —$^1$H-NMR (300 MHz, DMSO): δ=13.38 (s, 1H), 7.87-8.19 (m, 8H), 1.95 (s, 3H). —$^{13}$C-NMR (75 MHz, DMSO): δ=193.64 ($C_q$), 184.07 ($C_q$), 183.37 ($C_q$), 166.40 ($C_q$), 144.34 ($C_q$), 142.58 ($C_q$), 138.23 ($C_q$), 135.79 ($C_q$), 134.51 (CH), 134.16 (CH), 131.96 ($C_q$), 131.17 ($C_q$), 129.94 (CH), 129.31 (CH), 126.19 (CH), 125.70 (CH), 13.47 (CH$_3$). —HR-EI MS m/z (%): obs. 320.0699, calcd. 320.0685 for $C_{19}H_{12}O_5$. —IR (KBr): 3437 cm$^{-1}$ (b, m), 3070 (w), 1774 (w), 1685 (vs), 1669 (vs), 1594 (m), 1502 (w), 1407 (w), 1292 (vs), 1226 (m), 1110 (w), 979 (w), 763 (m), 730 (w), 714 (w), 691 (w), 652 (w). —EA: obs. 71.07%; H, 4.00%, calcd. C, 71.25%; H, 3.78% for $C_{19}H_{12}O_5$.

EXAMPLE 4.2

2-Methyl-3-(4-bromo-benzoyl)-4a,8a-dihydro-[1,4]naphthoquinone (P_TM25)

As starting material P_TM24 prepared according to example 1.2 was used. Synthesis is realized according to the general procedure described in general procedure of example 4. After chromatography on silica gel (petroleum ether:CH$_2$Cl$_2$=1:3, UV), 133 mg (0.38 mmol, 43% yield) of P_TM25 were isolated as yellow solid.

Melting point: 170-171° C. —$^1$H-NMR (300 MHz, CDCl$_3$): δ=8.14-8.17 (m, 1H), 8.03-8.06 (m, 1H), 7.73-7.81 (m, 4H), 7.64 (t, $^3J$=2.08 Hz, 1H), 7.61 (t, $^3J$=1.95 Hz, 1H), 2.05 (s, CH$_3$). —$^{13}$C-NMR (75 MHz, CDCl$_3$): δ=192.72 ($C_q$), 184.63 ($C_q$), 183.32 ($C_q$), 144.30 ($C_q$), 143.85 ($C_q$), 134.49 ($C_q$), 134.30 (CH), 134.19 (CH), 132.48 (CH), 131.87 ($C_q$), 131.49 ($C_q$), 130.52 (CH), 130.01 ($C_q$), 126.78 (CH), 126.44 (CH), 13.60 (CH$_3$). —EI MS (70 eV, m/z (%)): 353.9 ([M]$^+$, 41), 275.0 (100), 182.9 (71), 115.0 (50), 76.0 (41). —IR (KBr): 3442 cm$^{-1}$ (b, m), 1669 (vs), 1653 (vs), 1627 (vs), 1586 (m), 1568 (m), 1398 (m), 1378 (m), 1329 (s), 1291 (vs), 1272 (s), 1241 (m), 1176 (m), 1069 (m), 1011 (m), 978 (s), 864 (m), 784 (s), 722 (m), 692 (m). —EA: obs. C, 60.96%; H, 3.24%; Br, 22.60%, calcd. C, 60.87%; H, 3.12%; Br, 22.50% for $C_{18}H_{11}BrO_3$.

EXAMPLE 4.3

2-Methyl-3-(fluoro-benzoyl)-4a,8a-dihydro-[1,4]naphthoquinone (P_TM27)

As starting material P_TM26 prepared according to example 1.3 was used. Synthesis is realized according to the general procedure described in general procedure of example 4. After chromatography on silica gel (petroleum ether:CH$_2$Cl$_2$=1:3, UV), 110 mg (0.37 mmol, 35% yield) of P_TM27 were isolated as yellow solid.

Melting point: 157-158° C. —$^1$H-NMR (300 MHz, CDCl$_3$): δ=8.13-8.16 (m, 1H), 8.03-8.06 (m, 1H), 7.90-7.95 (m, 2H), 7.75-7.78 (m, 2H), 7.12-7.18 (m, 2H), 2.05 (s, 3H). —$^{13}$C-NMR (75 MHz, CDCl$_3$): δ=192.02 ($C_q$), 184.69 ($C_q$), 183.33 ($C_q$), 166.58 ($^1J_{CF}$=257.5 Hz, CF), 144.13 ($C_q$), 144.07 ($C_q$), 134.23 ($^3J_{CF}$=7.1 Hz, CH), 132.30 ($^4J_{CF}$=2.8 Hz, $C_q$), 132.01 (CH), 131.88 (CH), 131.54 ($C_q$), 126.77 (CH), 126.45 (CH), 116.41 ($^2J_{CF}$=22.2 Hz, CH), 13.56 (CH$_3$). —HR-EI MS (m/z): obs. 294.0674, calcd. 294.0692 for $C_{18}H_{11}FO_3$. —IR (KBr): 3436 cm$^{-1}$ (b, m), 1674 (vs), 1655 (vs), 1623 (m), 1597 (vs), 1507 (w), 1412 (w), 1332 (m), 1293 (vs), 1274 (m), 1240 (s), 1156 (m), 979 (w), 866 (w), 841 (w), 768 (w), 712 (w), 618 (m). —EA: obs. C, 73.21%; H, 3.97%, calcd. C, 73.47%; H, 3.77% for $C_{18}H_{11}FO_3$.

EXAMPLE 4.4

2-Methyl-3-(4-trifluoromethyl-benzoyl)-4a,8a-dihydro-[1,4]naphtho-quinone (P_TM33)

As starting material P_TM29 prepared according to example 1.4 was used. Synthesis is realized according to the general procedure described in general procedure of example 4. After chromatography on silica gel (petroleum ether: $CH_2Cl_2$=1:3, UV), 174 mg (0.51 mmol, 36% yield) of P_TM33 were isolated as yellow solid.

Melting point: 155-156° C. —$^1$H-NMR (300 MHz, $CDCl_3$): δ=8.13-8.16 (m, 1H), 7.99-8.04 (m, 3H), 7.72-7.81 (m, 4H), 2.05 (s, 3H). —$^{13}$C-NMR (75 MHz, $CDCl_3$): δ=192.87 ($C_q$), 184.46 ($C_q$), 183.32 ($C_q$), 144.65 ($C_q$), 143.57 ($C_q$), 138.28 ($C_q$), 135.51 ($^2J_{CF}$=32.8 Hz, C—$CF_3$), 134.36 (CH), 134.23 (CH), 131.83 ($C_q$), 131.39 ($C_q$), 129.38 (CH), 126.80 (CH), 126.39 (CH), 126.15 ($^3J_{CF}$=3.68 Hz, CH), 123.36 ($^1J_{CF}$=273.1 Hz, $CF_3$), 13.54 ($CH_3$). —EI MS (70 eV, m/z (%)): 344.0 ([M]$^+$, 100), 315 (14), 275 (51), 173.0 (98), 145.0 (47). —IR (KBr): 3433 cm$^{-1}$ (b, m), 3071 (w), 3032 (w), 2972 (w), 1659 (vs), 1617 (m), 1594 (m), 1490 (m), 1407 (w), 1377 (w), 1333 (m), 1296 (vs), 1103 (w), 1091 (w), 1013 (w), 970 (w), 813 (w), 786 (w), 734 (m), 703 (m), 691 (m), 651 (m). —EA: obs. C, 66.03%; H, 3.33%, calcd. C, 66.28%; H, 3.22% for $C_{19}H_{11}F_3O_3$.

EXAMPLE 1.5

2-Methyl-3-(4-chloro-benzoyl)-4a,8a-dihydro-[1,4]naphthoquinone (P_TM38)

As starting material P_TM30 prepared according to example 1.5 was USED. Synthesis is realized according to the general procedure described in general procedure of example 4. After chromatography on silica gel (petroleum ether: $CH_2Cl_2$=1:10, UV), 560 mg (1.80 mmol, 48% yield) of P_TM38 were isolated as yellow solid.

Melting point: 136-137° C. —$^1$H-NMR (300 MHz, $CDCl_3$): δ=8.13-8.16 (m, 1H), 8.02-8.05 (m, 1H), 7.83 (d, $^3J$=8.60 Hz, 2H), 7.75-7.78 (m, 2H), 7.45 (d, $^3J$=8.59 Hz, 2H), 2.04 (s, 3H). —$^{13}$C-NMR (75 MHz, $CDCl_3$): δ=192.50 ($C_q$), 184.65 ($C_q$), 183.34 ($C_q$), 144.27 (s, $C_q$), 143.89 (s, $C_q$), 141.16 (s, $C_q$), 134.30 (CH), 134.20 (CH), 134.10 ($C_q$), 131.87 ($C_q$), 131.49 ($C_q$), 130.49 (CH), 129.49 (CH), 126.77 (CH), 126.44 (CH), 13.59 ($CH_3$). —EI MS (70 eV, m/z (%)): 310.9 ([M]$^+$, 100), 284.9 (41). —IR (KBr): 3453 cm$^{-1}$ (b, m), 1668 (vs), 1628 (m), 1587 (vs), 1571 (m), 1401 (m), 1380 (w), 1329 (m), 1292 (vs), 1274 (s), 1236 (m), 1091 (s), 978 (m), 829 (w), 784 (m), 730 (w), 704 (w), 691 (w), 531 (w). —EA: obs. C, 69.28%; H, 3.63%; Cl, 11.18%, calcd. C, 69.58%; H, 3.57%; Cl, 11.41% for $C_{18}H_{11}ClO_3$.

EXAMPLE 4.6

2-Methyl-3-(4-methoxy-benzoyl)-4a,8a-dihydro-[1,4]naphthoquinone (P_TM34)

As starting material P_TM31 prepared according to example 1.6 was used. Synthesis is realized according to the general procedure described in general procedure of example 4. After chromatography on silica gel (petroleum ether: $CH_2Cl_2$=1:10, UV), 541 mg (1.77 mmol, 64% yield) of P_TM34 were isolated as yellow solid.

Melting point: 150-151° C. —$^1$H-NMR (300 MHz, $CDCl_3$): δ=8.11-8.14 (m, 1H), 8.02-8.05 (m, 1H), 7.86 (d, $^3J$=8.92 Hz, 2H), 7.71-7.78 (m, 2H), 6.93 (d, $^3J$=8.93 Hz, 2H), 3.85 (s, 3H), 2.03 (s, 3H). —$^{13}$C-NMR (75 MHz, $CDCl_3$): δ=191.88 ($C_q$), 184.92 ($C_q$), 183.36 ($C_q$), 164.65 ($C_q$), 144.55 ($C_q$), 143.59 ($C_q$), 134.05 (CH), 134.01 (CH), 131.86 ($C_q$), 131.62 (CH), 128.88 ($C_q$), 126.59 (CH), 126.36 (CH), 114.32 (CH), 55.58 ($CH_3$), 13.54 ($CH_3$). —EI MS (70 eV, m/z (%)): 306.0 ([M]$^+$, 85), 275 (14), 134.9 (100). —IR (KBr): 3400 (b, m), 3076 (w), 3006 (w), 2937 (w), 2843 (w), 1668 (vs), 1653 (vs), 1624 (m), 1598 (s), 1573 (s), 1511 (s), 1423 (s), 1379 (m), 1344 (m), 1329 (s), 1291 (vs), 1265 (vs), 1246 (vs), 1171 (vs), 1026 (m), 978 (m), 834 (m), 765 (s), 715 (m), 618 (m). —EA: obs. C, 74.15%; H, 4.60%, calcd. C, 74.50%; H, 4.61% for $C_{19}H_{14}O_4$.

EXAMPLE 4.7

2-Methyl-3-(2-methoxy-benzoyl)-4a,8a-dihydro-[1,4]naphthoquinone (P_TM35)

As starting material P_TM32 prepared according to example 1.7 was used. Synthesis is realized according to the general procedure described in general procedure of example 4. After chromatography on silica gel ($CH_2Cl_2$: ethyl acetate=1:1, UV), 279 mg (0.91 mmol, 33% yield) of P_TM35 were isolated as yellow solid.

Melting point: 146-147° C. —$^1$H-NMR (300 MHz, $CDCl_3$): δ=8.12-8.18 (m, 1H), 8.02-8.11 (m, 2H), 7.69-7.74 (m, 2H), 7.51-7.61 (m, 1H), 7.10 (t, $^3J$=2.93 Hz, 1H), 6.85 (d, $^3J$=3.26 Hz, 1H), 3.54 (s, 3H), 2.02 (s, 3H). —$^{13}$C-NMR (75 MHz, $CDCl_3$): δ=191.70 ($C_q$), 185.74 ($C_q$), 183.33 ($C_q$), 159.90 ($C_q$), 147.88 ($C_q$), 139.86 ($C_q$), 135.93 (CH), 133.85 (CH), 131.99 ($C_q$), 131.77 ($C_q$), 130.86 (CH), 126.55 (CH), 126.01 (CH), 125.68 ($C_q$), 121.31 (CH), 112.30 (CH), 55.91 ($CH_3$), 12.91 ($CH_3$). —EI MS (70 eV, m/z (%)): 306.0 ([M]$^+$, 100), 274.0 (32), 135.0 (100). —IR (KBr): 3400 cm$^{-1}$ (b, m), 3100 (w), 3068 (w), 2997 (w), 2943 (w), 2837 (w), 1661 (vs), 1652 (vs), 1626 (m), 1595 (vs), 1484 (s), 1466 (m), 1435 (m), 1385 (m), 1330 (s), 1295 (vs), 1265 (m), 1247 (m), 1224 (m), 1185 (m), 1161 (m), 1018 (m), 981 (s), 770 (vs), 755 (vs), 723 (m). —EA: obs. C, 73.90%; H, 4.65%, calcd. C, 73.74%; H, 4.68% for $C_{19}H_{14}O_4$·0.2$H_2O$.

EXAMPLE 4.8

2-Methyl-3-(4-nitro-benzoyl)-4a,8a-dihydro-[1,4]naphthoquinone (P_TM40)

As starting material P_TM37 prepared according to example 1.9 was used. Synthesis is realized according to the general procedure described in general procedure of example 4. After chromatography on silica gel (petroleum ether: $CH_2Cl_2$=1:10, UV), 506 mg (1.57 mmol, 48% yield) of P_TM40 were isolated as yellow solid.

Melting point: 170-171° C. —$^1$H-NMR (300 MHz, $CDCl_3$): δ=8.30-8.33 (d, $^3J$=8.81 Hz, 2H), 8.14-8.17 (m, 1H), 8.01-8.06 (m, 3H), 7.74-7.82 (m, 2H), 2.07 (s, 3H). —$^{13}$C-NMR (75 MHz, $CDCl_3$): δ=192.47 ($C_q$), 184.34 ($C_q$), 183.34 ($C_q$), 150.98 ($C_q$), 145.12 ($C_q$), 143.19 ($C_q$), 140.00 ($C_q$), 134.54 (CH), 134.36 (CH), 131.83 ($C_q$), 131.33 ($C_q$), 130.05 (CH), 126.46 (CH), 124.30 (CH), 13.63 ($CH_3$). —EI MS (70 eV, m/z (%)): 321 ([M]$^+$, 51), 272.9 (100), 245.1 (52), 153.0 (42), 115.1 (46). —IR (KBr): 3433 cm$^{-1}$ (b, s), 1689 (s), 1668 (vs), 1654 (vs), 1627 (w), 1596 (m), 1527 (vs), 1378 (w), 1345 (s), 1322 (m), 1292 (vs), 1272 (m), 1228 (m), 979 (m), 856 (w), 781 (m), 724 (m), 697 (w). —EA: obs. C, 66.39%; H, 3.64%; N, 4.19%, calcd. C, 66.55%; H, 3.54%; N, 4.31% for $C_{18}H_{11}NO_5 \cdot 0.2H_2O$.

EXAMPLE 4.9

2-Methyl-3-(4-cyano-benzoyl)-4a,8a-dihydro-[1,4] naphthoquinone (P_TM46)

As starting material P_TM41 prepared according to example 1.10 was used. After chromatography on silica gel (petroleum ether:$CH_2Cl_2$=1:3, UV), 148 mg (0.49 mmol, 47% yield) of P_TM46 were isolated as yellow solid.

Melting point: 185-186° C. —$^1$H-NMR (300 MHz, $CDCl_3$): δ=8.15-8.18 (m, 1H), 8.02-8.05 (m, 1H), 7.98 (d, $^3J$=8.46 Hz, 2H), 7.77-7.79 (m, 4H), 2.06 (s, 3H). —$^{13}$C-NMR (75 MHz, $CDCl_3$): δ=192.63 ($C_q$), 184.36 ($C_q$), 183.35 ($C_q$), 145.03 ($C_q$), 143.26 ($C_q$), 138.58 ($C_q$), 134.51 (CH), 134.34 (CH), 132.91 (CH), 131.84 ($C_q$), 131.36 ($C_q$), 129.37 (CH), 126.92 (CH), 126.46 (CH), 117.64 ($C_q$), 117.58 ($C_q$), 13.70 ($CH_3$). —EI MS (70 eV, m/z (%)): 300.8 ([M]$^+$, 60), 270.9 (14), 130.0 (41), 102.0 (45). —IR (KBr): 3444 cm$^{-1}$ (b, m), 2233 (w), 1685 (vs), 1658 (vs), 1626 (m), 1594 (m), 1407 (w), 1377 (w), 1330 (m), 1292 (vs), 1271 (m), 1234 (m), 1184 (m), 978 (m), 870 (w), 834 (w), 792 (w), 752 (m), 711 (m), 545 (w). —EA: obs. C, 75.47%; H, 3.96%; N, 4.50%, calcd. C, 75.74%; H, 3.68%; N, 4.65% for $C_{19}H_{11}NO_3$.

EXAMPLE 4.10

2-Methyl-3-(4-tertbutyl-benzoyl)-4a,8a-dihydro-[1,4]naphthoquinone (P_TM48)

As starting material P_TM43 prepared according to example 1.11 was used. Synthesis is realized according to the general procedure described in general procedure of example 4. After chromatography on silica gel (petroleum ether: $CH_2Cl_2$=1:10, UV), 103 mg (0.31 mmol, 33% yield) of P_TM48 were isolated as yellow solid.

Melting point: 64-65° C. —$^1$H-NMR (300 MHz, $CDCl_3$,): δ=8.11-8.14 (m, 1H), 8.02-8.05 (m, 1H), 7.82 (d, $^3J$=8.56 Hz, 2H), 7.72-7.76 (m, 2H), 7.47 (d, $^3J$=8.58 Hz, 2H), 2.04 (s, 3H), 1.31 (s, 9H). —$^{13}$C-NMR (75 MHz, $CDCl_3$,): δ=193.17 ($C_q$), 184.84 ($C_q$), 183.38 ($C_q$), 158.48 ($C_q$), 144.53 ($C_q$), 143.71 ($C_q$), 134.06 (CH), 134.01 (CH), 133.10 ($C_q$), 131.85 ($C_q$), 131.54 ($C_q$), 129.13 (CH), 126.60 (CH), 126.32 (CH), 126.02 (CH), 35.27 ($C_q$), 30.95 ($CH_3$), 13.53 ($CH_3$). —EI MS (70 eV, m/z (%)): 332 ([M]$^+$, 4), 317.1 (18), 275 (100), 161.1 (41). —IR (KBr): 3447 cm$^{-1}$ (b, m), 2965 (w), 1668 (s), 1657 (s), 1632 (s), 1604 (s), 1328 (m), 1291 (s), 729 (w), 701 (w), 691 (w), 668 (w), 652 (w), 547 (w), 505 (w). —EA: obs. C, 78.38%; H, 6.12%, calcd. C, 78.64%; H, 6.12% for $C_{22}H_{20}O_3 \cdot 0.2H_2O$.

EXAMPLE 4.11

3-(4-bromo-benzoyl)-5-hydroxy-2-methyl 4a,8a-dihydro-[1,4]naphthoquinone (P_TM47)

As starting material P_TM42 prepared according to example 1.22 was used. Synthesis is realized according to the general procedure described in general procedure of example 4. After chromatography on silica gel (petroleum ether:ethyl acetate=3:1, UV), 216 mg (0.58 mmol, 52% yield) of P_TM47 were isolated as orange solid. Melting point: 161-162° C. —$^1$H-NMR (300 MHz, $CDCl_3$): δ=11.59 (s, 1H), 7.77 (d, $^3J$=8.63 Hz, 2H), 7.62-7.71 (m, 4H), 7.28 (dd, $^3J$=7.84 Hz, $^4J$=1.70 Hz, 1H), 2.03 (s, 3H). —$^{13}$C-NMR (75 MHz, $CDCl_3$): δ=192.12 ($C_q$), 188.28 ($C_q$), 183.83 ($C_q$), 161.50 ($C_q$), 145.73 ($C_q$), 143.78 ($C_q$), 136.85 (CH), 134.36 ($C_q$), 132.59 (CH), 131.66 ($C_q$), 130.47 (CH), 130.28 ($C_q$), 124.80 (CH), 119.75 (CH), 114.44 ($C_q$), 13.70 ($CH_3$). —EI MS (70 eV, m/z (%)): 370 ([M]$^+$, 41), 290.2 (100), 183.0 (81). —IR (KBr): 3450 cm$^{-1}$ (b, m), 1677 (vs), 1636 (vs), 1615 (s), 1585 (vs), 1570 (m), 1456 (s), 1399 (m), 1382 (m), 1367 (m), 1296 (s), 1273 (vs), 1238 (s), 1068 (m), 1009 (m), 972 (m), 766 (m), 743 (m). —EA: obs. C, 58.21%; H, 3.13%, calcd. C, 58.24%; H, 2.99% for $C_{18}H_{11}BrO_4$.

EXAMPLE 5

4-(3-Methyl-1,4-dioxo-1,4-dihydro-naphthalene-2-carbonyl)-benzoic acid methyl ester (P_TM28)

P_TM22 (500 mg, 1.56 mmol) prepared according to example 4.1 was suspended in 4 mL $SOCl_2$ and refluxed for three hours. The $SOCl_2$ was removed in vacuo and 5 mL methanol was added. The reaction mixture was stirred for three hours at room temperature to give a yellow suspension. The methanol was removed in vacuo and the residue was purified by chromatography.

After chromatography on silica gel (petroleum ether:ethyl acetate=1:1, UV), 351 mg (1.05 mmol, 67% yield) of P_TM28 were isolated as yellow solid.

Melting point: 162-162° C. —$^1$H-NMR (300 MHz, $CDCl_3$): δ=8.15-8.18 (m, 1H), 8.13 (d, $^3J$=8.52 Hz, 2H), 8.04-8.06 (m, 1H), 7.95 (d, $^3J$=8.21 Hz, 2H), 7.77-7.81 (m, 2H), 3.93 (s, 3H), 2.06 (s, 3H). —$^{13}$C-NMR (75 MHz, $CDCl_3$): δ=193.33 ($C_q$), 184.62 ($C_q$), 183.36 ($C_q$), 165.93 ($C_q$), 144.44 ($C_q$), 143.89 ($C_q$), 138.75 ($C_q$), 135.06 ($C_q$), 134.35 (CH), 134.24 (CH), 131.89 ($C_q$), 131.49 ($C_q$), 130.26 (CH), 129.00 (CH), 126.83 (CH), 126.47 (CH), 52.62 ($CH_3$), 13.63 ($CH_3$). —EI MS (70 eV, m/z (%)): 334.1 ([M]$^+$, 69), 275.1 (86), 163.0 (100). —IR (KBr): 3425 cm$^{-1}$ (b, w), 1725 (s), 1670 (s), 1655 (s), 1595 (w), 1436 (w), 1407 (w), 1328 (m), 1291 (vs), 1231 (w), 1110 (m), 978 (w), 777 (w), 733 (w), 720 (w), 697 (w), 692 (w). —EA: obs. C, 71.46%; H, 4.30%, calcd. C, 71.85%; H, 4.22% for $C_{20}H_{14}O_5$.

EXAMPLE 6

2-Methyl-3-(4-hydroxy-benzoyl)-4a,8a-dihydro-[1,4]naphthoquinone (P_TM39)

P_TM34 (100 mg, 0.33 mmol) prepared according to example 4.6 was dissolved in 5 mL dry dichloromethane and cooled to −78° C. 1.0 mL $BBr_3$ (1M in $CH_2Cl_2$) was added dropwise within 20 minutes to give a red solution. The mixture was allowed to warm to room temperature and stirred overnight. 1 mL $H_2O$ was added, stirred for 5 minutes, 2 mL $H_2O$ was added and the mixture was stirred for further ten minutes. The product was extracted with $CH_2Cl_2$ (5×5 mL), dried over $MgSO_4$ and purified by chromatography.

After chromatography on silica gel (cyclohexane:ethyl acetate=1:2, UV), 75 mg (0.25 mmol, 78% yield) of P_TM39 were isolated as yellow solid.

Melting point: 184-185° C. —$^1$H-NMR (300 MHz, $CDCl_3$): δ=8.13-8.16 (m, 1H), 8.03-8.06 (m, 1H), 7.72-7.81 (m, 4H), 6.84 (d, $^3J$=8.77 Hz, 2H), 6.24 (bs, 1H), 2.04 (s, 3H). —$^{13}$C-NMR (75 MHz, $CDCl_3$): =192.01 ($C_q$), 184.92 ($C_q$), 183.67 ($C_q$), 161.58 ($C_q$), 144.48 ($C_q$), 143.88 ($C_q$), 134.25 (CH), 134.13 (CH), 132.01 (CH), 131.90 ($C_q$), 131.58 ($C_q$), 128.84 ($C_q$), 126.72 (CH), 126.46 (CH), 116.00 (CH), 13.64

(CH$_3$). —EI MS (70 eV, m/z (%)): 292.0 ([M]$^+$, 63), 275 (6), 121.0 (100). —IR (KBr): 3443 cm$^{-1}$ (b, vs), 1667 (vs), 1599 (vs), 1517 (w), 1442 (w), 1331 (w), 1292 (vs), 1245 (m), 1167 (m), 773 (w). —EA: obs. C, 72.76%; H, 4.21%, calcd. C, 72.62; H, 4.27% for C$_{18}$H$_{12}$O$_4$·0.3H$_2$O.

EXAMPLE 7

(4-Bromo-phenyl)-(1,4-dimethoxy-3-methyl-naphthalen-2-yl)-methanol (P_TM7)

A solution of 7.0 mL nBuLi (1.6 M in hexane) in 20 mL absolute THF was added at −78° C. dropwise to a solution of 2-bromo-3-methyl-1,4-dimethoxynaphthalene (3.0 g, 10.67 mmol) in 30 mL absolute THF under an atmosphere of nitrogen. The yellow solution was stirred for 30 minutes at −78° C. Then a solution of 4-bromobenzaldehyde (1.97 g, 10.67 mmol) in 15 mL absolute THF was added at −78° C. via transfer canula. The resulting mixture was stirred for 30 minutes at −78° C. and was then allowed to warm to room temperature. The colour turned from yellow to orange to yellow. After stirring for two hours at room temperature the reaction was quenched by addition of 15 mL saturated NH$_4$Cl-solution. 20 mL diethylether was added and the phases were separated. The aqueous phase was extracted twice with 10 mL diethylether. The organic phases were pooled and dried over anhydrous MgSO$_4$. The solvent was removed in vacuo to give a pale-yellow raw product which was purified by chromatography. After chromatography on silica gel (CH$_2$Cl$_2$:petroleum ether=1:2, then 4:1, then pure ethyl acetate, UV), 3.5 g (9.06 mmol, 85% yield) of P_TM7 were isolated as pale-yellow solid.

Melting point: 67-68° C. —$^1$H-NMR (300 MHz, CDCl$_3$): δ=8.01-8.05 (m, 1H), 7.89-7.93 (m, 1H), 7.37-7.49 (m, 4H), 7.14-7.18 (m, 2H), 6.19 (s, 1H), 3.80 (s, 3H), 3.48 (s, 3H), 2.28 (s, 3H). —$^{13}$C-NMR (75 MHz, CDCl$_3$): δ=150.76 (C$_q$), 150.59 (C$_q$), 143.52 (C$_q$), 131.96 (CH), 131.54 (C$_q$) 131.32 (C$_q$), 127.58 (CH), 127.19 (C$_q$), 126.53 (CH), 126.05 (CH), 125.59 (CH), 122.37 (CH), 122.29 (CH), 120.83 (C$_q$), 70.42 (CH), 62.69 (CH$_3$), 61.52 (CH$_3$), 12.66 (CH$_3$). —EI MS (70 eV, m/z (%)): 386.1 ([M]$^+$, 53), 260.1 (14), 184.9 (34), 61.1 (100). —IR (KBr): 3427 cm$^{-1}$ (bs), 3068 (w), 2935 (w), 2839 (m), 1624 (w), 1590 (m), 1486 (m), 1456 (m), 1378 (w), 1351 (vs), 1268 (w), 1193 (w), 1172 (w), 1098 (m), 1068 (vs), 1030 (m), 1009 (s), 961 (m), 774 (m), 727 (w). —EA: obs. C, 61.92%; H, 5.00%, calcd. C, 62.03%, H, 4.95% for C$_{20}$H$_{19}$BrO$_3$.

EXAMPLE 8

2-[(4-Bromo-phenyl)-hydroxy-methyl]-3-methyl-[1,4]naphthoquinone (P_TM23)

P_TM7 (500 mg, 1.29 mmol) prepared according to example 7 was dissolved in 40 mL CH$_3$CN/H$_2$O (v/v=3:1). Cesium (IV) ammonium nitrate (2.13 g, 3.89 mmol) was added at room temperature to form an orange solution which was stirred overnight at room temperature. The CH$_3$CN was removed in vacuo, the product was extracted with CH$_2$Cl$_2$ (4×15 mL), dried over MgSO$_4$ and purified by flash-chromatography. After chromatography on silica gel (petroleum ether:CH$_2$Cl$_2$=1:10, UV), 395 mg (1.11 mmol, 86% yield) of P_TM23 were isolated as yellow solid.

Melting point: 61-62° C. —$^1$H-NMR (300 MHz, CDCl$_3$): δ=8.07-8.11 (m, 1H), 7.97-8.01 (m, 1H), 7.67-7.76 (m, 2H), 7.45 (d, $^3$J=8.36 Hz, 2H), 7.26 (d, $^3$J=8.95 Hz, 2H), 5.92 (d, $^3$J=9.84 Hz, 1H), 4.33 (d, $^3$J=10.78 Hz, 1H), 2.21 (s, 3H). —$^{13}$C-NMR (75 MHz, CDCl$_3$): δ=184.87 (C$_q$), 186.43 (C$_q$), 144.80 (C$_q$), 143.77 (C$_q$), 140.63 (C$_q$), 134.11 (CH), 133.84 (CH), 131.83 (C$_q$), 131.68 (CH), 127.05 (CH), 126.53 (CH), 126.40 (CH), 121.51 (C$_q$), 71.06 (CH), 12.54 (CH$_3$). —EI MS (70 eV, m/z (%)): 356.0 ([M]$^+$, 8), 340.9 (100), 275.1 (25), 202.1 (39), 184.9 (42), 115.1 (80), 77.0 (41). —IR (KBr): 3443 cm$^{-1}$ (bs), 1657 (s), 1619 (m), 1592 (m), 1485 (w), 1329 (w), 1292 (s), 1187 (w), 1072 (w), 1010 (w), 785 (w), 718 (w), 536 (w). —EA: obs. C, 60.25%; H, 3.73%, calcd. C, 60.52%; H, 3.67% for C$_{18}$H$_{13}$BrO$_3$.

EXAMPLE 9

N-(2-Cyano-ethyl)-4-(3-methyl-1,4-dioxo-1,4,4a,8a-tetrahydronaphthalen-2-ylmethyl)-benzamide (P_TM53)

P_TM50 (90 mg, 0.29 mmol) prepared according to example 1.13 was dissolved in 3 mL SOCl$_2$ and heated at reflux for two hours to give an orange solution. The SOCl$_2$ was removed in vacuo and the residue was redissolved in 4 mL dry CH$_2$Cl$_2$. Then 3-aminopropionitrile (22 µL, 0.29 mmol) was added and stirred for 1 hour at room temperature. The reaction was quenched with 10 mL H$_2$O and the product was extracted with CH$_2$Cl$_2$ (5×10 mL), dried over MgSO$_4$ and purified by flash-chromatography (cyclohexane:acetone=1:1, SiO$_2$, UV) to give 19 mg P_TM53 as yellow solid in a yield of 18%.

Melting point: 131-132° C. —$^1$H-NMR (300 MHz, CDCl$_3$,): δ=8.06-8.09 (m, 2H), 7.66-7.71 (m, 4H), 7.29 (d, $^3$J=8.10 Hz, 2H), 6.49 (s, 1H), 4.07 (s, 2H), 3.68 (q, $^3$J=6.10 Hz, 2H), 2.71 (t, $^3$J=6.16 Hz, 2H), 2.22 (s, 3H). —$^{13}$C-NMR (75 MHz, CDCl$_3$): δ=185.17 (C$_q$), 184.53 (C$_q$), 67.57 (Cq), 144.85 (C$_q$), 144.51 (C$_q$), 142.63 (C$_q$), 133.64 (CH), 132.10 (C$_q$), 131.93 (C$_q$), 131.71 (sC$_q$), 128.94 (CH), 127.38 (CH), 126.53 (CH), 126.39 (CH), 118.17 (C$_q$), 36.20 (CH$_2$), 32.43 (CH$_2$), 18.56 (CH$_2$), 13.37 (CH$_3$). —EI MS (70 eV, m/z (%)): 358.2 ([M]$^+$, 28), 343.2 (29), 291.1 (40), 40.0 (100). —IR (KBr): 2920 cm$^{-1}$ (m), 2252 (w), 1695 (w), 1660 (vs), 1613 (s), 1594 (s), 1548 (m), 1295 (vs), 1261 (w), 723 (w), 698 (w). —HPLC analysis: R$_t$=18.08 min.

EXAMPLE 10

N-(2-Cyano-ethyl)-4-(3-methyl-1,4-dioxo-1,4,4a,8a-tetrahydro-naphthalene-2-carbonyl)-benzamide (P_TM51)

P_TM51 was prepared according to the synthesis of P_TM53 in example 9. The starting material was P_TM22 prepared according to example 4.1. The compound was obtained as orange solid in a yield of 18%. Melting point: 172-173° C. —$^1$H-NMR (300 MHz, DMSO): δ=9.07 (t, $^3$J=5.53 Hz, 1H), 8.16 (d, $^3$J=8.40 Hz, 2H), 8.09-8.11 (m, 1H), 7.88-7.98 (m, 5H), 3.51 (q, $^3$J=6.30 Hz, 2H), 2.78 (t, $^3$J=6.46 Hz, 2H), 1.92 (s, 3H). —$^{13}$C-NMR (75 MHz, DMSO$_4$): δ=193.59 (C$_q$), 184.15 (C$_q$), 183.41 (C$_q$), 165.64 (C$_q$), 144.22 (C$_q$), 142.66 (C$_q$), 139.03 (C$_q$), 137.26 (C$_q$), 134.51 (CH), 134.18 (CH), 132.01 (C$_q$), 131.22 (C$_q$), 129.31 (CH), 128.01 (CH), 126.20 (CH), 125.71 (CH), 119.21 (C$_q$), 35.51 (CH$_2$), 17.44 (CH$_2$), 13.50 (CH$_3$). —EI MS (70 eV, m/z (%)): 372.2 ([M]$^+$, 100), 303.1 (30), 276.1 (29), 201.1 (61). —IR (KBr): 3419 cm$^{-1}$ (b, s), 3071 (w), 2926 (w), 2252 (w), 1666 (vs), 1595 (m), 1540 (s), 1502 (w), 1440 (w), 1419 (w), 1406 (w), 1379 (w), 1328 (m), 1293 (vs), 1235 (m), 1185 (m), 978 (m), 778 (m), 719 (m), 691 (m), 651 (m). —HPLC analysis: R$_t$=17.59 min.

EXAMPLE 11

General Procedure for the Suzuki Coupling Reaction for the Synthesis of P_TM66, P_TM67 and P_TM69

A Schlenk-tube was flushed with argon and successively filled with 1 equivalent P_TM24 (100 mg, 0.29 mmol) prepared according to example 1.2, 1.1 equivalent boronic acid derivative (0.32 mmol), 3.0 equivalent K2CO3 (122 mg, 0.88 mmol) and finally dissolved in dioxane/water (12 mL/3 mL). The solution was degassed by bubbling argon through the mixture for 20 minutes. Then 4 mol % $PdCl_2$(dppf) (10 mg, 0.012 mmol) was added, the Schlenk-tube was sealed and heated overnight at 80° C. The reaction was quenched by adding 10 mL $H_2O$. All volatiles were removed in vacuo, the product was extracted with $CH_2Cl_2$, dried over $MgSO_4$ and purified by flash-chromatography.

EXAMPLE 11.1

2-(4'-tert-Butyl-biphenyl-4-ylmethyl)-3-methyl-[1,4]naphthoquinone (P_TM66)

As boronic acid tertbutylphenylboronic acid was used as coupling partner for P_TM24 prepared according to example 1.2. After chromatography on silica gel ($CH_2Cl_2$:petroleum ether=3:1, UV), 113 mg (0.286 mmol, 97% yield) of P_TM66 were isolated as yellow solid.

Melting point: 112-114° C. —$^1$H-NMR (300 MHz, $CDCl_3$): δ=8.06-8.13 (m, 2H), 7.66-7.71 (m, 2H), 7.41-7.50 (m, 6H), 7.24-7.30 (m, 2H), 4.06 (s, 2H), 2.28 (s, 3H), 1.35 (s, 9H). —$^{13}$C-NMR (75 MHz, $CDCl_3$): δ=185.34 ($C_q$), 184.63 ($C_q$), 150.13 ($C_q$), 145.25 ($C_q$), 144.40 ($C_q$), 139.24 ($C_q$), 137.85 ($C_q$), 136.75 ($C_q$), 133.45 (CH), 132.12 ($C_q$), 132.03 ($C_q$), 128.93 (CH), 127.21 (CH), 126.59 (CH), 126.46 (CH), 126.25 (CH), 125.64 (CH), 34.47 ($C_q$), 32.08 ($CH_2$), 31.32 ($CH_3$), 13.30 ($CH_3$). —EI MS (70 eV, m/z (%)): 394.3 ([M]$^+$, 42), 379.2 (100). —IR (KBr): 3439 cm$^{-1}$ (b, m), 2962 (w), 1659 (vs), 1620 (m), 1595 (m), 1498 (w), 1462 (w), 1377 (w), 1334 (w), 1295 (s), 1182 (w), 1114 (w), 976 (w), 815 (m), 790 (w), 713 (w), 568 (w). —EA: obs. C, 85.16%; H, 6.66%, calcd. C, 85.25%; H, 6.64% for $C_{28}H_{26}O_2$.

EXAMPLE 11.2

2-(4'-nitro-Butyl-biphenyl-4-ylmethyl)-3-methyl-[1,4]naphthoquinone (P_TM67)

As boronic acid 4-nitrophenylboronic acid was used as coupling partner for P_TM24 prepared according to example 1.2. After chromatography on silica gel ($CH_2Cl_2$:petroleum ether=3:1, UV), 67 mg (0.175 mmol, 59% yield) of P_TM67 were isolated as yellow solid.

Melting point: 197-199° C. —$^1$H-NMR (300 MHz, $CDCl_3$): δ=8.23-8.26 (m, 2H), 8.05-8.11 (m, 2H), 7.65-7.73 (m, 4H), 7.51 (d, $^3$J=8.27 Hz, 2H), 7.34 (d, $^3$J=8.22 Hz, 2H), 4.08 (s, 2H), 2.27 (s, 3H). —$^{13}$C-NMR (75 MHz, $CDCl_3$): δ=185.27 ($C_q$), 184.65 ($C_q$), 147.18 ($C_q$), 147.00 ($C_q$), 144.86 ($C_q$), 144.68 ($C_q$), 139.16 ($C_q$), 136.95 ($C_q$), 133.63 (CH), 132.12 ($C_q$), 131.98 ($C_q$), 129.40 (CH), 127.65 (CH), 127.59 (CH), 126.52 (CH), 126.38 (CH), 124.12 (CH), 32.22 ($CH_2$), 13.40 ($CH_3$). —EI MS (70 eV, m/z (%)): 383.3 ([M]$^+$, 41), 368.2 (100). —IR (KBr): 3436 cm$^{-1}$ (b, m), 3073 (w), 2934 (w), 1661 (vs), 1620 (m), 1596 (vs), 1513 (vs), 1485 (m), 1375 (w), 1344 (vs), 1295 (vs), 1261 (w), 1182 (w), 1111 (m), 974 (w), 852 (m), 821 (m), 787 (w), 745 (m), 711 (m), 693 (m), 555 (w). —EA: obs. C, 72.95%; H, 4.47%; N, 3.56%, calcd. C, 72.79%; H, 4.68%; N, 3.54% for $C_{24}H_{17}NO_4 \cdot 0.7H_2O$.

EXAMPLE 11.3

2-(4'-Dimethylamino-biphenyl-4-ylmethyl)-3-methyl-[1,4]naphtho-quinone (P_TM69)

As boronic acid 4-dimethylaminophenylboronic acid was used as coupling partner for P_TM24 prepared according to example 1.2. After chromatography on silica gel ($CH_2Cl_2$:petroleum ether=3:1, UV), 96 mg (0.25 mmol, 86% yield) of P_TM69 were isolated as black solid.

Melting point: 170-171° C. —$^1$H-NMR (300 MHz, $CDCl_3$): δ=8.05-8.11 (m, 2H), 7.65-7.71 (m, 2H), 7.43 (d, $^3$J=8.39 Hz, 4H), 7.24 (d, $^3$J=8.17 Hz, 2H), 6.76 (d, $^3$J=8.09 Hz, 2H), 4.03 (s, 2H), 2.96 (s, 6H), 2.27 (s, 3H). —$^{13}$C-NMR (75 MHz, $CDCl_3$): δ=185.47 ($C_q$), 184.74 ($C_q$), 145.43 ($C_q$), 144.34 ($C_q$), 139.43 ($C_q$), 135.69 ($C_q$), 133.49 (CH), 133.46 (CH), 132.15 ($C_q$), 132.09 ($C_q$), 128.94 (CH), 127.58 (CH), 126.53 (CH), 126.52 (CH), 126.28 (CH), 112.75 (CH), 40.60 ($CH_3$), 32.08 ($CH_2$), 13.37 ($CH_3$). —EI MS (70 eV, m/z (%)): 381.2 ([M]$^+$, 100), 366.1 (19). —IR (KBr): 3432 cm$^{-1}$ (b, m), 3028 (w), 2922 (w), 2855 (w), 2803 (w), 1660 (vs), 1612 (vs), 1595 (s), 1534 (w), 1504 (vs), 1444 (w), 1375 (m), 1357 (m), 1333 (m), 1294 (vs), 1226 (w), 1168 (w), 946 (w), 810 (s), 790 (s), 766 (w), 722 (w), 711 (w), 692 (w). —EA: obs. C, 81.58%; H, 619%; N, 3.60%, calcd. C, 81.86%; H, 6.08%; N, 3.67% for $C_{26}H_{23}NO_2$.

EXAMPLE 12

2-(4-Chloro-benzyl)-1,4-dimethoxy-3-methyl-naphthalene (P_TM75)

P_TM30 (2 g, 6.74 mmol) prepared according to example 1.5 was suspended in 20 mL EtOH. $SnCl_2$ (3.83 g, 20.22 mmol) was dissolved in 4.5 mL 36% HCl and added dropwise to the previous solution at room temperature and stirred for 40 minutes. The solvent was removed in vacuo to give a white precipitate which separated and dried in vacuo. The white solid was dissolved in 34 mL acetone and dimethylsulfate (3.2 mL, 33.70 mmol) was added. KOH (3.78 g, 67.4 mmol) was dissolved in 15 mL MeOH and added dropwise to the previous solution at 60° C. The solution turned black and a white precipitate was formed. The mixture was heated at 60° C. for 4 hours. The reaction was quenched by adding 30 mL 20% KOH-solution. The product was extracted with $CH_2Cl_2$ (6×30 mL), dried over $MgSO_4$ and purified by chromatography on silica gel ($CH_2Cl_2$:petroleum ether=1:1, UV), to give 1.49 g (4.569 mmol, 68% yield) of P_TM75 as white solid.

Melting point: 101-102° C. —$^1$H-NMR (300 MHz, $CDCl_3$): δ=8.10-8.17 (m, 2H), 7.50-7.56 (m, 2H), 7.22 (d, $^3$J=8.42 Hz, 2H), 7.08 (d, $^3$J=8.39 Hz, 2H), 4.26 (s, 2H), 3.89 (s, 3H), 3.86 (s, 3H), 2.28 (s, 3H). —$^{13}$C-NMR (75 MHz, $CDCl_3$): δ=150.49 ($C_q$), 150.40 ($C_q$), 138.90 ($C_q$), 131.46 ($C_q$), 129.38 (CH), 128.56 ($C_q$), 128.40 (CH), 128.00 ($C_q$), 127.13 ($C_q$), 126.76 ($C_q$), 125.81 (CH), 125.48 (CH), 122.42 (CH), 122.19 (CH), 62.21 ($CH_3$), 61.31 ($CH_3$), 32.07 ($CH_2$), 12.58 ($CH_3$). —EI MS (70 eV, m/z (%)): 326.12 ([M]$^+$, 100), 311.10 (43), 296.08 (8), 279.07 (10), 261.11 (5), 244.10 (10), 215.10 (8). —IR (KBr): 3443 cm$^{-1}$ (b, m), 2990 (w), 2933 (m), 2838 (w), 1592 (m), 1490 (s), 1456 (m), 1377 (m), 1353 (vs), 1273 (w), 1193 (w), 1096 (vs), 1063 (vs), 1028 (m), 1014 (vs), 963 (m), 804 (w), 784 (m), 770 (s), 694 (w). —EA: obs.

C, 73.30%; H, 5.90%; Cl, 10.84%, calcd. C, 73.50%; H, 5.86%, Cl, 10.85% for $C_{20}H_{19}ClO_2$.

EXAMPLE 13

General Procedure for the Buchwald-Hartwig Coupling Reaction Between P_TM75 and Different Amines A Schlenk-tube was flushed with argon and successively filled with 1 equivalent P_TM75 (100 mg, 0.306 mmol) prepared according to example 12, 2.0 equivalent NaO$^t$Bu (59 mg, 0.612 mmol), 5 mol % 1,3-Bis(2,6-diisopropylphenyl)imidazolium chloride (7 mg, 0.015 mmol), 5 mol % Pd(dba)$_2$ (8 mg, 0.015 mmol), 4.0 equivalent amine (1.224 mmol) and 3 mL dry DME. The Schlenk-tube was sealed and heated at 80° C. for 4 to 24 h. The solvent was removed in vacuo and the residue was purified by flash-chromatography.

EXAMPLE 13.1

1-(4-tert-Butyl-benzyl)-4-[4-(1,4-dimethoxy-3-methyl-naphthalen-2-ylmethyl)-phenyl]piperazine (P_TM78)

As amine 1-(4-tert-butylbenzyl)piperazine was used. After chromatography on silica gel ($CH_2Cl_2$:MeOH=40:1, UV), 390 mg (0.746 mmol, 81% yield) of P_TM78 were isolated as grey solid.

Melting point: 63-65° C. —$^1$H-NMR (300 MHz, CDCl$_3$): δ=8.07-8.11 (m, 2H), 7.46-7.52 (m, 2H), 7.35 (d, $^3$J=8.35 Hz, 2H), 7.27 (d, $^3$J=8.31 Hz, 2H), 7.00 (d, $^3$J=8.62 Hz, 2H), 6.80 (d, $^3$J=8.68 Hz), 4.20 (s, 2H), 3.86 (s, 3H), 3.82 (s, 3H), 3.54 (s, 2H), 3.14 (t, $^3$J=4.74 Hz, 4H), 2.59 (t, $^3$J=4.95 Hz, 4H), 2.27 (s, 3H), 1.33 (s, 9H). —$^{13}$C-NMR (75 MHz, CDCl$_3$): δ=150.41 (C$_q$), 150.25 (C$_q$), 149.97 (C$_q$), 149.46 (C$_q$), 134.74 (C$_q$), 131.38 (C$_q$), 129.63 (C$_q$), 128.90 (CH), 128.66 (CH), 127.82 (C$_q$), 127.21 (C$_q$), 125.55 (CH), 125.28 (CH), 125.09 (CH), 122.45 (CH), 122.15 (CH), 116.14 (CH), 62.67 (CH$_2$), 62.26 (CH$_3$), 61.32 (CH$_3$), 53.09 (CH$_2$), 49.34 (CH$_2$), 34.45 (C$_q$), 31.83 (CH$_2$), 31.39 (CH$_3$), 12.63 (CH$_3$). MALDI MS (Dith., m/z): 522.1 (M$^+$). —IR (KBr): 3436 cm$^{-1}$ (s), 2958 (s), 2904 (m), 2879 (m), 2817 (m), 1612 (m), 1592 (m), 1514 (s), 1454 (s), 1375 (m), 1353 (vs), 1268 (m), 1242 (m), 1229 (m), 1147 (m), 1108 (m), 1097 (m), 1066 (s), 1014 (m), 771 (m). EA: obs. C, 80.19%; H, 8.01%; N, 5.35%, calcd. C, 80.42%; H, 8.10%, N, 5.36% for $C_{35}H_{42}N_2O_2$.

EXAMPLE 14

2-[4-(4-Ethyl-piperazin-1-yl)-benzyl]-3-methyl-[1,4]naphthoquinone (P_TM87)

59 mg (0.0957 mmol) P_TM78 prepared according to example 13.1 was dissolved in 2 mL dry $CH_2Cl_2$ and cooled to −78° C. 0.5 mL (0.478 mmol, 1M in $CH_2Cl_2$) BBr$_3$ was added, the mixture was allowed to warm to room temperature and the red suspension was stirred overnight. The mixture was quenched by addition of 2 mL H$_2$O, extracted with $CH_2Cl_2$ (5×10 mL), dried over MgSO$_4$ and purified by chromatography to give analytically pure P_TM87. After chromatography on silica gel ($CH_2Cl_2$:MeOH=40:1, UV), 37 mg (0.075 mmol, 78% yield) of P_TM87 were isolated as red solid. Melting point: 81-82° C. —$^1$H-NMR (300 MHz, CDCl$_3$): δ=8.05-8.08 (m, 2H), 7.65-7.68 (m, 2H), 7.33 (d, $^3$J=8.23 Hz, 2H), 7.24 (d, $^3$J=8.16 Hz, 2H), 7.11 (d, $^3$J=8.50 Hz, 2H), 6.80 (d, $^3$J=8.58 Hz, 2H), 3.93 (s, 2H), 3.51 (s, 2H), 3.13 (t, $^3$J=4.76 Hz, 4H), 2.58 (t, $^3$J=4.99 Hz, 4H), 2.24 (s, 3H), 1.30 (s, 9H). —$^{13}$C-NMR (75 MHz, CDCl$_3$): δ=185.48 (C$_q$), 184.72 (C$_q$), 149.99 (C$_q$), 149.90 (C$_q$), 145.67 (C$_q$), 143.86 (C$_q$), 134.71 (C$_q$), 133.36 (CH), 133.33 (CH), 132.09 (C$_q$), 132.05 (C$_q$), 129.28 (CH), 128.91 (CH), 128.77 (C$_q$), 126.38 (CH), 126.16 (CH), 125.10 (CH), 116.19 (CH), 62.65 (CH$_2$), 53.01 (CH$_2$), 49.11 (CH$_2$), 34.43 (C$_q$), 31.48 (CH$_2$), 31.36 (CH$_3$), 13.18 (CH$_3$). —FAB MS (NBA, m/z (%)): 492.2 ([M]$^+$, 100). —IR (KBr): 3448 cm$^{-1}$ (b, vs), 2961 (m), 2819 (w), 1660 (vs), 1616 (s), 1595 (m), 1514 (s), 1333 (w), 1295 (vs), 1261 (w), 1243 (w), 1230 (w), 815 (w), 803 (w), 707 (w), 581 (w), 555 (w), 537 (w), 528 (w). —EA: obs. C, 77.34%; H, 7.43%; N, 5.32%, calcd. C, 77.19%; H, 7.12%; N, 5.41% for $C_{33}H_{36}N_2O_2 \cdot 0.3\ CH_2Cl_2$.

EXAMPLE 15

2-Difluoromethyl-1,4-dimethoxy-naphthalene (HB39)

The reaction was conducted in a Teflon® bottle under N$_2$-atmosphere. To a solution of 750 mg (3.47 mmol) 1,4-dimethoxy-naphthalene-2-carbaldehyde prepared according to Uno et al, (J. Org. Chem. 1986, 51 (3), 350-8) in 10 mL dry $CH_2Cl_2$ was added 775 µl (950 mg, 5.90 mmol) diethylaminosulfur trifluoride (DAST) or the equal amount of Deoxo-Fluor® and 10 µL (0.17 mmol) ethanol at 0° C. The reaction mixture was stirred for 1 h at this temperature and then heated overnight to 40° C. To run the reaction to completion another 140 µL DAST was added followed by incubation at 40° C. for additional 5 h. 10 mL of saturated NaHCO$_3$-solution was added in small portions to quench the reaction. The organic phase was separated, the aqueous phase was extracted with $CH_2Cl_2$ (2×20 mL), dried over MgSO$_4$ and purified by flash-chromatography on silica gel (petroleum ether:$CH_2Cl_2$=1:1, UV) to give 723 mg HB39 (3.03 mmol, 88%) of an almost colorless solid.

$^1$H-NMR (300 MHz, CDCl$_3$): δ=8.25-8.30 (m, 1H), 8.06-8.11 (m, 1H), 7.53-7.62 (m, 2H), 7.16 (t, $^1$J=55.8 Hz, 1H, CHF$_2$), 6.90 (s, 1H), 4.02 (s, 3H), 3.97 (s, 3H). —$^{13}$C-NMR (75 MHz, CDCl$_3$): δ=152.3 (C$_q$), 148.5 (C$_q$), 127.9 (C$_q$), 126.9 (CH), 126.7 (CH), 122.6 (C$_q$), 122.5 (CH), 122.2 (C$_q$), 122.0 (CH), 111.7 (t, $^1$J=235 Hz, CHF$_2$), 98.6 (CH), 63.8 (CH$_3$), 55.5 (CH$_3$). —$^{19}$F-NMR (CDCl$_3$): δ=−112.37 (d, $^1$J=55.8 Hz); MS (EI, m/z) 238.07 calc. 238.08. —EA: obs. C, 65.39%; H, 5.20%, calcd. C, 65.54%; H, 5.08% for $C_{13}H_{12}F_2O_2$.

EXAMPLE 16

2-Difluoromethyl-1,4-naphthoquinone (HB49)

500 mg (2.10 mmol) 2-difluoromethyl-1,4-dimethoxy-naphthalene (HB39) prepared according to example 15 was dissolved in 10 mL $CH_3CN$ and a solution of 3.45 g (6.30 mmol) CAN in 8 mL H$_2$O was added. The reaction mixture was stirred for 15 min at room temperature, the acetonitrile was removed in vacuo, the product was extracted with $CH_2Cl_2$ (5×10 mL), dried over MgSO$_4$ and purified by flash-chromatography on silica gel (petroleum ether:$CH_2Cl_2$=1:1, UV) to give 405 mg HB49 as yellow solid (1.95 mmol, 93%).

Melting point: 74° C. —$^1$H-NMR (300 MHz, CDCl$_3$): δ=8.07-8.15 (m, 2H), 7.76-7.83 (m, 2H), 7.19 (m, 1H), 6.83 (t, $^1$J=53.9 Hz, CHF$_2$, 1H). —$^{13}$C-NMR (75 MHz, CDCl$_3$): δ 183.9 (C$_q$), 182.4 (C$_q$), 140.4 (t, $^2$J=21.2 Hz, C$_q$), 135.1 (CH), 134.9 (CH), 134.3 (CH), 134.2 (CH), 131.6 (C$_q$), 131.3 (C$_q$), 126.4 (CH), 109.2 (t, $^1$J=240.4 Hz, CHF$_2$). —$^{19}$F-NMR (CDCl$_3$) δ=−123.85 (d, $^1$J=53.9 Hz). —MS (EI, m/z) 208.02 calc. 208.03. —EA: obs. C, 63.58%; H, 3.02%, calcd. C, 63.47%; H, 2.91% for C$_{11}$H$_6$F$_2$O$_2$.

EXAMPLE 17

Inhibition of *P. falciparum* and Human Glutathione Reductase Under Steady-State-Conditions 17.1. Materials and Methods The standard assay was conducted at 25° C. in a 1 mL-cuvette. The assay mixture contained 100 µM NADPH and 1 mM GSSG in GR buffer (100 mM potassium phosphate buffer, 200 mM KCl, 1 mM EDTA, pH 6.9). IC$_{50}$ values were evaluated in duplicate in the presence of seven inhibitor concentrations ranging from 0 to 100 µM. Inhibitor stock solutions were prepared in 100% DMSO. 1% DMSO concentration was kept constant in the assay cuvette. The reaction was started by adding enzyme (8 mU human GR, 6.5 mU *P. falciparum* GR) and initial rates of NADPH oxidation were monitored at 340 nm ($\epsilon_{340\ nm}$=6.22 mM$^{-1}$ cm$^{-1}$).

17.2 Results

They are shown in FIG. 2.

The IC$_{50}$ values were determined for the benzyl-(P_TM24, P_TM26, P_TM29, P_TM30, P_TM31, P_TM36, P_TM63) and benzoyl-substituted derivatives (P_TM22, P_TM25, P_TM27, P_TM28, P_TM33, P_TM34, P_TM40, and P_TM47), under steady-state conditions and were compared with menadione as reference.

In the assay 1 mM glutathione disulfide (GSSG) concentration was used in order to select the most potent Gluthatione reductase inhibitors. This high GSSG concentration used is not a cell-physiological condition but rather a cell-pathological condition at which the GSSG concentration starts to be toxic for the parasite.

Menadione displayed an IC$_{50}$ value of 42.0 µM for PfGR and 27.5 µM for hGR (Bauer et al, *J. Am. Chem. Soc.* 2006, 128, 10784-10794). In general, all benzyl- and benzoyl-substituted derivatives displayed IC$_{50}$ values ranging from 0.8 µM to 8.2 µM for PfGR and 0.3 µM to 8.6 µM for hGR. In particular in the PfGR assay, the benzyl-series showed only moderate inhibition properties with P_TM26 being the best PfGR inhibitor in this series with an IC$_{50}$ value of 7.8 µM. The complete benzyl-series had higher inhibitory capabilities towards the human GR in accordance with P_TM29 being the best hGR inhibitor in this series with an IC$_{50}$ value of 1.6 µM. Compared to their corresponding benzyl-analogues the benzoyl-series displayed lower IC$_{50}$ values: for PfGR with values ranging from 0.8 µM to 6.3 µM and for hGR from 0.3 µM to 2.0 µM attesting a better recognition of a keto group next to the redox-cycling naphthoquinone-moiety towards the human enzyme resulting in an improved inhibition. The "benzhydrol" P_TM23 also behaved as a potent best GR inhibitor in both enzyme assays with IC$_{50}$ values of 4.5 (PfGR) and 1.3 µM (hGR).

EXAMPLE 18

1,4-Naphthoquinone Reductase Activity of *P. falciparum* Glutathione Reductase 18.1. Materials and Methods The reduction assay mixture consisted of 100 mM potassium phosphate buffer pH 6.9, 200 mM KCl, 1 mM EDTA and 100 µM NADPH in a total volume of 1 mL. 1,4-naphthoquinone reductase activity was determined by recording the initial velocities in the presence of increasing naphthoquinone concentrations (0-300 µM). The 1,4-naphthoquinone was first dissolved in DMSO, and a final 1% DMSO concentration was kept constant in the 1,4-naphthoquinone reductase assay. For the determination of K$_M$ and V$_{max}$ values, the steady-state rates were fitted by using nonlinear regression analysis software (Kaleidagraph) to the Michaelis-Menten equation. From these values, the turnover number k$_{cat}$ and the catalytic efficiency k$_{cat}$/K$_M$ were calculated.

18.2 Results

They are given in FIG. 3.

The catalytic parameters of menadione against *Plasmodium falciparum* GR were shown in Biot et al, 2004 J. Med. Chem. 47, 5972-5983) to be 82.2 µM and 9.6 min$^{-1}$ for K$_M$ and k$_{cat}$, respectively, leading to a catalytic efficiency k$_{cat}$/K$_M$ of 1.99 mM$^{-1}$s$^{-1}$.

Compared with menadione as reference, the tested compounds P_TM26, P_TM36, P_TM27, P_TM25, P_TM34 and P_TM33 bearing a various set of substituents showed low K$_M$ values ranging from 6.1 µM (P_TM25) to 56.1 µM (P_TM27) indicating a tighter binding to the enzyme PfGR when compared to menadione. Only P_TM36 with a K$_M$ value of 87 µM showed similar affinity to the enzyme compared to menadione. From the catalytic efficiencies, expressed as k$_{cat}$/K$_M$ values, P_TM27, P_TM25, P_TM34, P_TM23, P_TM39, P_TM40, P_TM47, and P_TM63 behaved as very effective substrates of PfGR with respect to menadione. Compounds with two redox active moieties like P_TM63 (with a second quinone) and P_TM40 (with a nitro-phenyl group) showed 17.2-fold and 3.9-fold increased catalytic efficiencies with respect to menadione. Also an increased oxidant character, expressed with the plumbagin derivative P_TM47, led to 6.3-fold higher substrate efficiency when compared to menadione.

EXAMPLE 19

Redox-Cycling Activity of Methemoglobin(Fe$^{3+}$) into Oxyhemoglobin(Fe$^{2+}$)

19.1 Material and Methods

Since FPIX(Fe$^{2+}$) is an inhibitor of hematin polymerization, compounds displaying the ability to reduce FPIX(Fe$^{3+}$) into FPIX(Fe$^{2+}$) might synergistically contribute with GR inhibition to increased oxidative stress in infected-red blood cells. To evaluate the redox-cycling activity of FPIX(Fe$^{3+}$) into FPIX(Fe$^{2+}$) we set up an assay using the naphthoquinone, the glutathione reductase/NADPH-based system to regenerate the dihydronaphthoquinone continuously and methemoglobin(Fe$^{3+}$) (MetHb). The UV-spectrum of MetHb between 300 nm and 700 nm is characterized by a maximal absorbance at 405 nm and a broad band centered at around 630 nm. After reduction the spectrum of oxyhemoglobin (Fe$^{2+}$) (OxyHb) shows a shift of the maximal absorbance from 405 nm to 410 nm and two weak bands at 536 and 576 nm. We used 20 µM methylene blue as positive control of this redox-cycling activity.

In an Eppendorf tube containing 6.4 mg MetHb dissolved in 885 µL GR buffer (47 mM potassium phosphate buffer pH 6.9, 200 mM KCl, 100 mM EDTA), 10 µL 20 mM P_TM25 dissolved in DMSO and 100 µL NADPH dissolved in GR buffer were added. The reaction was started by the addition of 5 µL human GR and then incubated at 37° C. In a 1 mL cuvette 20 µL of the reaction mixture was diluted with 980 µL GR buffer and a UV-spectra between 300 nm and 700 nm was done after 5 min, 10 min, 20 min and 30 min incubation time. The final concentrations in the reaction mixture were 100 µM MetHb, 200 µM P_TM25, 400 µM NADPH and 1.06 µmol hGR, final DMSO concentration 1%.

Spectra were measured after 5 min (blue), 10 min (black), 20 min (green) and 30 min (red).

19.2 Results

Figure 4:
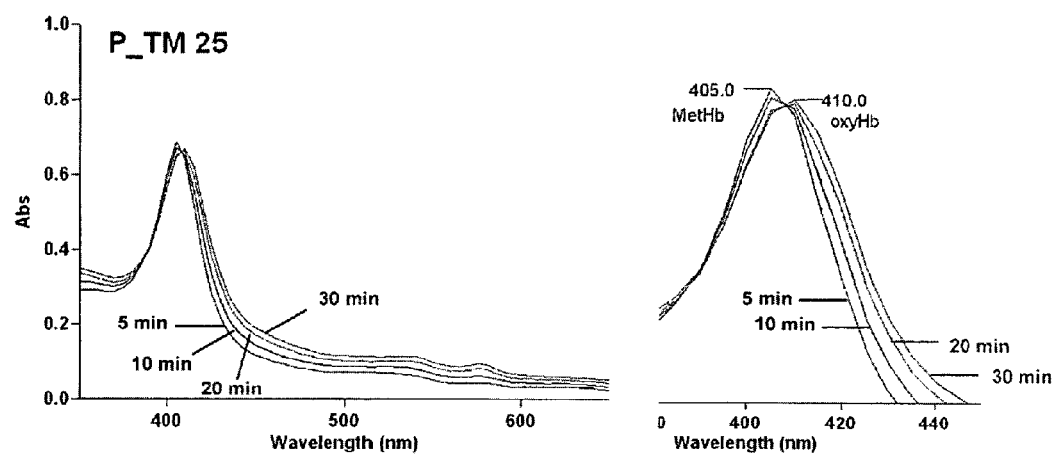

They are shown in FIG. 4.

P_TM25 can undergo redox-cycling of methemoglobin in the presence of GR under physiological conditions, supporting—albeit shown only for P_TM25—that the compounds of the 2-benzyl- and 2-benzoyl-series have several targets making a fast development of resistance in the parasite unlikely, i.e. (i) uncompetitive inhibition of human and *Plasmodium falciparum* glutathione reductases in the low micromolar range with the benzoyl series displaying more potent inhibition properties compared to their benzyl analogs; (ii) redox-cycling of both enzymes (subversive substrates) catalyzing the antioxidant glutathione reductase into a prooxidant enzyme in the presence of the compounds, especially the 2-benzoyl derivatives, (iii) in addition to the redox-cycling of methemoglobin in the presence of the NADPH/GR system and the 2-benzoyl menadione representative P_TM25.

FIG. 4 shows the redox-cycling effect of 100 µM MetHb in the presence of 200 µM P_TM25, 400 µM NADPH and 1 µmol human GR, but the shift of the maximal absorbance from 405 nn to 410 nm is already visible from 50 µM P_TM25 as in the case of menadione (data not shown). The reaction of P_TM25 with MetHb in the presence of NADPH and human GR causes a shift in the $\lambda_{max}$ of MetHb (from 405 to 410 nm). For P_TM25 the shift starts being visible at a P_TM concentration of 50 µM as in the case of menadione. Under the same conditions a clear shift of $\lambda_{max}$ of MetHb was observed in the presence of 20 µM Methylene Blue (MB).

EXAMPLE 20

The Antimalarial and Cytotoxic Effects In Vitro 20.1 Material and Methods

Inhibition of the growth of *P. falciparum* by the naphthoquinones was evaluated by determining the inhibitor concentration required to kill 50% of the parasite ($IC_{50}$ values) using different parasite strains and different assays.

The $IC_{50}$ values against the multidrug-resistant strain Dd2 were determined using the $^3$H-hypoxanthine assay (Desjardins et al, 1979) as well as for the determination of the $IC_{50}$ values against the chloroquine sensitive strains 3D7 and the chloroquine resistant strain K1. The $IC_{50}$ values against Pf-GHA and MRC-5 were determined by using the less sensitive colorimetric NBT-based lactate dehydrogenase assay (Makler et al, *Am. J. Trop. Med. Hyg.* 1993, 48 (6), 739-741) based on redox-reactions.

20.1.1 Determination of $IC_{50}$ Values of Dd2 Growth Inhibition

The $IC_{50}$ was tested by standard in vitro antiproliferation assays (Desjardins et al, 1979 *Antimicrob. Agents Chemother* 1979, 16, 710-718). Infected erythrocytes in ring stage (0.5% parasitemia, 2.5% hematocrit) in 96-well plates were exposed to the compounds for 48 h and then to radioactive hypoxanthine for 24 h. The amount of radioactivity in precipitable material served as an index of cell proliferation.

20.1.2 Determination of $IC_{50}$ Values of 3D7, K1 and Cytotoxicities with Human KB Cells Parasite Cultures. The CQ-sensitive 3D7 clone of the NF54 isolate (Ponnurai et al, 1981 *Trop. Geogr. Med.*, 33, 50-54) and the chloroquine-, pyrimethamine-, and cycloguanil-resistant K1 strain (Thailand) of *Plasmodium falciparum* were acquired from MR4 (Malaria Research and Reference Reagent Resource Center, Manassas, Va.). *P. falciparum* in vitro culture was carried out using standard protocols (Trager et al, 1976 *Science*, 193, 673-675) with modifications. Briefly, parasites were maintained in tissue culture flasks in human A Rh+ erythrocytes at 5% hematocrit in RPMI 1640 supplemented with 25 mM HEPES, 24 mM $NaHCO_3$, 0.2% (w/v) glucose, 0.03% L-glutamine, 150 µM hypoxanthine, and 0.5% Albumax II® (Invitrogen) in a 5% $CO_2$/air mixture at 37° C., and the medium was changed daily.

In Vitro Antiparasitic Bioassays. Drug susceptibility of *P. falciparum* was studied using a modified method (Cameron et al, 2004 *J. Biol. Chem.* 279, 31429-31439) of the protocol described previously (Desjardins et al, 1979). All assays included CQ diphosphate (Sigma, UK) as a standard and control wells with untreated infected and uninfected erythrocytes. $IC_{50}$ values were derived by sigmoidal regression analysis (Microsoft Xlfit™).

Evaluation of the Cytotoxicity. Cytotoxicity on human KB cells (human oral pharyngeal carcinoma) was evaluated using the Alamar Blue assay as described. The positive control drug was podophyllotoxin (Sigma). $IC_{50}$ values were calculated compared to blanks and untreated controls.

20.1.3 Determination of $IC_{50}$ Values of Pf-GHA and Cytotoxicities Against MRC-5 Cells In Vitro Antiparasitic Bioassays. The strain is maintained in RPMI-1640 medium supplemented with 0.37 mM hypoxanthine, 25 mM HEPES, 25 mM $NaHCO_3$, and 10% $O^+$ human serum together with 2-4% washed human $O^+$ erythrocytes. All cultures and assays are conducted under an atmosphere of 4% $CO_2$, 3% $O_2$ and 93% $N_2$. Assays are performed in 96-well microtiter plates, each well containing 10 µL of the watery compound dilutions together with 190 µL of the malaria parasite inoculum (1% parasitaemia, 2% HCT). After 72 h incubation, plates are frozen and stored at −20° C. After thawing, 20 µL of each well is transferred into another plate together with 100 µL Malstat reagent and 20 µL of 1/1 mixture of PES (phenazine ethosulfate, 0.1 mg/mL) and NBT (Nitro Blue Tetrazolium Grade III, 2 mg/mL). Change in colour is measured spectrophotometrically at 655 nm. The results are expressed as % reduction in parasitaemia compared to control wells. Compounds are treated at 5 concentrations (64-16-4-1 and 0.25 µM or µg/mL). Artesunate ($IC_{50}$=0.005+0.004 µM) and chloroquine ($IC_{50}$ 0.05+0.08 µM) are included as reference drugs.

Evaluation of the Cytotoxicity. Human MRC-5$_{SV2}$ cells are cultured in Earl's MEM+5% FCSi. Assays are performed in 96-well microtiter plates, each well containing about $10^4$ cell/well. After 3 days incubation, cell viability is assessed fluorimetrically after addition of resazurin and fluorescence is measured ($\lambda_{ex}$ 550 nm, $\lambda_{em}$ 590 nm). The results are expressed as % reduction in cell growth/viability compared to untreated control wells and $CC_{50}$ is determined Compounds are tested at 5 concentrations (64-14-4-1 and 0.25 µM or mg/mL). When the $CC_{50}$ is lower than 4 µg/mL or µM, the compound is classified as toxic.

20.2. Results

They are given in FIG. 5.

The assay against Dd2 parasites revealed 16 compounds with $IC_{50}$ values below 100 nM. As references standard drugs like atovaquone and chloroquine were also tested displaying $IC_{50}$ values <0.1 nM and 291 nM respectively. These 16 compounds belong to the benzyl series bearing halide- (P_TM24, P_TM26, P_TM30, P_TM57), (several) methoxy- (P_TM31, P_TM32, P_TM58, P_TM59, P_TM60, P_TM61), -hydroxy-(P_TM36), cyano-(P_TM41), nitro- (P_TM37) and alkyl-substituents (P_TM29, P_TM43). The unsubstituted derivative P_TM62 was less active. Compared to the benzyl series the corresponding benzoyl-series displayed lower antimalarial activities with $IC_{50}$ values being superior to 1 μM except in the case of the nitro derivative P_TM40. With a nitro-substituent in para position to the benzyl chain the compound displayed an $IC_{50}$ value of 103 nM which is three-fold higher than in the case of its benzyl analogue P_TM37 with an $IC_{50}$ value of 46 nM.

When testing the compounds against 3D7 and K1 *P. falciparum* strains the results confirmed the high antimalarial activities previously found against Dd2. The most active compounds belong to the benzyl series with $IC_{50}$ values below 1 μM. As control chloroquine was used displaying $IC_{50}$ values around 1 μM against K1 and around 20 nM against 3D7. In contrast with the Dd2 assays only P_TM21 showed a high activity (0.27 μM against 3D7 and 0.10 μM against K1) which was not detected in the previous test displaying an activity against Dd2 of 791 nM.

The third assay—based on the colorimetric detection of the formazan dye as an indicator of the antimalarial activity—only revealed a few compounds active against the parasite strains Pf-GHA. As reference atovaquone was used displaying an $IC_{50}$ value of 0.31 μM. P_TM21, P_TM24, P_TM26, P_TM29, P_TM30, P_TM33, P_TM36, P_TM38, P_TM39, P_TM41, P_TM42, P_TM46, P_TM57, P_TM58, P_TM59, P_TM66, P_TM67, P_TM69, P_TM72, P_TM79, and P_TM81, displayed an antimalarial activity with $IC_{50}$ values below 5 μM, confirming the antimalarial effects but none of the compounds was as active as atovaquone.

EXAMPLE 21

The Antimalarial Activity Against *P. falciparum* Strains In Vitro Exhibiting Different Degrees of Resistance to Chloroquine and Various Known Antimalarial Drugs 21.1. Material and Methods

*Plasmodium falciparum* cultures. Twelve parasite strains or isolates from a wide panel of countries (Africa (3D7), Brazil (Bre), Cambodia (K2 and K14), Cameroon (FCM29), Djibouti (Vol1), the Gambia (FCR3), Indochina (W2), Niger (L1), Senegal (8425), Sierra Leone (D6), and Uganda (PA)) were maintained in culture in RPMI 1640 (Invitrogen, Paisley, United Kingdom), supplemented with 10% human serum (Abcys S.A. Paris, France) and buffered with 25 mM HEPES and 25 mM $NaHCO_3$. Parasites were grown in A-positive human blood under controlled atmospheric conditions that consists of 10% $O_2$, 5% $CO_2$ and 85% $N_2$ at 37° C. with a humidity of 95%.

Drugs. Ferroquine base (SR97193) (FQ) was obtained from Sanofi-Aventis (France). Chloroquine diphosphate (CQ), quinine hydrochloride (QN) and dihydroartemisinin (DHA) were purchased from Sigma (Saint Louis, Mo.). Monodesethylamodiaquine (MDAQ) was obtained from the World Health Organization (Geneva, Switzerland), mefloquine (MQ) from Hoffman-LaRoche (Bale, Switzerland) and lumefantrine (LMF) from Novartis Pharma (Basel, Switzerland).

FQ and synthetic compounds were resuspended and then diluted in RPMI-DMSO (99 v/1 v) to obtain final concentration ranged from 0.125 to 500 nM.

CQ was resuspended in water in concentrations ranging between 5 to 3200 nM. QN, MDAQ, MQ, and DHA which were dissolved first in methanol and then diluted in water to obtain final concentration ranged from 5 to 3200 nM for QN, from 1.56 to 1000 nM for MDAQ, 3.2 to 400 nM for MQ and from 0.1 to 100 nM for DHA. Stock solutions were prepared in ethanol for LMF and then diluted in ethanol to obtain concentrations ranged from 0.5 to 310 nM.

In vitro assays. For in vitro isotopic microtests, 25 μL/well of antimalarial drug and 200 μL/well of the parasitized red blood cell suspension (final parasitemia, 0.5%; final hematocrit, 1.5%) were distributed into 96 well plates. Parasite growth was assessed by adding 1 μCi of tritiated hypoxanthine with a specific activity of 14.1 Ci/mmol (Perkin-Elmer, Courtaboeuf, France) to each well at time zero. The plates were then incubated for 48 h in a controlled atmospheric condition. Immediately after incubation, the plates were frozen and thawed to lyse erythrocytes. The contents of each well were collected on standard filter microplates (Unifilter GF/B; Perkin-Elmer) and washed using a cell harvester (Filter-Mate Cell Harvester; Perkin-Elmer). Filter microplates were dried, and 25 μL of scintillation cocktail (Microscint O; Perkin-Elmer) was placed in each well. Radioactivity incorporated by the parasites was measured with a scintillation counter (Top Count; Perkin-Elmer).

The $IC_{50}$, the drug concentration able to inhibit 50% of parasite growth, was assessed by identifying the drug concentration corresponding to 50% of the uptake of tritiated hypoxanthine by the parasite in the drug-free control wells. The $IC_{50}$ value was determined by non-linear regression analysis of log-based dose-response curves (Riasmart™, Packard, Meriden, USA).

The cut-off values, defined statistically (>2SD above the mean with or without correlation with clinical failures), for in vitro resistance or reduced susceptibility to chloroquine, quinine, mefloquine, monodesethylamodiaquine, lumefantrine and dihydroartemisinin were 100 nM, 800 nM, 30 nM, 60 nM, 150 nM and 10.5 nM, respectively.

21.2. Results

P_TM24, P_TM29, P_TM37, P_TM41, P_TM45 P_TM57, P_TM58, and P_TM60 in *P. falciparum* strains in vitro exhibiting different degrees of resistance to chloroquine (CQ) and various known antimalarial drugs are given in FIG. 6.

From the most sensitive to the most resistant to chloroquine, the strains are: 3D7, D6, 8425, Vol1, L1, PA, Bres, FCR3, W2, K2, K14, and FCM29 and displayed various suceptibilities to known antimalarial agents used as references (FIG. 6). With respect to chloroquine (CQ) the strains showed $IC_{50}$ values from 21.3 (3D7) to 879.0 (FCM29) and $IC_{90}$ from 40.4 nM (3D7) to 1241.7 nM (FCM29). The other known antimalarial drugs are compounds used in human medicine or in clinical studies: quinine (QN), monodesethylamodiaquine (MDAQ), lumefantrine (LMF), mefloquine (MQ), dihydroartemisinin (DHA) and ferroquine (FQ).

EXAMPLE 22

In Vivo Antimalarial Activity Against *P. berghei* in Mice 22.1. Material and Methods The in vivo tests in the mouse model were done according to a standard protocol (Peters et al *Handbook of Animal Models of Infection*; Academic Press, London, 1999; pp. 756-771). Compounds were tested in the *P. berghei* model by using the 4-day suppressive test, as indicated by Peters, and using chloroquine as a positive control. Briefly, naive 18-20-g ANKA BALB/c mice were infected intravenously with $2 \times 10^6$ parasitized red cells on day +0. For administration, compounds were freshly prepared in 10% DMSO in sterile phosphate-buffered saline the day of use. Two hours post-infection mice received the first treatment by the intraperitoneal route. Mice were further treated on days +1-3. Blood films from tail blood were prepared on day +4, and parasitaemia was determined by microscopic examination of Giemsa-stained blood films. Compounds were tested with a daily dose of 50 or 30 mg/kg by the intraperitoneal or oral route. Chloroquine treatment p.o. at 10 mg/kg/day was included as a positive control and resulted in complete inhibition (data not shown). Intraperitoneous administrations of CQ have shown similar activity (98.9% inhibition at 10 mg/kg i.p). Mice were treated and levels of parasitemia determined as described.

22.2. Results

They are given in FIGS. 7 and 8

Six of the most active compounds (P_TM24=HB67, P_TM29, P_TM31, P_TM36, P_TM37, P_TM43) were tested in *P. berghei*-infected mice by intraperitoneal administration. Results of in vivo screens for the six compounds conducted against chloroquine-sensitive *P. berghei* ANKA BALB/c mice according to the Peters's four-day test are given in FIG. 7. For comparative purposes, data acquired in the same screens for CQ and the six derivatives are included. Compounds P_TM37, P_TM43, P_TM36, P_TM29 and P_TM24 showed significant activity on 4-day treatment. The two most active drugs P_TM43 (BJ321) and P_TM37 (BJ323) caused a 43.4% reduction and 42.4% reduction respectively in parasitaemia using a daily dose of 30 mg/kg. At this dose level P_TM31, P_TM36 and P_TM29 could only cause a 20.7-28.4% inhibition of parasitaemia which might result from a poor bioavailability. The compound P_TM24 (HB67) showed only a decrease of 35.6% in parasitaemia at a daily dose of 50 mg/kg ip.

Additional data showing the antimalarial effects of compounds P_TM41, P_TM45, and P_TM57 in *P. berghei*-infected mice by intraperitoneal administration are given in FIG. 8.

The invention claimed is:

1. A compound of formula (I)

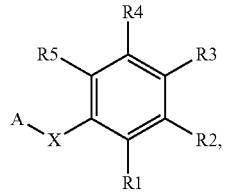

(I)

wherein -A is

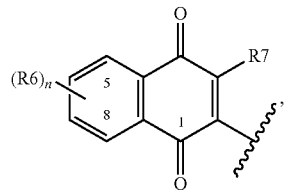

R6, which may be in position 5, 6, 7, or 8 of the phenyl ring of the naphthoquinone, represents a hydrogen atom, a halogen atom, a hydroxy group, a linear or branched ($C_1$-$C_4$)alkyl group, a di- or tri-fluoromethyl group, a trifluoromethoxy group, or a pentafluorosulfanyl group, n is an integer between 0 and 4, and
R7 represents a methyl group;

X represents —C(O)— or —CHY—, with Y being a hydrogen atom, or a hydroxy group; and R1, R2, R3, R4 and R5 each independently represent:
a hydrogen atom,
a halogen atom selected from the group consisting of Br, Cl, and F,
a hydroxy group,
a methyl or t-butyl group,
a di- or trifluoromethyl group,
a methoxy group,
a trifluoromethoxy group,
—$NH_2$,
—$NO_2$,
—CN,
—CONH($CH_2$)$_2$CN
-NHBoc,
the group

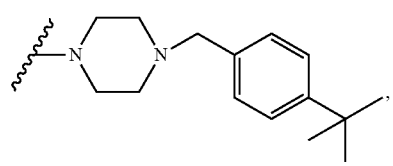 [SMILES: *N1CCN(Cc2ccc(C(C)(C)C)cc2)CC1]

and
a phenyl group substituted in the para position by a t-butyl group, —$NO_2$, —N($CH_3$)$_2$, or —NHC($CH_3$)$_3$,
or a pharmaceutically acceptable salt of said compound,
with the proviso that said compound is not

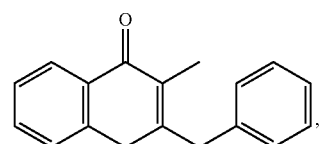

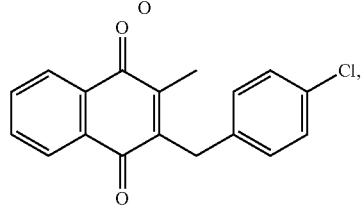

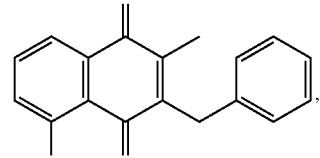

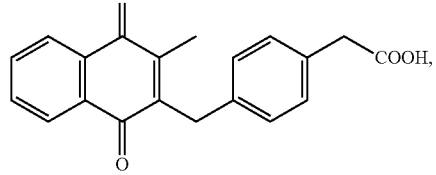

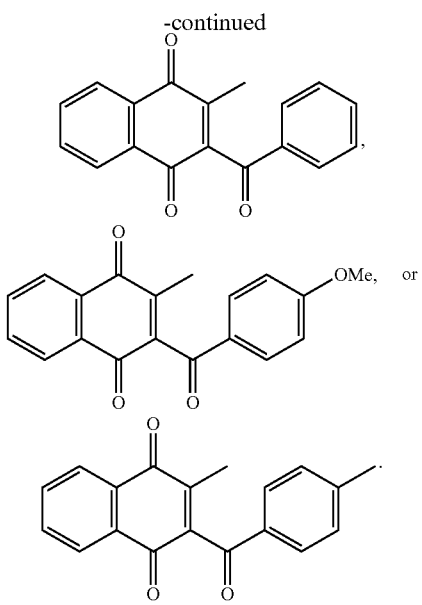

2. The compound according to claim 1, wherein X represents —C(O)— or —CH₂—.

3. The compound according to claim 1, wherein R1, R2, R3, R4 and R5 are each independently selected from the group consisting of a hydrogen atom, a hydroxy group, a methoxy group, a di- or tri-fluoromethyl group, a trifluoromethoxy group, and an amino group.

4. The compound according to claim 1, wherein R1, R2, R3, R4 and R5 are each independently a di- or tri-fluoromethyl group, or a trifluoromethoxy group.

5. An anti-malaria drug, comprising the compound of claim 1.

6. A method for treating a subject for malaria, comprising administering to the subject an effective amount of the compound of claim 1.

7. A pharmaceutical composition, comprising as active ingredient one or more compounds of claim 1, in combination with excipients, pharmaceutically acceptable diluents or carriers.

8. The pharmaceutical composition according to claim 7, further comprising as active ingredients one or more additional antimalarial agents selected from the group consisting of atovaquone, chloroquine, amodiaquine, mefloquine, artemisinin, artesunate, arteether, artemether, menadione, methylene blue, proguanil, cycloguanil, chlorproguanil, pyrimethamine, primaquine, piperaquine, fosmidomycin, halofantrine, dapsone, trimethoprim, sulfamethoxazole, and sulfadoxine.

9. A method for treating malaria in a subject, comprising administering an effective amount of a pharmaceutical composition comprising the compound of claim 1, to a subject in need thereof.

10. A method for reducing the incidence of malaria infection in a subject, comprising administering to the subject an effective amount of the compound of claim 1.

* * * * *